US012728168B2

(12) United States Patent
Ying et al.

(10) Patent No.: US 12,728,168 B2

(45) Date of Patent: Sep. 8, 2026

(54) ANTI-CEA ANTIBODY-EXATECAN ANALOG CONJUGATE AND PHARMACEUTICAL USE THEREOF

(71) Applicants: JIANGSU HENGRUI MEDICINE CO., LTD., Lianyungang (CN); SHANGHAI HENGRUI PHARMACEUTICAL CO., LTD., Shanghai (CN)

(72) Inventors: Hua Ying, Shanghai (CN); Langyong Mao, Shanghai (CN); Sijia Wang, Shanghai (CN)

(73) Assignees: JIANGSU HENGRUI MEDICINE CO., LTD., Lianyungang (CN); SHANGHAI HENGRUI PHARMACEUTICAL CO., LTD., Shanghai (CN)

( * ) Notice: Subject to any disclaimer, the term of this patent is extended or adjusted under 35 U.S.C. 154(b) by 1079 days.

(21) Appl. No.: 17/785,373

(22) PCT Filed: Dec. 15, 2020

(86) PCT No.: PCT/CN2020/136396

§ 371 (c)(1),
(2) Date: Jun. 14, 2022

(87) PCT Pub. No.: WO2021/121204

PCT Pub. Date: Jun. 24, 2021

(65) Prior Publication Data

US 2023/0055408 A1 Feb. 23, 2023

(30) Foreign Application Priority Data

Dec. 16, 2019 (CN) ......................... 201911294912.3

(51) Int. Cl.

*A61K 47/65* (2017.01)
*A61K 39/00* (2006.01)
*A61K 47/54* (2017.01)
*A61K 47/68* (2017.01)
*A61P 35/00* (2006.01)
*C07K 16/30* (2006.01)

(52) U.S. Cl.

CPC ............ *A61K 47/65* (2017.08); *A61K 47/545* (2017.08); *A61K 47/68037* (2023.08); *A61K 47/6853* (2017.08); *A61P 35/00* (2018.01); *C07K 16/3007* (2013.01); *A61K 2039/505* (2013.01); *C07K 2317/24* (2013.01); *C07K 2317/73* (2013.01); *C07K 2317/92* (2013.01)

(58) Field of Classification Search

None

See application file for complete search history.

(56) References Cited

FOREIGN PATENT DOCUMENTS

| | | | |
|---|---|---|---|
| WO | 2015069430 | A3 | 5/2015 |
| WO | 2018177369 | A1 | 10/2018 |

OTHER PUBLICATIONS

Rudikoff, et al., PNAS, 1982, 79, 1979-1983 (Year: 1982).*

Janeway, et al., Immunobiology: The Immune System in Health and Disease, 5th edition, 2001 (Year: 2001).*

Shinmi, et al., Cancer Med, 2017, 6, 798-808 (Year: 2017).*

Nap, Marius et al., Specificity and Affinity of Monoclonal Antibodies against Carcinoembryonic Antigen., Cancer Res. Apr. 15, 1992, vol. 52, No. 8, pp. 2329-2339 (11 pages).

Thomson, D. M. P. et al., The Radioimmunoassay of Circulating Carcinoembryonic Antigen of the Human Digestive System, Proceedings of the National Academy of Sciences of the United States of America, vol. 64, No. 1 (1969), pp. 161-167 (7 pages).

* cited by examiner

*Primary Examiner* — Misook Yu

*Assistant Examiner* — Samantha Lake Hopkins

(74) *Attorney, Agent, or Firm* — Morgan, Lewis & Bockius LLP

(57) ABSTRACT

An anti-CEA antibody-exatecan analog conjugate and a pharmaceutical use thereof. Specifically, the anti-CEA antibody-exatecan analog conjugate is as shown in general formula (Pc-L-Y-D), wherein Pc is an anti-CEA antibody or an antigen-binding fragment thereof; L is a linker unit; Y is selected from $—O—(CR^aR^b)_m—CR^1R^2—C(O)—$, $—O—CR^1R^2—(CR^aR^b)_m—$, $—O—CR^1R^2—$, $—NH—(CR^aR^b)_m—CR^1R^2—C(O)—$, and $—S—(CR^aR^b)_m—CR^1R^2—C(O)$; and n is a decimal or integer from 1 to 10.

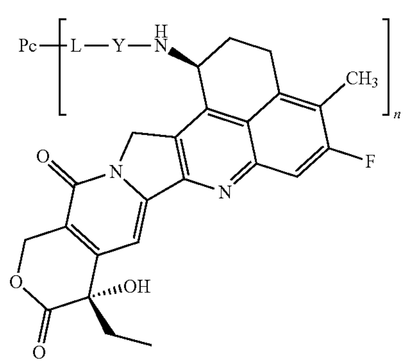

(Pc-L-Y-D)

28 Claims, 3 Drawing Sheets

Specification includes a Sequence Listing.

ANTI-CEA ANTIBODY-EXATECAN ANALOG CONJUGATE AND PHARMACEUTICAL USE THEREOF

CROSS-REFERENCE TO RELATED APPLICATIONS

The present application is the national stage of International Patent Application No. PCT/CN2020/136396, filed on Dec. 15, 2020, which claims the benefit of and priority to the Chinese Patent Application No. 201911294912.3, filed Dec. 16, 2019, which is incorporated herein by reference in their entirety.

SEQUENCE LISTING

The instant application contains a Sequence Listing which has been submitted electronically in ASCII format and is hereby incorporated by reference in its entirety. Said ASCII copy, created on Jun. 14, 2022 is named "702139CPUS 126268-5034-US_ST25_Sequence_Listing. TXT" and is approximately 128 kilobytes in size.

TECHNICAL FIELD

The present disclosure relates to an anti-CEA antibody-exatecan analog conjugate, a preparation method therefor, a pharmaceutical compositions comprising the same, and use thereof in preparing a medicament for the treatment of a CEA-mediated disease or condition, especially use thereof in preparing an anti-cancer medicament.

BACKGROUND

The statement herein merely provide background information related to the present disclosure and may not necessarily constitute the prior art.

Carcinoembryonic antigen (CEA, also known as CEACAM-5 or CD66e), a glycoprotein with a molecular weight of about 180 kDa, is one of the earliest discovered tumor-associated antigens. CEA is a member of the immunoglobulin superfamily and contains 7 domains attached to the cell membrane via a glycosylphosphatidylinositol (GPI) anchor (Thompson J. A., *J Clin Lab Anal.* 5:344-366, 1991). CEA is originally discovered and reported by Gold P and Freedman SO in colon cancer tissue extracts (Gold and Freedman 1965; Gold and Freedman, 1965), and CEA is subsequently reported to be detected in the serum of patients with colon cancer and other tumors using sensitive radioimmunoassay methods, whereas the CEA content in the serum of healthy human or patients with other diseases is extremely low (Thomson, Krupey et al., 1969). CEA expression is increased in cancer cells, and the increased CEA promotes intercellular adhesion and further cell metastasis (Marshall J., *Semin Oncol.,* 30 (Suppl. 8):30-6, 2003). CEA is commonly expressed in epithelial tissues, including cells in the gastrointestinal, respiratory and genitourinary tracts, and cells in the colon, cervix, sudoriferous glands and prostate (Nap et al, *Tumour biol.,* 9(2-3):145-53, 1988; Nap et al, *Cancer Res.,* 52(8):2329-23339, 1992).

Antibody drug conjugate (ADC) links a monoclonal antibody or an antibody fragment to a biologically active cytotoxin via a stable chemical linker compound, fully exploiting the binding specificity of the antibody to surface antigens of normal cells and tumor cells and the high-efficiency of the cytotoxic substance, and also avoiding the former's disadvantage of having a poor therapeutic effect, the latter's disadvantage of having serious toxic side effects, and the like. This means that the antibody drug conjugate can bind to tumor cells more precisely and has a reduced effect on normal cells compared to conventional chemotherapeutic drugs in the past.

At present, some CEA-targeted antibodies and ADC drugs have been reported in patents, such as WO2015069430. However, there is still a need to develop a more effective and safer anti-CEA antibody drug conjugate for better use in the treatment of CEA-associated tumors.

SUMMARY

The present disclosure relates to an anti-CEA antibody drug conjugate and pharmaceutical use thereof, wherein the anti-CEA antibody drug conjugate comprises an anti-CEA antibody or an antigen-binding fragment thereof conjugated to a toxin drug optionally by a linker, wherein the anti-CEA antibody or the antigen-binding fragment thereof comprises a heavy chain variable region and a light chain variable region of the antibody, wherein:

i) an HCDR1 and an HCDR3 of the heavy chain variable region are identical to an HCDR1 and an HCDR3 of a heavy chain variable region set forth in SEQ ID NO: 7, and an HCDR2 of the heavy chain variable region is identical to an HCDR2 of the heavy chain variable region set forth in SEQ ID NO: 7 or differs therefrom by one amino acid; an LCDR1, an LCDR2 and an LCDR3 of the light chain variable region are identical to an LCDR1, an LCDR2 and an LCDR3 of a light chain variable region set forth in SEQ ID NO: 8;

ii) the HCDR1 and the HCDR3 of the heavy chain variable region are identical to an HCDR1 and an HCDR3 of a heavy chain variable region set forth in SEQ ID NO: 9, and the HCDR2 of the heavy chain variable region is identical to an HCDR2 of the heavy chain variable region set forth in SEQ ID NO: 9 or differs therefrom by one amino acid; the LCDR1, the LCDR2 and the LCDR3 of the light chain variable region are identical to an LCDR1, an LCDR2 and an LCDR3 of a light chain variable region set forth in SEQ ID NO: 10;

iii) the HCDR1, the HCDR2 and the HCDR3 of the heavy chain variable region are identical to an HCDR1, an HCDR2 and an HCDR3 of a heavy chain variable region set forth in SEQ ID NO: 11; the LCDR1, the LCDR2 and the LCDR3 of the light chain variable region are identical to an LCDR1, an LCDR2 and an LCDR3 of a light chain variable region set forth in SEQ ID NO: 12; or iv) the HCDR1 and the HCDR3 of the heavy chain variable region are identical to an HCDR1 and an HCDR3 of a heavy chain variable region set forth in SEQ ID NO: 13, and the HCDR2 of the heavy chain variable region is identical to an HCDR2 of the heavy chain variable region set forth in SEQ ID NO: 13 or differs therefrom by one amino acid; the LCDR1 and the LCDR3 of the light chain variable region are identical to an LCDR1 and an LCDR3 of a light chain variable region set forth in SEQ ID NO: 14, and the LCDR2 of the light chain variable region is identical to an LCDR2 of the light chain variable region set forth in SEQ ID NO: 14 or differs therefrom by one amino acid.

In some embodiments of the present disclosure, the anti-CEA antibody or the antigen-binding fragment thereof in the antibody drug conjugate comprises a heavy chain variable region and a light chain variable region, wherein:

v) the heavy chain variable region comprises an HCDR1, an HCDR2 and an HCDR3 set forth in SEQ ID NO: 15, SEQ ID NO: 16 and SEQ ID NO: 17, respectively, and the light chain variable region comprises an LCDR1, an LCDR2 and an LCDR3 set forth in SEQ ID NO: 18, SEQ ID NO: 19 and SEQ ID NO: 20, respectively; or the heavy chain variable region comprises an HCDR1, an HCDR2 and an HCDR3 set forth in SEQ ID NO: 15, SEQ ID NO: 38 and SEQ ID NO: 17, respectively, and the light chain variable region comprises an LCDR1, an LCDR2 and an LCDR3 set forth in SEQ ID NO: 18, SEQ ID NO: 19 and SEQ ID NO: 20, respectively;

vi) the heavy chain variable region comprises an HCDR1, an HCDR2 and an HCDR3 set forth in SEQ ID NO: 21, SEQ ID NO: 22 and SEQ ID NO: 23, respectively, and the light chain variable region comprises an LCDR1, an LCDR2 and an LCDR3 set forth in SEQ ID NO: 24, SEQ ID NO: 25 and SEQ ID NO: 26, respectively; or the heavy chain variable region comprises an HCDR1, an HCDR2 and an HCDR3 set forth in SEQ ID NO: 21, SEQ ID NO: 47 and SEQ ID NO: 23, respectively, and the light chain variable region comprises an LCDR1, an LCDR2 and an LCDR3 set forth in SEQ ID NO: 24, SEQ ID NO: 25 and SEQ ID NO: 26, respectively;

vii) the heavy chain variable region comprises an HCDR1, an HCDR2 and an HCDR3 set forth in SEQ ID NO: 27, SEQ ID NO: 28 and SEQ ID NO: 29, respectively, and the light chain variable region comprises an LCDR1, an LCDR2 and an LCDR3 set forth in SEQ ID NO: 30, SEQ ID NO: 31 and SEQ ID NO: 32, respectively; or viii) the heavy chain variable region comprises an HCDR1 and an HCDR3 set forth in SEQ ID NO: 33 and SEQ ID NO: 34, respectively, and an HCDR2 set forth in SEQ ID NO: 16 or SEQ ID NO: 38; the light chain variable region comprises an LCDR1 and an LCDR3 set forth in SEQ ID NO: 35 and SEQ ID NO: 37 and an LCDR2 set forth in SEQ ID NO: 36 or SEQ ID NO: 64.

In some embodiments, the anti-CEA antibody or the antigen-binding fragment thereof in the antibody drug conjugate comprises a heavy chain variable region and a light chain variable region, wherein:

In some embodiments, the anti-CEA antibody or the antigen-binding fragment thereof in the antibody drug conjugate comprises a heavy chain variable region and a light chain variable region, wherein:

the heavy chain variable region comprises an HCDR1, an HCDR2 and an HCDR3 set forth in SEQ ID NO: 33, SEQ ID NO: 16 and SEQ ID NO: 34, respectively, and the light chain variable region comprises an LCDR1, an LCDR2 and an LCDR3 set forth in SEQ ID NO: 35, SEQ ID NO: 36 and SEQ ID NO: 37, respectively; or the heavy chain variable region comprises an HCDR1, an HCDR2 and an HCDR3 set forth in SEQ ID NO: 33, SEQ ID NO: 38 and SEQ ID NO: 34, respectively, and the light chain variable region comprises an LCDR1, an LCDR2 and an LCDR3 set forth in SEQ ID NO: 35, SEQ ID NO: 36 and SEQ ID NO: 37, respectively; or the heavy chain variable region comprises an HCDR1, an HCDR2 and an HCDR3 set forth in SEQ ID NO: 33, SEQ ID NO: 16 and SEQ ID NO: 34, respectively, and the light chain variable region comprises an LCDR1, an LCDR2 and an LCDR3 set forth in SEQ ID NO: 35, SEQ ID NO: 64 and SEQ ID NO: 37, respectively; or preferably, the heavy chain variable region comprises an HCDR1, an HCDR2 and an HCDR3 set forth in SEQ ID NO: 33, SEQ ID NO: 38 and SEQ ID NO: 34, respectively, and the light chain variable region comprises an LCDR1, an LCDR2 and an LCDR3 set forth in SEQ ID NO: 35, SEQ ID NO: 64 and SEQ ID NO: 37, respectively.

In some embodiments of the present disclosure, the anti-CEA antibody in the antibody drug conjugate is a murine antibody, a chimeric antibody or a humanized antibody.

In some embodiments of the present disclosure, the anti-CEA antibody or the antigen-binding fragment thereof according to any one of the aforementioned embodiments in the antibody drug conjugate comprises a heavy chain variable region and a light chain variable region, wherein:

(a) the heavy chain variable region has an amino acid sequence set forth in SEQ ID NO: 7, or an amino acid sequence having at least 90% identity to the amino acid sequence set forth in SEQ ID NO: 7; and/or the light chain variable region has an amino acid sequence set forth in SEQ ID NO: 8, or an amino acid sequence having at least 90% identity to the amino acid sequence set forth in SEQ ID NO: 8; or (b) the heavy chain variable region has an amino acid sequence set forth in SEQ ID NO: 9, or an amino acid sequence having at least 90% identity to the amino acid sequence set forth in SEQ ID NO: 9; and/or the light chain variable region has an amino acid sequence set forth in SEQ ID NO: 10, or an amino acid sequence having at least 90% identity to the amino acid sequence set forth in SEQ ID NO: 10; or (c) the heavy chain variable region has an amino acid sequence set forth in SEQ ID NO: 11, or an amino acid sequence having at least 90% identity to the amino acid sequence set forth in SEQ ID NO: 11; and/or the light chain variable region has an amino acid sequence set forth in SEQ ID NO: 12, or an amino acid sequence having at least 90% identity to the amino acid sequence set forth in SEQ ID NO: 12; or (d) the heavy chain variable region has an amino acid sequence set forth in SEQ ID NO: 13, or an amino acid sequence having at least 90% identity to the amino acid sequence set forth in SEQ ID NO: 13; and/or the light chain variable region has an amino acid sequence set forth in SEQ ID NO: 14, or an amino acid sequence having at least 90% identity to the amino acid sequence set forth in SEQ ID NO: 14.

In some embodiments of the present disclosure, the anti-CEA antibody or the antigen-binding fragment thereof in the antibody drug conjugate comprises a heavy chain variable region and a light chain variable region, wherein:

(e) the heavy chain variable region has an amino acid sequence set forth in SEQ ID NO: 39, 40, 41 or 42, or an amino acid sequence having at least 90% identity to any one amino acid sequence set forth in SEQ ID NO: 39, 40, 41 or 42; and/or the light chain variable region has an amino acid sequence set forth in SEQ ID NO: 43, 44, 45 or 46, or an amino acid sequence having at least 90% identity to any one amino acid sequence set forth in SEQ ID NO: 43, 44, 45 or 46;

preferably, the heavy chain variable region has an amino acid sequence set forth in SEQ ID NO: 42, and the light chain variable region has an amino acid sequence set forth in SEQ ID NO: 44; or (f) the heavy chain variable region has an amino acid sequence set forth in SEQ ID NO: 48, 49, 50, 51 or 52, or an amino acid sequence having at least 90% identity to any one amino acid sequence set forth in SEQ ID NO: 48, 49, 50, 51 or 52; and/or the light chain variable region has an amino acid sequence set forth in SEQ ID NO: 53, 54 or 55, or an amino acid sequence having at least 90% identity to any one amino acid sequence set forth in SEQ ID NO: 53, 54 or 55; preferably, the heavy chain variable region has an amino acid sequence set forth in SEQ ID NO: 52, and the light chain variable region has an amino acid sequence set forth in SEQ ID NO: 53; or (g) the heavy chain variable region has an amino acid sequence set forth in SEQ ID NO: 56, 57 or 58, or an amino acid sequence having at least 90% identity to any one amino acid sequence set forth in SEQ ID NO: 56, 57 or 58; and/or the light chain variable region has an amino acid sequence set forth in SEQ ID NO: 59, 60, 61, 62 or 63, or an amino acid sequence having at least 90% identity to any one amino acid sequence set forth in SEQ ID NO: 59, 60, 61, 62 or 63; preferably, the heavy chain variable region has an amino acid sequence set forth in SEQ ID NO: 58, and the light chain variable region has an amino acid sequence set forth in SEQ ID NO: 62; or (h) the heavy chain variable region has an amino acid sequence set forth in SEQ ID NO: 65, 66, 67 or 68, or an amino acid sequence having at least 90% identity to any one amino acid sequence set forth in SEQ ID NO: 65, 66, 67 or 68; and/or the light chain variable region has an amino acid sequence set forth in SEQ ID NO: 69, 70, 71, 72, 73, 74, 75 or 76, or an amino acid sequence having at least 90% identity to any one amino acid sequence set forth in SEQ ID NO: 69, 70, 71, 72, 73, 74, 75 or 76;

preferably, the heavy chain variable region has an amino acid sequence set forth in SEQ ID NO: 68, and the light chain variable region has an amino acid sequence set forth in SEQ ID NO: 76.

In some embodiments of the present disclosure, the anti-CEA antibody according to any one of the aforementioned embodiments in the antibody drug conjugate is a humanized antibody comprising a framework region derived from a human antibody or a framework region variant thereof, and the framework region variant has reverse mutations of up to 10 amino acids in a light chain framework region and/or a heavy chain framework region of the human antibody; preferably, the framework region variant is selected from any one of the following (i) to (l):

(i) a framework region of the light chain variable region comprising an LCDR1, an LCDR2 and an LCDR3 having sequences set forth in SEQ ID NO: 18, SEQ ID NO: 19 and SEQ ID NO: 20, respectively, comprising one or more amino acid reverse mutations selected from the group consisting of 46P, 47W, 49Y, 70S and 71Y, and/or a framework region of the heavy chain variable region comprising an HCDR1 having a sequence set forth in SEQ ID NO: 15, an HCDR2 having a sequence set forth in SEQ ID NO: 16 or SEQ ID NO: 38 and an HCDR3 having a sequence set forth in SEQ ID NO: 17, comprising one or more amino acid reverse mutations selected from the group consisting of 38K and 46K;

(j) a framework region of the light chain variable region comprising an LCDR1, an LCDR2 and an LCDR3 having sequences set forth in SEQ ID NO: 24, SEQ ID NO: 25 and SEQ ID NO: 26, respectively, comprising one or more amino acid reverse mutations selected from the group consisting of 2V, 42G, 44V and 71Y, and/or a framework region of the heavy chain variable region comprising an HCDR1 having a sequence set forth in SEQ ID NO: 21, an HCDR2 having a sequence set forth in SEQ ID NO: 22 or SEQ ID NO: 47 and an HCDR3 having a sequence set forth in SEQ ID NO: 23, comprising one or more amino acid reverse mutations selected from the group consisting of 48I, 66K, 67A, 69L, 71V, 73K, 82F and 82A R;

(k) a framework region of the light chain variable region comprising an LCDR1, an LCDR2 and an LCDR3 having sequences set forth in SEQ ID NO: 30, SEQ ID NO: 31 and SEQ ID NO: 32, respectively, comprising one or more amino acid reverse mutations selected from the group consisting of 3V, 43P and 58V, and/or a framework region of the heavy chain variable region comprising an HCDR1, an HCDR2 and an HCDR3 having sequences set forth in SEQ ID NO: 27, SEQ ID NO: 28 and SEQ ID NO: 29, comprising one or more amino acid reverse mutations selected from the group consisting of 38K, 66K and 71V; and (l) a framework region of the light chain variable region comprising an LCDR1 having a sequence set forth in SEQ ID NO: 35, an LCDR2 having a sequence set forth in SEQ ID NO: 36 or SEQ ID NO: 64 and an LCDR3 having a sequence set forth in SEQ ID NO: 37, comprising one or more amino acid reverse mutations selected from the group consisting of 4V, 36Y, 43P, 47V, 49E, 70D and 871; and/or a framework region of the heavy chain variable region comprising an HCDR1 having a sequence set forth in SEQ ID NO: 33, an HCDR2 having a sequence set forth in SEQ ID NO: 16 or SEQ ID NO: 38 and an HCDR3 having a sequence set forth in SEQ ID NO: 34, comprising one or more amino acid reverse mutations selected from the group consisting of the group consisting of 2I, 38K and 46K;

(m) a framework region of the light chain variable region comprising an LCDR1, an LCDR2 and an LCDR3 having sequences set forth in SEQ ID NO: 24, SEQ ID NO: 25 and SEQ ID NO: 26, respectively, comprising one or more amino acid reverse mutations selected from the group consisting of 2V, 42G, 44V and 71Y, and/or a framework region of the heavy chain variable region comprising an HCDR1 having a sequence set forth in SEQ ID NO: 21, an HCDR2 having a sequence set forth in SEQ ID NO: 22 or SEQ ID NO: 47 and an HCDR3 having a sequence set forth in SEQ ID NO: 23, comprising one or more amino acid reverse mutations selected from the group consisting of 66K, 67A, 69L, 71V, 73K, 82F and 82A R;

wherein sites of the reverse mutations are numbered according to Kabat numbering scheme.

In some embodiments of the present disclosure, the anti-CEA antibody according to any one of the aforementioned embodiments in the antibody drug conjugate is a humanized antibody comprising a framework region derived from a human antibody or a framework region variant thereof, and the framework region variant has reverse mutations of up to 10 amino acids in a light chain framework region and/or a heavy chain framework region of the human antibody; preferably, the framework region variant is selected from any one of the following (i) to (l):

(i) a framework region of the light chain variable region comprising an LCDR1, an LCDR2 and an LCDR3 having sequences set forth in SEQ ID NO: 18, SEQ ID NO: 19 and SEQ ID NO: 20, respectively, comprising one or more amino acid reverse mutations selected from the group consisting of 46P, 47W, 49Y, 70S and 71Y, and/or a framework region of the heavy chain variable region comprising an HCDR1 having a sequence set forth in SEQ ID NO: 15, an HCDR2 having a sequence set forth in SEQ ID NO: 16 or SEQ ID NO: 38 and an HCDR3 having a sequence set forth in SEQ ID NO: 17, comprising one or more amino acid reverse mutations selected from the group consisting of 38K and 46K;

(j) a framework region of the light chain variable region comprising an LCDR1, an LCDR2 and an LCDR3 having sequences set forth in SEQ ID NO: 24, SEQ ID NO: 25 and SEQ ID NO: 26, respectively, comprising one or more amino acid reverse mutations selected from the group consisting of 2V, 42G, 44V and 71Y, and/or a framework region of the heavy chain variable region comprising an HCDR1 having a sequence set forth in SEQ ID NO: 21, an HCDR2 having a sequence set forth in SEQ ID NO: 22 or SEQ ID NO: 47 and an HCDR3 having a sequence set forth in SEQ ID NO: 23, comprising one or more amino acid reverse mutations selected from the group consisting of 48I, 66K, 67A, 69L, 71V, 73K, 82F and 82A R;

(k) a framework region of the light chain variable region comprising an LCDR1, an LCDR2 and an LCDR3 having sequences set forth in SEQ ID NO: 30, SEQ ID NO: 31 and SEQ ID NO: 32, respectively, comprising one or more amino acid reverse mutations selected from the group consisting of 3V, 43P and 58V, and/or a framework region of the heavy chain variable region comprising an HCDR1, an HCDR2 and an HCDR3 having sequences set forth in SEQ ID NO: 27, SEQ ID NO: 28 and SEQ ID NO: 29, respectively, comprising one or more amino acid reverse mutations selected from the group consisting of 38K, 66K and 71V; and (l) a framework region of the light chain variable region comprising an LCDR1 having a sequence set forth in SEQ ID NO: 35, an LCDR2 having a sequence set forth in SEQ ID NO: 36 or SEQ ID NO: 64 and an LCDR3 having a sequence set forth in SEQ ID NO: 37, comprising one or more amino acid reverse mutations selected from the group consisting of 4V, 36Y, 43P, 47V, 49E, 70D and 871; and/or a framework region of the heavy chain variable region comprising an HCDR1 having a sequence set forth in SEQ ID NO: 33, an HCDR2 having a sequence set forth in SEQ ID NO: 16 or SEQ ID NO: 38 and an HCDR3 having a sequence set forth in SEQ ID NO: 34, comprising one or more amino acid reverse mutations selected from the group consisting of the group consisting of 2I, 38K and 46K;

wherein sites of the reverse mutations are numbered according to Kabat numbering scheme.

In some embodiments of the present disclosure, the anti-CEA antibody or the antigen-binding fragment thereof according to any one of the aforementioned embodiments in the antibody drug conjugate comprises a heavy chain constant region and a light chain constant region of the antibody; preferably, the heavy chain constant region is selected from the group consisting of human IgG1, IgG2, IgG3 and IgG4 constant regions, and the light chain constant region is selected from the group consisting of human antibody κ and λ chain constant regions; more preferably, the antibody comprises a heavy chain constant region having a sequence set forth in SEQ ID NO: 77 and a light chain constant region having a sequence set forth in SEQ ID NO: 78 or SEQ ID NO: 79;

most preferably, the anti-CEA antibody used in the present disclosure comprises:

(m) a heavy chain having a sequence set forth in SEQ ID NO: 80 or a sequence having at least 85% identity thereto, and/or a light chain having a sequence set forth in SEQ ID NO: 81 or a sequence having at least 85% identity thereto;

(n) a heavy chain having a sequence set forth in SEQ ID NO: 82 or a sequence having at least 85% identity thereto, and/or a light chain having a sequence set forth in SEQ ID NO: 83 or a sequence having at least 85% identity thereto;

(o) a heavy chain having a sequence set forth in SEQ ID NO: 84 or a sequence having at least 85% identity thereto, and/or a light chain having a sequence set forth in SEQ ID NO: 85 or a sequence having at least 85% identity thereto; or (p) a heavy chain having a sequence set forth in SEQ ID NO: 86 or a sequence having at least 85% identity thereto, and/or a light chain having a sequence set forth in SEQ ID NO: 87 or a sequence having at least 85% identity thereto.

In some embodiments of the present disclosure, the antigen-binding fragment according to any one of the aforementioned embodiments is selected from the group consisting of Fab, Fab', $F(ab')_2$, single-chain antibody (scFv), dimerized V region (diabody) and disulfide-stabilized V region (dsFv).

In some embodiments of the present disclosure, the antibody drug conjugate according to any one of the aforementioned embodiments is an antibody drug conjugate of general formula

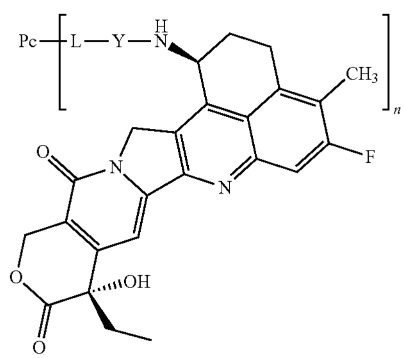

(Pc-L-Y-D)

wherein:

Y is selected from the group consisting of —O—$(CR^aR^b)_m$—$CR^1R^2$—C(O)—, —O—$CR^1R^2$—$(CR^aR^b)_m$—, —O—$CR^1R^2$—, —NH—$(CR^aR^b)_m$—$CR^1R^2$—C(O)— and —S—$(CR^aR^b)_m$—$CR^1R^2$—C(O)—;

$R^a$ and $R^b$ are identical or different and are each independently selected from the group consisting of hydrogen, deuterium, halogen, alkyl, haloalkyl, deuterated alkyl, alkoxy, hydroxy, amino, cyano, nitro, hydroxyalkyl, cycloalkyl and heterocyclyl; or, $R^a$ and $R^b$, together with carbon atoms connected thereto, form cycloalkyl and heterocyclyl;

$R^1$ is selected from the group consisting of halogen, haloalkyl, deuterated alkyl, cycloalkyl, cycloalkylalkyl, alkoxyalkyl, heterocyclyl, aryl and heteroaryl; $R^2$ is selected from the group consisting of hydrogen, halogen, haloalkyl, deuterated alkyl, cycloalkyl, cycloalkylalkyl, alkoxyalkyl, heterocyclyl, aryl and heteroaryl; or, $R^1$ and $R^2$, together with carbon atoms connected thereto, form cycloalkyl or heterocyclyl;

or, $R^a$ and $R^2$, together with carbon atoms connected thereto, form cycloalkyl or heterocyclyl;

m is an integer from 0 to 4;

n is a decimal or an integer from 1 to 10;

L is a linker unit;

Pc is the CEA antibody or the antigen-binding fragment thereof as described above.

In some embodiments of the present disclosure, in the antibody drug conjugate according to any one of the aforementioned embodiments, n is an integer or a decimal from 0 to 10, n may be a mean of 1, 2, 3, 4, 5, 6, 7, 8, 9 or 10, preferably 1 to 8, more preferably 2 to 8, and most preferably 4 to 6, and n is a mean of the decimal or the integer.

In some embodiments of the present disclosure, in the antibody drug conjugate according to any one of the aforementioned embodiments, n is a mean of a decimal or an integer from 3 to 5.

In some embodiments of the present disclosure, in the antibody drug conjugate according to any one of the aforementioned embodiments, n is a mean of a decimal or an integer from 6 to 7.

In some embodiments of the present disclosure, the antibody drug conjugate according to any one of the aforementioned embodiments is as shown in general formula (Pc-L-Y-D), wherein:

Y is —O—$(CR^aR^b)_m$—$CR^1R^2$—C(O)—;

$R^a$ and $R^b$ are identical or different and are each independently selected from the group consisting of hydrogen, deuterium, halogen and alkyl;

$R^1$ is haloalkyl or $C_3$-6 cycloalkyl;

$R^2$ is selected from the group consisting of hydrogen, haloalkyl and $C_{3-6}$ cycloalkyl;

or, $R^1$ and $R^2$, together with carbon atoms connected thereto, form $C_{3-6}$ cycloalkyl;

m is 0 or 1.

In some embodiments of the present disclosure, in the antibody drug conjugate according to any one of the aforementioned embodiments, Y is selected from the group consisting of:

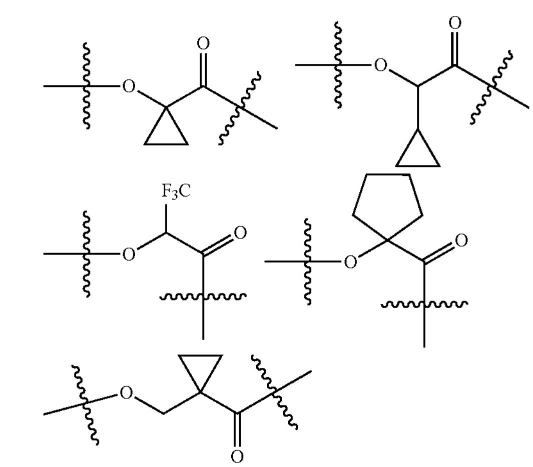

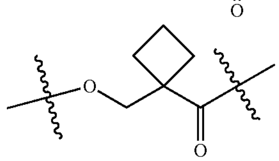

and

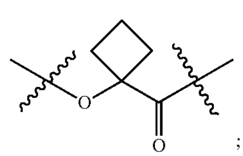

;

wherein the O terminus of Y is connected to the linker unit L.

In some embodiments of the present disclosure, in the antibody drug conjugate according to any one of the aforementioned embodiments, Y is:

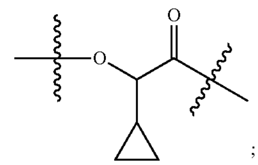 [SMILES: *OC(C(*)=O)C1CC1]

;

wherein the O terminus of Y is connected to the linker unit L.

In some embodiments of the present disclosure, the antibody drug conjugate according to any one of the aforementioned embodiments is selected from:

Pc-L-D

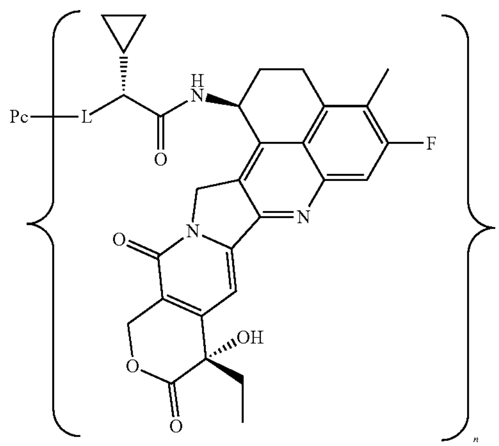

wherein:

L is a linker unit;

Pc is an anti-CEA antibody or an antigen-binding fragment thereof;

n is a decimal or an integer from 1 to 10.

In some embodiments of the present disclosure, the antibody drug conjugate according to any one of the aforementioned embodiments is selected from:

Pc-L-D

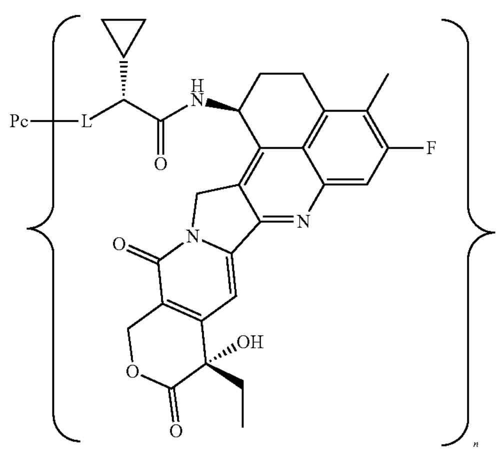

wherein:

L is a linker unit;

Pc is an anti-CEA antibody or an antigen-binding fragment thereof;

n is a decimal or an integer from 1 to 10.

In some embodiments of the present disclosure, in the antibody drug conjugate according to any one of the aforementioned embodiments, the linker unit -L- is $-L^1-L^2-L^3-L^4-$, wherein $L^1$ is selected from the group consisting of -(succinimidyl-3-yl-N)—W—C(O)—, —$CH_2$—C(O)—$NR^3$—W—C(O)— and —C(O)—W—C(O)—, wherein W is selected from the group consisting of $C_{1-8}$ alkyl, $C_{1-8}$ alkyl-cycloalkyl and linear heteroalkyl of 1 to 8 atoms, and the heteroalkyl comprises 1 to 3 heteroatoms selected from the group consisting of N, O and S, wherein the $C_{1-8}$ alkyl, cycloalkyl and linear heteroalkyl are each independently optionally further substituted with one or more substituents selected from the group consisting of halogen, hydroxy, cyano, amino, alkyl, chloroalkyl, deuterated alkyl, alkoxy and cycloalkyl;

$L^2$ is selected from the group consisting of —$NR^4(CH_2CH_2O)_{p}{}^1CH_2CH_2C(O)$—, —$NR^4(CH_2CH_2O)p^1CH_2C(O)$—, —$S(CH_2)p^1C(O)$— and a chemical bond, wherein $p^1$ is an integer from 1 to 20;

$L^3$ is a peptide residue consisting of 2 to 7 amino acids, wherein the amino acids are selected from amino acid residues formed from amino acids from phenylalanine, glycine, valine, lysine, citrulline, serine, glutamic acid and aspartic acid, and are optionally further substituted with one or more substituents selected from the group consisting of halogen, hydroxy, cyano, amino, alkyl, chloroalkyl, deuterated alkyl, alkoxy and cycloalkyl;

$L^4$ is selected from the group consisting of —$NR^5(CR^6R^7)_t$—, —$C(O)NR^5$, —$C(O)NR^5(CH_2)_t$— and a chemical bond, wherein t is an integer from 1 to 6;

$R^3$, $R^4$ and $R^5$ are identical or different and are each independently selected from the group consisting of hydrogen, alkyl, haloalkyl, deuterated alkyl and hydroxyalkyl;

$R^6$ and $R^7$ are identical or different and are each independently selected from the group consisting of hydrogen, halogen, alkyl, haloalkyl, deuterated alkyl and hydroxyalkyl.

In some embodiments, $L^1$ is selected from the group consisting of -(succinimidyl-3-yl-N)—W—C(O)—, —$CH_2$—C(O)—$NR^3$—W—C(O)— and —C(O)—W—C(O)—, wherein W is selected from the group consisting of $C_{1-8}$ alkyl, $C_{1-8}$ alkyl-$C_{3-6}$ cycloalkyl and linear heteroalkyl of 1 to 8 chain atoms, and the heteroalkyl comprises 1 to 3 heteroatoms selected from the group consisting of N, O and S, wherein the $C_{1-8}$ alkyl, $C_{1-8}$ alkyl-$C_3$-6 cycloalkyl or linear heteroalkyl of 1 to 8 chain atoms is independently optionally further substituted with one or more substituents selected from the group consisting of halogen, hydroxy, cyano, amino, alkyl, chloroalkyl, deuterated alkyl, alkoxy and cycloalkyl.

In some embodiments, $L^2$ is selected from the group consisting of —$NR^4(CH_2CH_2O)p^1CH_2CH_2C(O)$—, —$NR^4(CH_2CH_2O)p^1CH_2C(O)$—, —$S(CH_2)p^1C(O)$— and a chemical bond, wherein $p^1$ is an integer from 1 to 20.

In some embodiments, $L^3$ is a peptide residue consisting of 2 to 7 amino acids, wherein the amino acids are selected from the group consisting of amino acid residues formed from amino acids from phenylalanine, glycine, valine, lysine, citrulline, serine, glutamic acid and aspartic acid, and are optionally further substituted with one or more substituents selected from the group consisting of halogen, hydroxy, cyano, amino, alkyl, chloroalkyl, deuterated alkyl, alkoxy and cycloalkyl.

In some embodiments, $L^4$ is selected from the group consisting of —$NR^5(CR^6R^7)_t$—, —$C(O)NR^5$—, —$C(O)NR^5(CH_2)_t$— and a chemical bond, wherein t is an integer from 1 to 6.

In some embodiments, $R^3$, $R^4$ and $R^5$ are identical or different and are each independently selected from the group consisting of hydrogen, alkyl, haloalkyl, deuterated alkyl and hydroxyalkyl.

In some embodiments, $R^6$ and $R^7$ are identical or different and are each independently selected from the group consisting of hydrogen, halogen, alkyl, haloalkyl, deuterated alkyl and hydroxyalkyl.

In some embodiments of the present disclosure, in the antibody drug conjugate according to any one of the aforementioned embodiments, the linker unit -L- is $-L^1-L^2-L^3-L^4-$, wherein $L^1$ is

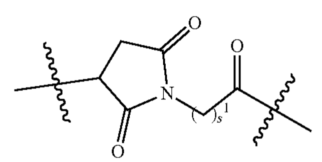

and $s^1$ is an integer from 2 to 8;

$L^2$ is a chemical bond;

$L^3$ is a tetrapeptide residue; preferably, $L^3$ is a tetrapeptide residue of glycine-glycine-phenylalanine-glycine (GGFG, SEQ ID NO: 92);

$L^4$ is —$NR^5(CR^6R^7)_t$—, wherein $R^5$, $R^6$ and $R^7$ are identical or different and are each independently hydrogen or alkyl, and t is 1 or 2;

wherein the $L^1$ terminus is connected to Pc, and the $L^4$ terminus is connected to Y.

In some embodiments of the present disclosure, the antibody drug conjugate according to any one of the aforementioned embodiments is as shown in general formula (Pc-L-Y-D) or general formula Pc-L-D, wherein -L- is:

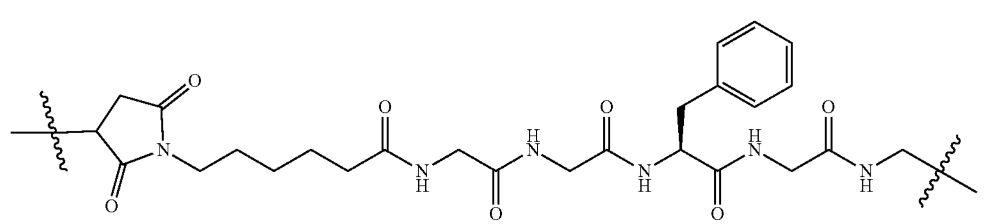

In some embodiments of the present disclosure, the antibody drug conjugate according to any one of the aforementioned embodiments is as shown in general formula (Pc-L-Y-D) or general formula Pc-L-D, wherein -L-Y— is optionally selected from the group consisting of:

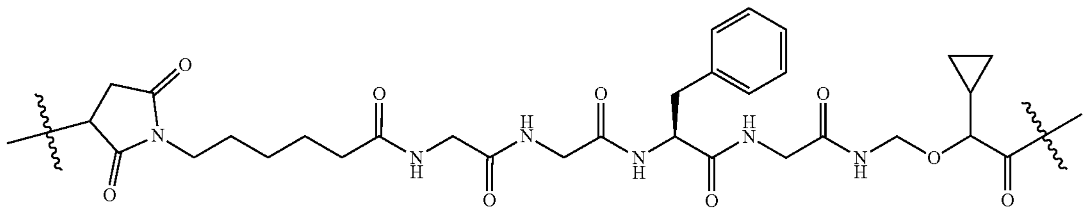

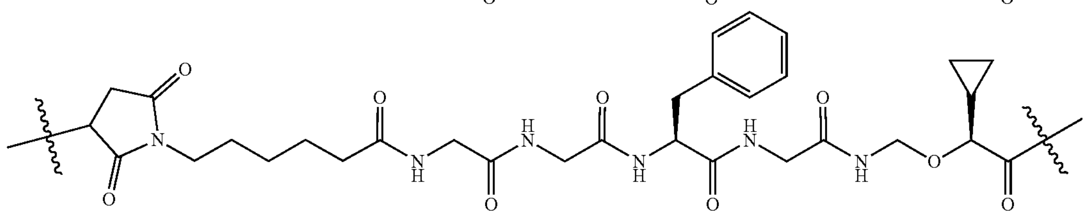

and

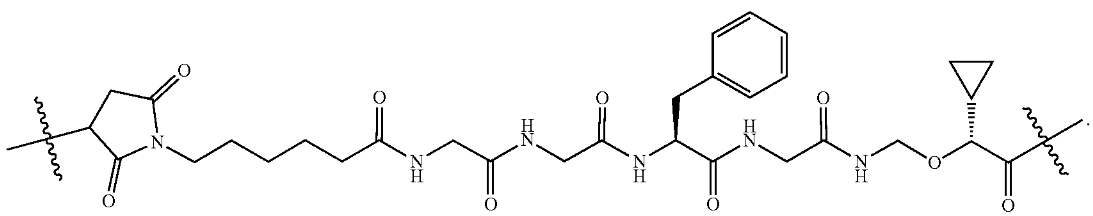

.

In some embodiments of the present disclosure, the antibody drug conjugate according to any one of the aforementioned embodiments is an antibody drug conjugate of general formula ($Pc-L_a-Y-D$):

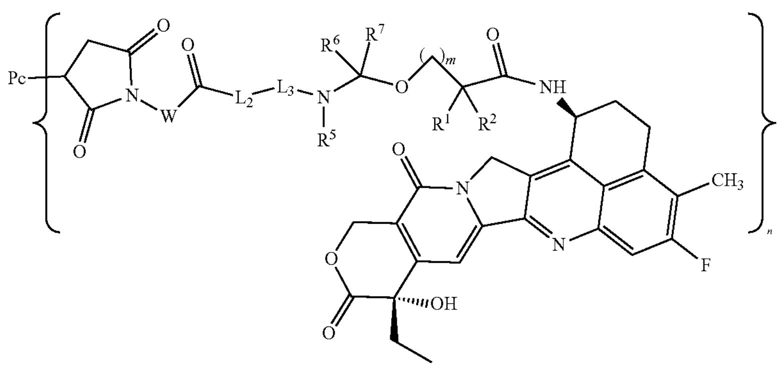

($Pc-L_a-Y-D$)

wherein:

W, $L^2$, $L^3$, $R^5$, $R^6$ and $R^7$ are as defined in the linker unit L;

Pc, n, $R^1$, $R^2$ and m are as defined in general formula (Pc-L-Y-D).

In some embodiments of the present disclosure, the antibody drug conjugate according to any one of the aforementioned embodiments is an antibody drug conjugate of general formula ($Pc-L_b-Y-D$):

Pc-$L_b$-Y-D
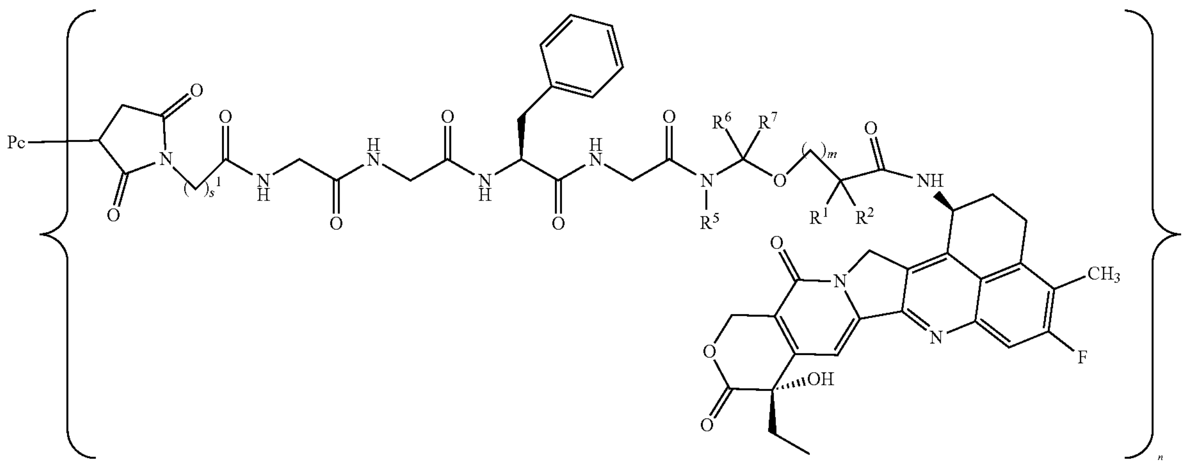
wherein:
$s^1$ is an integer from 2 to 8;
Pc, $R^1$, $R^2$, $R^5$-$R^7$, m and n are as defined in general formula (Pc-$L_a$-Y-D).
In some embodiments of the present disclosure, the antibody drug conjugate according to any one of the aforementioned embodiments is selected from the group consisting of:
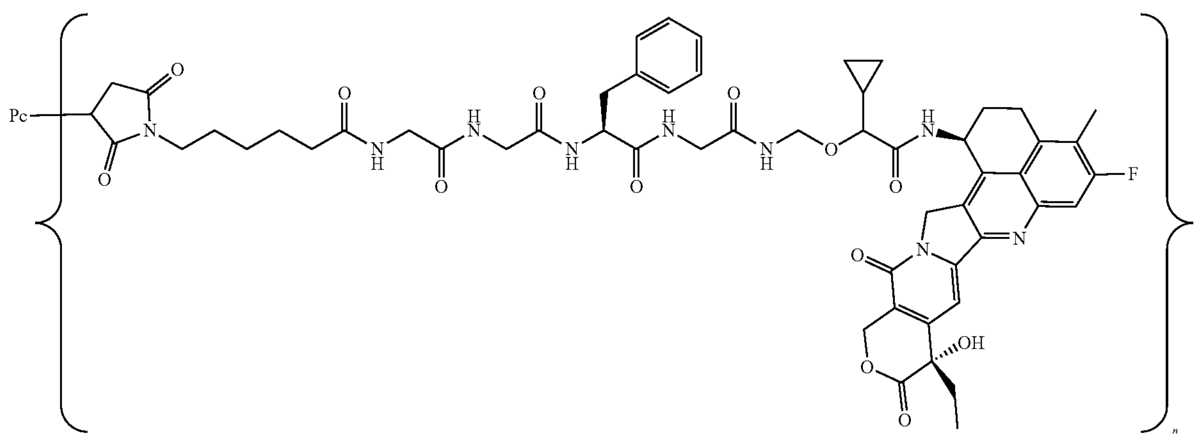
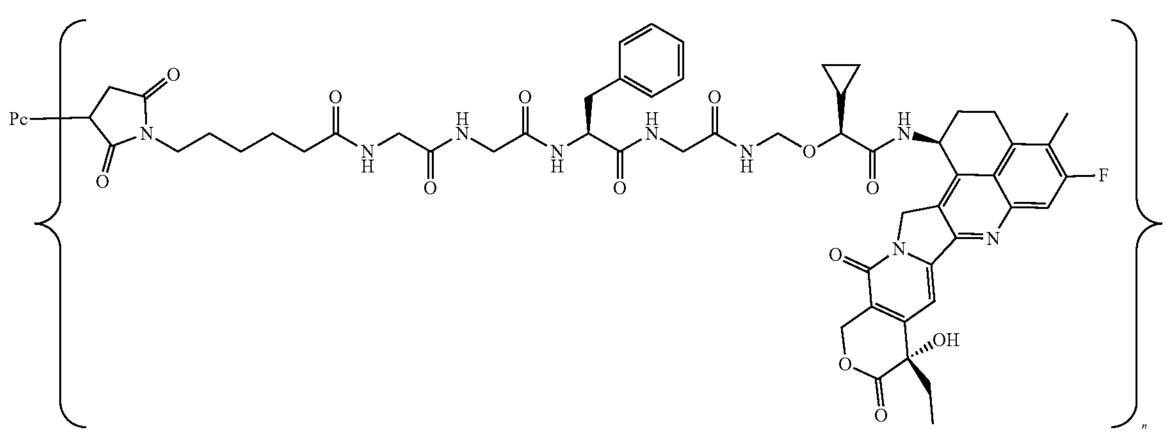
and -continued
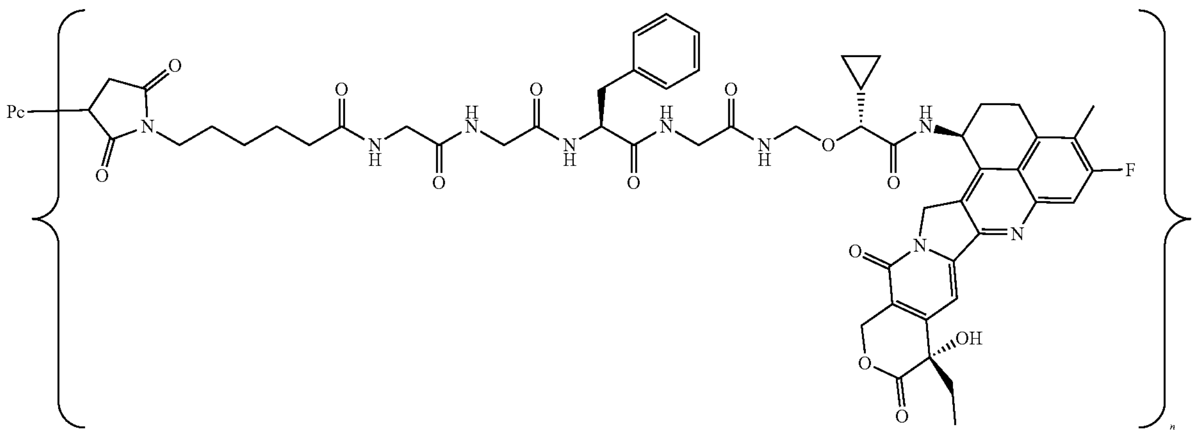
wherein Pc and n are as defined in general formula (Pc-L-Y-D).
In some embodiments of the present disclosure, the antibody drug conjugate is selected from the group consisting of:
Hu63-13-2-A
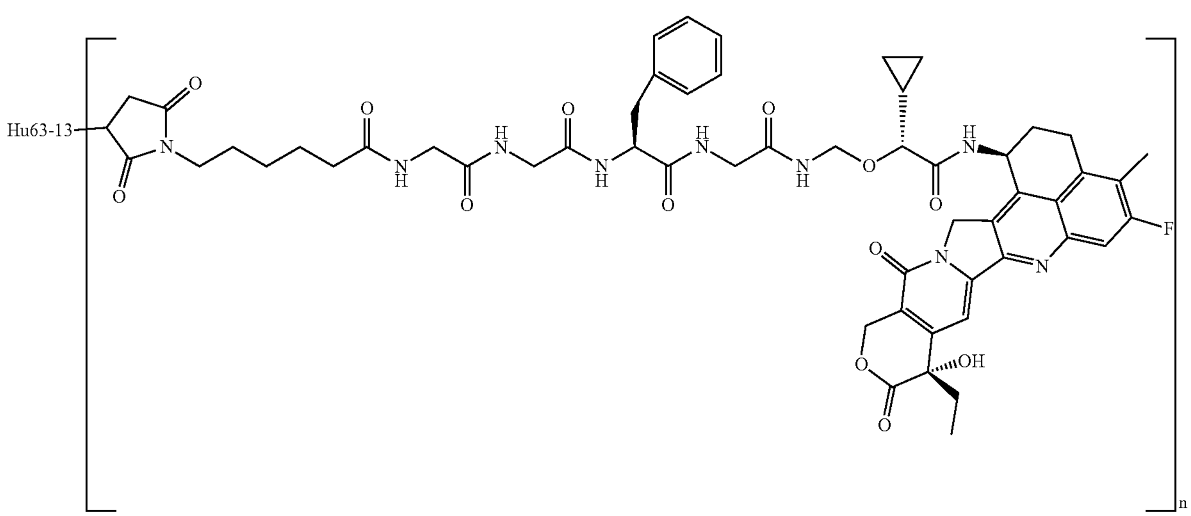

-continued
Hu47-14-2-A
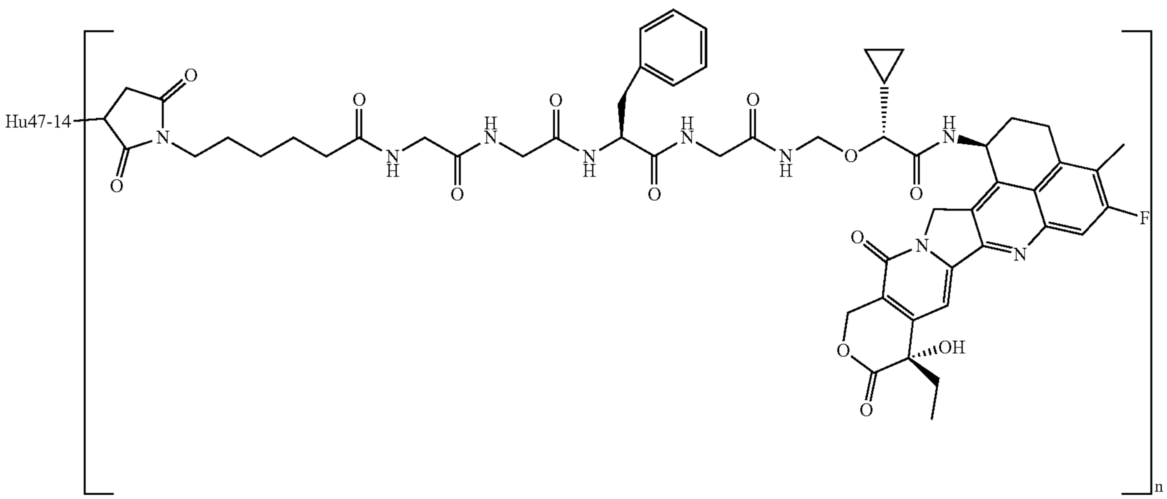
or
Hu67-14-2-A
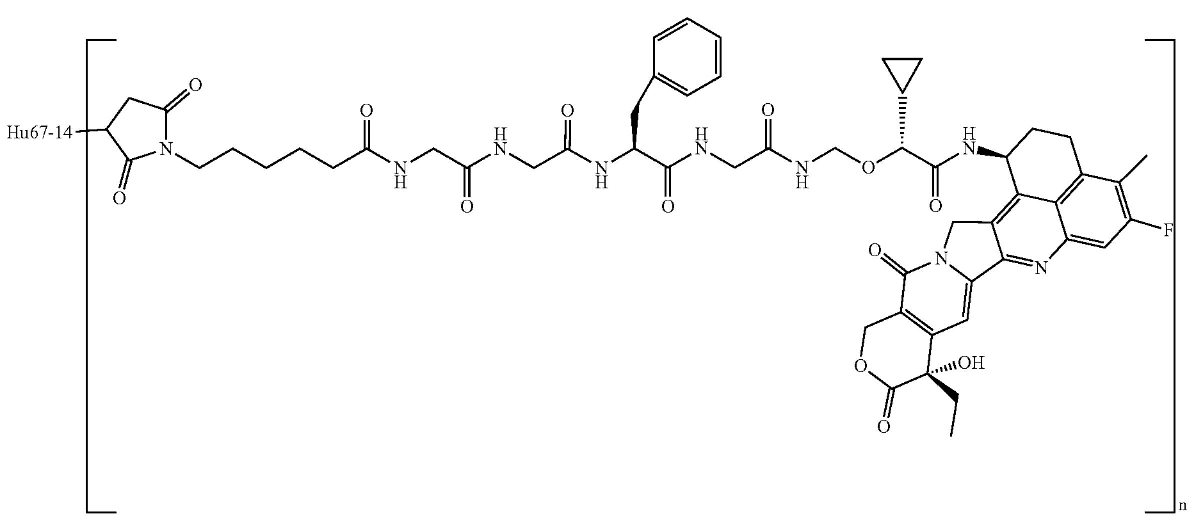

-continued

Hu103-32-2-A

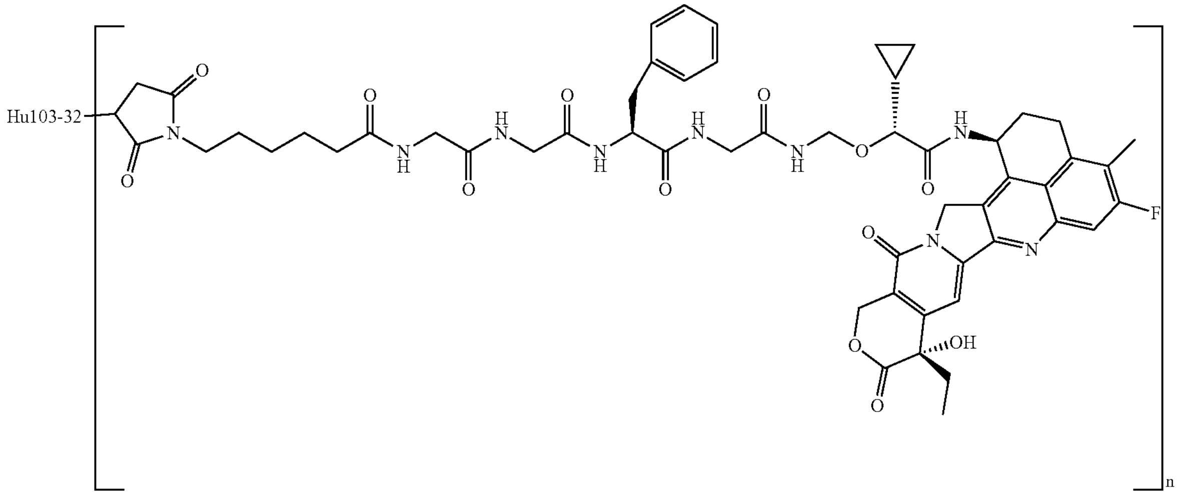

wherein n is as defined in general formula (Pc-L-Y-D);

the antibodies are described as follows:

Hu63-13 comprises a heavy chain having a sequence set forth in SEQ ID NO: 80, and a light chain having a sequence set forth in SEQ ID NO: 81;

Hu47-14 comprises a heavy chain having a sequence set forth in SEQ ID NO: 82, and a light chain having a sequence set forth in SEQ ID NO: 83;

Hu67-14 comprises a heavy chain having a sequence set forth in SEQ ID NO: 84, and a light chain having a sequence set forth in SEQ ID NO: 85;

Hu103-32 comprises a heavy chain having a sequence set forth in SEQ ID NO: 86, and a light chain having a sequence set forth in SEQ ID NO: 87.

Optionally, n may be a non-zero integer or a decimal from 0 to 10, preferably an integer or a decimal from 1 to 10; more preferably an integer or a decimal from 2 to 8; and most preferably an integer or a decimal from 3 to 8; optionally, n may be a decimal or an integer from 3 to 5; optionally, n is a decimal or an integer from 6 to 7.

The present disclosure further provides a method for preparing an antibody drug conjugate of general formula (Pc-$L_a$-Y-D), wherein the method comprises the following step:

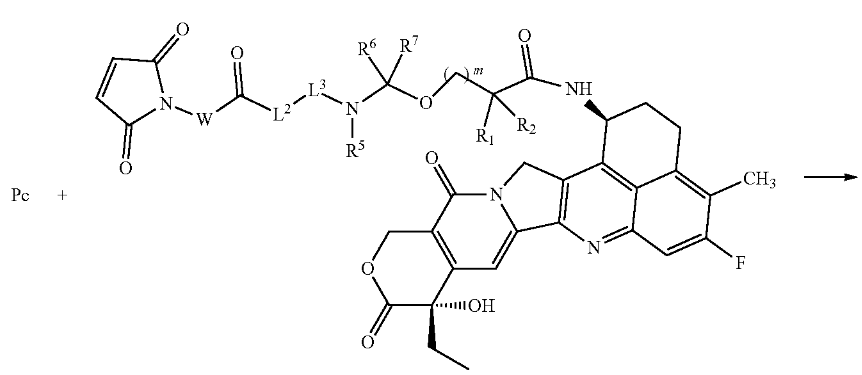

($L_a$-Y-D)

-continued

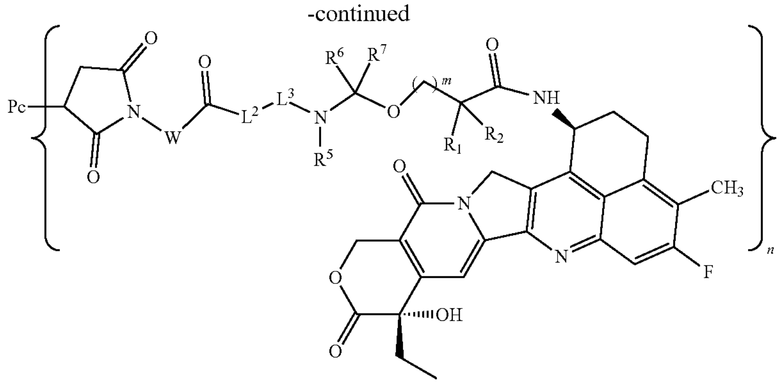

(Pc-$L_a$-Y-D)

subjecting reduced Pc and general formula ($L_a$-Y-D) to a coupling reaction to obtain a compound of general formula (Pc-$L_a$-Y-D); wherein:

Pc is an anti-CEA antibody or an antigen-binding fragment thereof;

W, $L^2$, $L^3$, $R^1$, $R^2$, $R^5$-$R^7$, m and n are as defined in general formula (Pc-$L_a$-Y-D).

The present disclosure further provides a method for preparing an antibody drug conjugate of general formula (Pc-L'-D), wherein the method comprises the following step:

subjecting reduced Pc and general formula (La'-D) to a coupling reaction to obtain a compound;

wherein:

Pc is the anti-CEA antibody or the antigen-binding fragment thereof as described above;

n is as defined in general formula (Pc-L-Y-D).

In another aspect, the present disclosure provides a pharmaceutical composition comprising the antibody drug conjugate according to any one of the aforementioned embodi-

L′-D

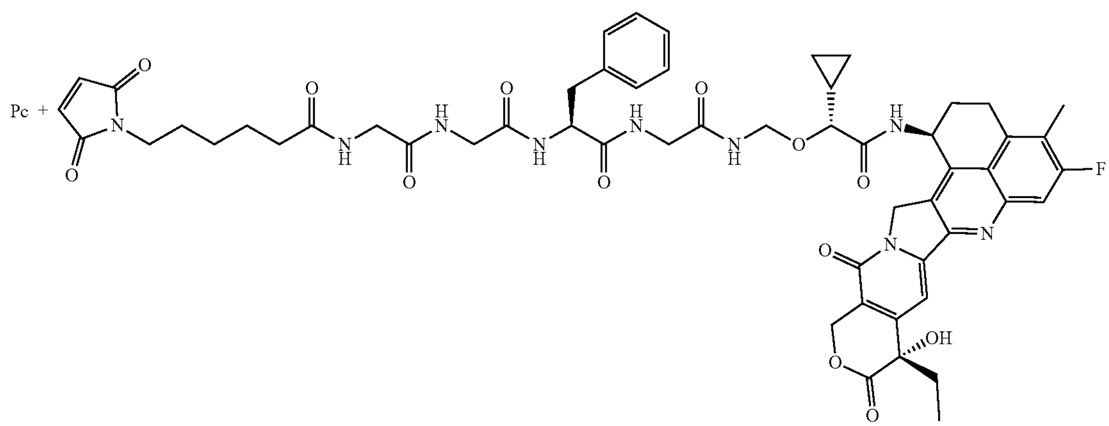

Pc-L′-D

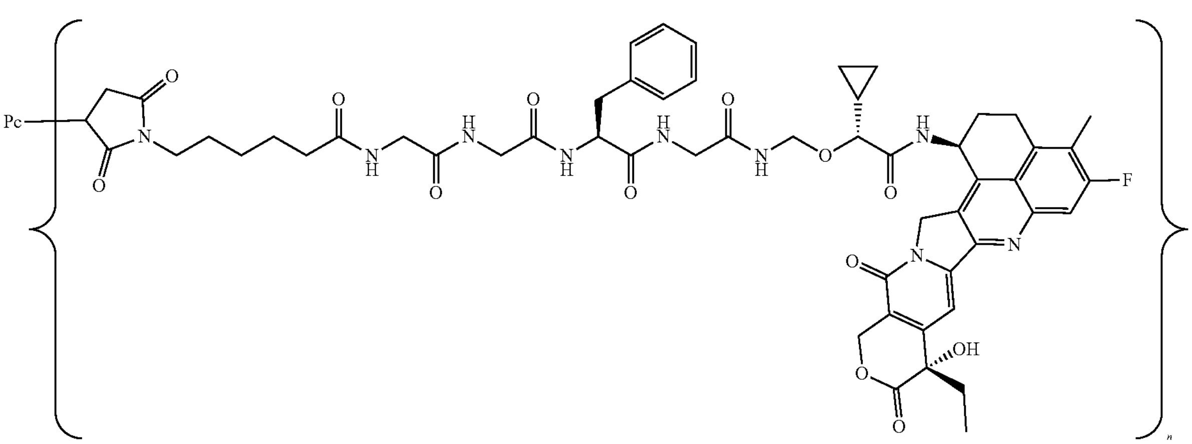

ments and one or more pharmaceutically acceptable excipients, diluents or carriers.

In another aspect, the present disclosure provides use of the antibody drug conjugate according to any one of the aforementioned embodiments or a pharmaceutical composition comprising the same as a medicament.

In another aspect, the present disclosure provides use of the antibody drug conjugate according to any one of the aforementioned embodiments or a pharmaceutical composition comprising the same in preparing a medicament for the treatment of a CEA-mediated disease or condition. The CEA-mediated disease or condition is a cancer with high CEA expression. Or, the CEA-mediated disease or condition is a cancer with moderate CEA expression.

In another aspect, the present disclosure provides use of the antibody drug conjugate according to any one of the aforementioned embodiments or a pharmaceutical composition comprising the same in preparing a medicament for the treatment or prevention of a tumor; wherein the tumor and cancer are preferably head and neck squamous cell carcinoma, head and neck cancer, brain cancer, neuroglioma, glioblastoma multiforme, neuroblastoma, central nervous system carcinoma, neuroendocrine tumor, throat cancer, nasopharyngeal cancer, esophageal cancer, thyroid cancer, malignant pleural mesothelioma, lung cancer, breast cancer, liver cancer, hepatobiliary cancer, pancreatic cancer, stomach cancer, gastrointestinal cancer, intestinal cancer, colon cancer, colorectal cancer, kidney cancer, clear cell renal cell carcinoma, ovarian cancer, endometrial cancer, cervical cancer, bladder cancer, prostate cancer, testicular cancer, skin cancer, melanoma, leukemia, lymphoma, bone cancer, chondrosarcoma, myeloma, multiple myeloma, myelodysplastic syndrome, Krukenberg tumor, myeloproliferative tumor, squamous cell carcinoma, Ewing's sarcoma, systemic light chain amyloidosis or Merkel cell carcinoma; more preferably, the lymphoma is selected from the group consisting of: Hodgkin's lymphoma, non-Hodgkin's lymphoma, diffuse large B-cell lymphoma, follicular lymphoma, primary mediastinal large B-cell lymphoma, mantle cell lymphoma, small lymphocytic lymphoma, large B-cell lymphoma rich in T-cells/histiocytes and lymphoplasmacytic lymphoma, the lung cancer is selected from non-small cell lung cancer or small cell lung cancer, and the leukemia is selected from the group consisting of: chronic myeloid leukemia, acute myeloid leukemia, lymphocytic leukemia, lymphoblastic leukemia, acute lymphoblastic leukemia, chronic lymphocytic leukemia and myeloid cell leukemia.

In another aspect, the present disclosure further relates to a method for treating and/or preventing a tumor, wherein the method comprises administering to a patient in need thereof a therapeutically effective dose of the antibody drug conjugate according to any one of the aforementioned embodiments or a pharmaceutical composition comprising the same; wherein the tumor is preferably a cancer associated with high CEA expression.

In another aspect, the present disclosure further relates to a method for treating or preventing a cancer, wherein the method comprises administering to a patient in need thereof a therapeutically effective dose of the antibody drug conjugate according to any one of the aforementioned embodiments or a pharmaceutical composition comprising the same; wherein the tumor and cancer are preferably head and neck squamous cell carcinoma, head and neck cancer, brain cancer, neuroglioma, glioblastoma multiforme, neuroblastoma, central nervous system carcinoma, neuroendocrine tumor, throat cancer, nasopharyngeal cancer, esophageal cancer, thyroid cancer, malignant pleural mesothelioma, lung cancer, breast cancer, liver cancer, hepatobiliary cancer, pancreatic cancer, stomach cancer, gastrointestinal cancer, intestinal cancer, colon cancer, colorectal cancer, kidney cancer, clear cell renal cell carcinoma, ovarian cancer, endometrial cancer, cervical cancer, bladder cancer, prostate cancer, testicular cancer, skin cancer, melanoma, leukemia, lymphoma, bone cancer, chondrosarcoma, myeloma, multiple myeloma, myelodysplastic syndrome, Krukenberg tumor, myeloproliferative tumor, squamous cell carcinoma, Ewing's sarcoma, systemic light chain amyloidosis or Merkel cell carcinoma; more preferably, the lymphoma is selected from the group consisting of: Hodgkin's lymphoma, non-Hodgkin's lymphoma, diffuse large B-cell lymphoma, follicular lymphoma, primary mediastinal large B-cell lymphoma, mantle cell lymphoma, small lymphocytic lymphoma, large B-cell lymphoma rich in T-cells/histiocytes and lymphoplasmacytic lymphoma, the lung cancer is selected from non-small cell lung cancer or small cell lung cancer, and the leukemia is selected from the group consisting of: chronic myeloid leukemia, acute myeloid leukemia, lymphocytic leukemia, lymphoblastic leukemia, acute lymphoblastic leukemia, chronic lymphocytic leukemia and myeloid cell leukemia.

The active compound (e.g., a ligand-drug conjugate according to the present disclosure, or a pharmaceutically acceptable salt thereof) may be formulated in a form suitable for administration by any suitable route, preferably in a form of a unit dose, or in a form of a single dose that can be self-administered by a subject. The unit dose of the present disclosure may be in a tablet, a capsule, a cachet, a vial, a powder, a granule, a lozenge, a suppository, a regenerating powder or a liquid formulation.

The administration dose of the active compound or composition used in the treatment method of the present disclosure will generally vary with the severity of the disease, the weight of the subject, and the efficacy of the active compound. However, as a general guide, a suitable unit dose may be 0.1 to 1000 mg.

The pharmaceutical composition of the present disclosure may comprise, in addition to the active compound, one or more excipients selected from the group consisting of: a filler, a diluent, a binder, a wetting agent, a disintegrating agent, an excipient and the like. Depending on the method of administration, the composition may comprise 0.1 to 99 wt. % of active compound.

The CEA antibody and the antibody drug conjugate provided by the present disclosure have good affinity for cell surface antigens, good endocytosis efficiency and high tumor inhibition efficiency as well as wider drug application windows, and are suitable for clinical drug application.

DETAILED DESCRIPTION

1. Terminology

Figure 1:
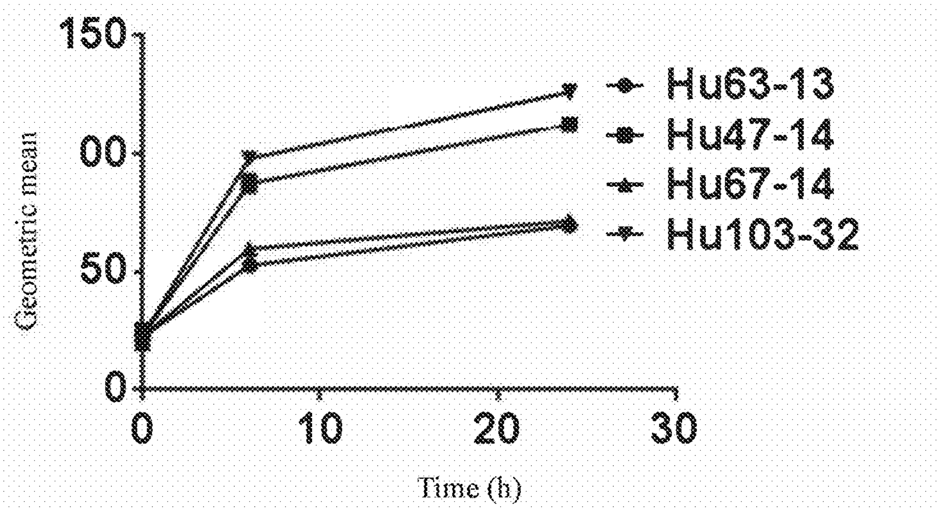
FIG. 1 shows the results of FACS detection of the binding of humanized antibodies to human CEA at the cellular level.

Unless defined otherwise, all technical and scientific terms used herein have the same meaning as commonly understood by those of ordinary skill in the art to which the present disclosure belongs. Although any methods and materials similar or equivalent to those described herein can also be used to implement or test the present disclosure, preferred methods and materials are described herein. In describing and claiming the present disclosure, the following terms are used in accordance with the definitions below.

When a trade name is used in the present disclosure, it is intended to include the formulation of the commercial product under the trade name, and the non-patent drug and active drug component of the commercial product under the trade name.

Unless otherwise stated, the terms used in the specification and claims have the following meanings.

The term “drug” refers to a chemical substance that can alter or ascertain an organism’s physiology and pathological state and can be used for the prevention, diagnosis and treatment of diseases. The drug includes a cytotoxic drug. There is no clear boundary between a drug and a toxic substance. The toxic substance refers to a chemical substance that has a toxic effect on organisms and can cause damage to human health even in small doses. Any drug in large doses may induce toxic responses.

The cytotoxic drug refers to a substance that inhibits or prevents cell functions and/or causes cell death or cell destruction. The cytotoxic drug can kill tumor cells in principle at a sufficiently high concentration; however, due to lack of specificity, the cytotoxic drug can cause apoptosis of normal cells while killing tumor cells, resulting in serious side effects. The cytotoxic drug includes toxins, such as small molecule toxins or enzymatically active toxins of bacterial, fungal, plant or animal origin, radioisotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), toxin drugs, chemotherapeutic drugs, antibiotics and nucleolytic enzymes.

The term “linker unit”, “linker” or “linker fragment” refers to a chemical structural fragment or bond, which is linked to a ligand at one end and linked to a drug at the other end, and also may be linked to other linkers and then linked to the drug.

The linker may comprise one or more linker components. Exemplary linker components include 6-maleimidocaproyl (“MC”), maleimidopropionyl (“MP”), valine-citrulline (“val-cit” or “vc”), alanine-phenylalanine (“ala-phe”), p-aminobenzyloxycarbonyl (“PAB”), N-succinimidyl 4-(2-pyridylthio)pentanoate (“SPP”), N-succinimidyl 4-(N-maleimidomethyl)cyclohexane-1 carboxylate (“SMCC”, also referred to herein as “MCC”), and N-succinimidyl(4-iodo-acetyl)aminobenzoate (“SIAB”). The linker may include extenders, spacers and amino acid units, and may be synthesized using methods known in the art, such as those described in US2005-0238649A1. The linker may be a “cleavable linker” favoring the release of drugs in cells. For example, acid-labile linkers (e.g., hydrazones), protease-sensitive (e.g., peptidase-sensitive) linkers, photolabile linkers, dimethyl linkers or disulfide-containing linkers can be used (Chari et al., *Cancer Research* 52: 127-131(1992); U.S. Pat. No. 5,208,020).

Abbreviations

Linker components include, but are not limited to:

MC=6-maleimidocaproyl, with a structure:

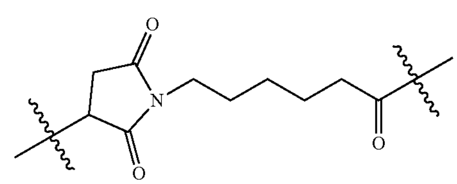
,

Val-Cit or “vc”=valine-citrulline (an exemplary dipeptide in a protease cleavable linker), citrulline=2-amino-5-ureidopentanoic acid, PAB=p-aminobenzyloxycarbonyl (an example of “self-immolative” linker components), Me-Val-Cit=N-methyl-valine-citrulline (where the linker peptide bond has been modified to prevent it from being cleaved by cathepsin B), MC(PEG)6-OH=maleimidocaproyl-polyethylene glycol (attachable to antibody cysteine), SPP=N-succinimidyl 4-(2-pyridylthio)valerate, SPDP=N-succinimidyl 3-(2-pyridyldithio)propionate, SMCC=succinimidyl-4-(N-maleimidomethyl)cyclohexane-1-carboxylate, IT=iminothiolane.

The term “antibody drug conjugate” means that an antibody is linked to a biologically active drug by a stable linking unit. In the present disclosure, “antibody drug conjugate” or antibody-drug conjugate (ADC) means that a monoclonal antibody or an antibody fragment is linked to a biologically active toxic drug by a stable linking unit. The antibody may be conjugated to the drug directly or via a linker. The mean number of drug modules conjugated to each antibody (the mean drug loading or the drug loading, which may be represented as n) may range, for example, from about 0 to about 20 drug modules; in certain embodiments, from 1 to about 10 drug modules; and in certain embodiments, from 1 to about 8 drug modules.

The term "mean drug loading" or "drug loading" refers to the mean number of cytotoxic drug loaded per ligand in antibody drug conjugate molecules, and may also be represented as the drug-to-antibody ratio. The drug loading may range from 0-12, preferably 1-10, cytotoxic drugs per ligand (Pc). In embodiments of the present disclosure, the drug loading is represented as n, which may also be referred to as a DAR (Drug-antibody Ratio) value, and exemplary values may be a mean of 1, 2, 3, 4, 5, 6, 7, 8, 9 and 10. The mean number of drugs per ADC molecule after coupling reactions can be characterized by conventional methods such as UV/visible spectroscopy, mass spectrometry, ELISA assays and HPLC.

The three-letter and single-letter codes for amino acids used in the present disclosure are as described in *J. biol. chem,* 243, p 3558 (1968).

The term "antibody" refers to an immunoglobulin, which is of a tetrapeptide chain structure formed by connection between two heavy chains and two light chains by interchain disulfide bonds. According to differences in the amino acid composition and the order of arrangement of the heavy chain constant regions, immunoglobulins can be divided into five classes, otherwise called isotypes of immunoglobulins, namely IgM, IgD, IgG, IgA and IgE, with their corresponding heavy chains being p chain, 6 chain, y chain, a chain and F chain, respectively. Ig of the same class can be divided into different subclasses according to differences in the amino acid composition of the hinge regions and the number and positions of disulfide bonds of the heavy chains; for example, IgG may be divided into IgG1, IgG2, IgG3 and IgG4. Light chains are classified into κ or λ chains by the differences in the constant regions. Each of the five classes of Ig may have a κ chain or λ chain.

In the heavy and light chains of full-length antibodies, the sequences of about 110 amino acids near the N-terminus vary considerably and thus are referred to as variable regions (Fv regions); the remaining amino acid sequences near the C-terminus are relatively stable and thus are referred to as constant regions. The variable regions comprise 3 hypervariable regions (HVRs) and 4 framework regions (FRs) with relatively conservative sequences. The 3 hypervariable regions determine the specificity of the antibody and thus are also known as complementarity determining regions (CDRs). Each light chain variable region (LCVR) or heavy chain variable region (HCVR) consists of 3 CDRs and 4 FRs arranged from the amino-terminus to the carboxy-terminus in the following order: FR1, CDR1, FR2, CDR2, FR3, CDR3 and FR4. The 3 CDRs of the light chain refer to LCDR1, LCDR2 and LCDR3, and the 3 CDRs of the heavy chain refer to HCDR1, HCDR2 and HCDR3.

The terms "fully humanized antibody", "fully human antibody" or "completely human antibody", also known as "fully humanized monoclonal antibody", has both humanized variable region and constant region so as to eliminate immunogenicity and toxic side effects. The development of monoclonal antibodies has four stages, namely murine monoclonal antibodies, chimeric monoclonal antibodies, humanized monoclonal antibodies and fully humanized monoclonal antibodies. Major relevant technologies for the preparation of fully human antibodies include: human hybridoma technology, EBV-transformed B-lymphocyte technology, phage display technology, transgenic mouse antibody preparation technology, single B-cell antibody preparation technology, and the like.

The term "antigen-binding fragment" refers to one or more fragments of an antibody that retain the ability to bind to an antigen. It is shown that a fragment of a full-length antibody can be used to perform the antigen-binding function of the antibody. The binding fragment included in the "antigen-binding fragment" is selected from the group consisting of Fab, Fab', $F(ab')_2$, single-chain antibody (scFv), dimerized V region (diabody), disulfide-stabilized V region (dsFv) and antigen-binding fragments of peptides comprising CDRs; examples include (i) Fab fragments, monovalent fragments consisting of VL, VH, CL and CH1 domains; (ii) $F(ab')_2$ fragments, bivalent fragments comprising two Fab fragments connected by disulfide bridges in the hinge regions; (iii) Fd fragments consisting of VH and CH1 domains; (iv) Fv fragments consisting of VH and VL domains of a single arm of an antibody; (v) single domains or dAb fragments (Ward et al., (1989) *Nature* 341: 544-546) consisting of VH domains; and (vi) isolated complementarity determining regions (CDRs) or (vii) combinations of two or more isolated CDRs which may optionally be linked by synthetic linkers. Furthermore, although the two domains of the Fv fragment, VL and VH, are encoded by separate genes, they can be linked by a synthetic linker by recombination, so that it is capable of producing a single protein chain in which the VL and VH regions pair to form a monovalent molecule (referred to as single-chain Fv (scFv); see, e.g., Bird et al. (1988) *Science* 242:423-426; and Huston et al. (1988) *Proc. Natl. Acad. Sci USA* 85:5879-5883). Such single-chain antibodies are also intended to be included in the term "antigen-binding fragment" of an antibody. Such antibody fragments are obtained using conventional techniques known to those skilled in the art, and screened for utility in the same manner as for intact antibodies. Antigen-binding portions may be produced using recombinant DNA technology or by enzymatic or chemical cleavage of intact immunoglobulins. Antibodies may be of different isotypes, e.g., IgG (e.g., subtype IgG1, IgG2, IgG3 or IgG4), IgA1, IgA2, IgD, IgE or IgM antibody.

In general, Fab is an antibody fragment having a molecular weight of about 50,000 and having antigen-binding activity, among fragments obtained by treating an IgG antibody molecule with a protease papain (e.g., cleaving the amino acid residue at position 224 of H chain), in which a portion on the N-terminal side of H chain is combined with L chain by a disulfide bond.

In general, F(ab')2 is an antibody fragment obtained by digesting a portion below the disulfide bond in the IgG hinge region with the enzyme pepsin. It has a molecular weight of about 100,000, has antigen-binding activity, and comprises two Fab regions linked at the hinge position.

In general, Fab' is an antibody fragment having a molecular weight of about 50,000 and having an antigen-binding activity, obtained by cleaving the disulfide bond in the hinge region of the $F(ab')_2$ described above.

In addition, Fab' may be produced by inserting DNA encoding the Fab' fragment into a prokaryotic or eukaryotic expression vector and introducing the vector into a prokaryote or a eukaryote to express the Fab'.

The term "single-chain antibody", "single-chain Fv" or "scFv" means a molecule comprising an antibody heavy chain variable domain (or VH) and an antibody light chain variable domain (or VL) linked by a linker. Such scFv molecules may have a general structure: NH2-VL-linker-VH—COOH or NH2-VH-linker-VL-COOH. Suitable linkers in the prior art consist of repeated GGGGS amino acid sequences or variants thereof, for example, 1-4 repeated variants (Holliger et al. (1993), *Proc. Natl. Acad. Sci. USA* 90:6444-6448). Other linkers that can be used in the present disclosure are described in Alfthan et al. (1995), *Protein Eng.* 8:725-731; Choi et al. (2001), *Eur. J Immunol.* 31:94-106; Hu et al. (1996), *Cancer Res.* 56:3055-3061, Kipriyanov et al. (1999), *J. Mol. Biol.* 293:41-56; and Roovers et al. (2001), *Cancer Immunol.*

The term "CDR" refers to one of the 6 hypervariable regions within the variable domain of an antibody which primarily contribute to antigen binding. In general, there are three CDRs (HCDR1, HCDR2 and HCDR3) in each heavy chain variable region and three CDRs (LCDR1, LCDR2 and LCDR3) in each light chain variable region. The amino acid sequence boundaries of the CDRs can be determined using any of a variety of well-known schemes. One of the most common definitions for the 6 CDRs is provided in Kabat E. A. et al., (1991) *Sequences of proteins of immunological interest*. NIH Publication 91-3242. As used herein, the Kabat definition of CDRs applies only to the CDR1, CDR2 and CDR3 of the light chain variable domain, and to the CDR2 and CDR3 of the heavy chain variable domain. Also included are the "Chothia" numbering scheme, the "ABM" numbering scheme, the "contact" numbering scheme (see Martin, ACR. *Protein Sequence and Structure Analysis of Antibody Variable Domains*[*J*]. 2001), the ImMunoGenTics (IMGT) numbering scheme (Lefranc M. P., *Dev. Comp. Immunol.*, 27, 55-77(2003)), and the like.

The term "antibody framework" refers to a portion of a variable domain VL or VH, which serves as a framework for the antigen-binding loops (CDRs) of the variable domain. It is essentially a variable domain without CDRs.

The term "epitope" or "antigenic determinant" refers to a site on an antigen to which an immunoglobulin or antibody binds. Epitopes generally comprise at least 3, 4, 5, 6, 7, 8, 9, 10, 11, 12, 13, 14 or 15 contiguous or non-contiguous amino acids in a unique spatial conformation, see, e.g., *Epitope Mapping Protocols in Methods in Molecular Biology*, Vol. 66, G. E. Morris, Ed. (1996).

The terms "specific binding", "selective binding", "selectively bind to" and "specifically bind to" refer to the binding of an antibody to an epitope on a predetermined antigen. In general, the antibody binds with an affinity (KD) of less than about $10^{-7}$ M, e.g., less than about $10^{-8}$ M, $10^{-9}$ M, or $10^{-10}$ M or less.

The term "KD" refers to the dissociation equilibrium constant for an antibody-antigen interaction. In general, the antibody (or antigen-binding fragment) of the present disclosure binds to CEA (or an epitope thereof) with a dissociation equilibrium constant (KD) of less than about $10^{-7}$ M, e.g., less than about $10^{-8}$ M or $10^{-9}$ M; for example, the KD value is determined using FACS method for the affinity of the antibody of the present disclosure for a cell surface antigen.

The term "compete", when used in a case where antigen-binding proteins (e.g., neutralizing antigen-binding proteins or neutralizing antibodies) compete for the same epitope, refers to the competition between the antigen-binding proteins assayed by the following assay in which an antigen-binding protein to be assayed (e.g., an antibody or an immunologically functional fragment thereof) prevents or inhibits (e.g., reduces) specific binding of a reference antigen-binding protein (e.g., a ligand or a reference antibody) to a common antigen (e.g., CEA antigen or a fragment thereof). Numerous types of competitive binding assays are available for determining whether an antigen-binding protein competes with another, such as solid phase direct or indirect radioimmunoassay (RIA), solid phase direct or indirect enzyme immunoassay (EIA) and sandwich competition assay (see, e.g., Stahli et al., 1983, *Methods in Enzymology* 9:242-253), solid phase direct biotin-avidin EIA (see, e.g., Kirkland et al., 1986, *J. Immunol.* 137:3614-3619), solid phase direct labeled assay and solid phase direct labeled sandwich assay (see, e.g., Harlow and Lane, 1988, *Antibodies, A Laboratory Manual*, Cold Spring Harbor Press), solid phase direct labeled RIA with I-125 label (see, e.g., Morel et al., 1988, *Molec. Immunol.* 25:7-15), solid phase direct biotin-avidin EIA (see, e.g., Cheung, et al, 1990, *Virology* 176:546-552) and direct labeled RIA (Moldenhauer et al, 1990, *Scand. J. Immunol.* 32:77-82). In general, the assay relates to a use of a purified antigen binding to a solid surface or a cell bearing any of an unlabeled assayed antigen-binding protein and a labeled reference antigen-binding protein. Competitive inhibition is measured by measuring the amount of label bound to the solid surface or the cell in the presence of the assayed antigen-binding protein. In general, the assayed antigen-binding protein is present in an excessive amount. Antigen-binding proteins identified by the competitive assay (competitive antigen-binding proteins) include: an antigen-binding protein binding to the same epitope as a reference antigen-binding protein, and an antigen-binding protein binding to an adjacent epitope sufficiently close to a binding epitope of the reference antigen-binding protein, and the two epitopes spatially interfere with each other to prevent the binding. Other detailed information regarding the method for assaying competitive binding is provided in the examples herein. In general, when the competitive antigen-binding protein exists in an excessive amount, the specific binding of the reference antigen-binding protein to the common antigen will be inhibited (such as reduced) by at least 40-45%, 45-50%, 50-55%, 55-60%, 60-65%, 65-70%, 70-75% or 75% or more. In some cases, the binding is inhibited by at least 80-85%, 85-90%, 90-95%, 95-97% or 97% or more.

The term "nucleic acid molecule" refers to a DNA molecule or an RNA molecule. The nucleic acid molecule may be single-stranded or double-stranded, but is preferably double-stranded DNA. A nucleic acid is "operably linked" when it is placed into a functional relationship with another nucleic acid sequence. For example, a promoter or enhancer is operably linked to a coding sequence if it affects the transcription of the coding sequence.

Amino acid sequence "identity" refers to the percentage of amino acid residues shared by a first sequence and a second sequence, wherein in aligning the amino acid sequences, gaps are introduced if necessary to achieve maximum percent sequence identity, and any conservative substitution is not considered as part of sequence identity. For the purpose of determining percent amino acid sequence identity, alignments can be achieved in a variety of ways that are within the skill in the art, for example, using publicly available computer software such as BLAST, BLAST-2, ALIGN, ALIGN-2 or Megalign (DNASTAR) software. Those skilled in the art can determine parameters suitable for measuring alignment, including any algorithms required to achieve maximum alignment of the full length of the aligned sequences.

The term "expression vector" refers to a nucleic acid molecule capable of transporting another nucleic acid to which it has been linked. In one embodiment, the vector is a "plasmid" that refers to a circular double-stranded DNA loop into which additional DNA segments can be ligated. In another embodiment, the vector is a viral vector, wherein additional DNA segments may be ligated into the viral genome. The vectors disclosed herein are capable of autonomously replicating in a host cell into which they are introduced (e.g., bacterial vectors having a bacterial origin of replication and episomal mammalian vectors) or capable of integrating into the genome of a host cell after being introduced into the host cell and thus replicating with the host genome (e.g., non-episomal mammalian vectors).

Methods of producing and purifying antibodies and antigen-binding fragments are well known in the art, for example, those described in chapters 5-8 and 15 of *Antibodies: A Laboratory Manual*, Cold Spring Harbor Press. Antigen-binding fragments can likewise be prepared using conventional methods. The antibody or antigen-binding fragment described in the present invention is genetically engineered to contain one or more additional human FR regions in the non-human CDR regions. Human FR germline sequences can be obtained at the website http://imgt.cines.fr of ImMunoGeneTics (IMGT) or from the immunoglobulin journal, Lefranc, G., *the Immunoglobulin FactsBook*, Academic Press, 2001ISBN012441351, by comparing the IMGT human antibody variable region germline gene database with the MOE software.

The term "host cell" refers to a cell into which an expression vector has been introduced. Host cells may include bacterial, microbial, plant or animal cells. Bacteria susceptible to transformation include members of the Enterobacteriaceae family, such as strains of *Escherichia coli* or *Salmonella*; members of the Bacillaceae family, such as *Bacillus subtilis*; Pneumococcus; *Streptococcus* and *Haemophilus influenzae*. Suitable microorganisms include *Saccharomyces cerevisiae* and *Pichia pastoris*. Suitable animal host cell lines include CHO (Chinese hamster ovary cell line) and NS0 cells.

The engineered antibody or the antigen-binding fragment of the present disclosure can be prepared and purified using conventional methods. For example, cDNA sequences encoding the heavy and light chains can be cloned and recombined into an expression vector. Recombinant immunoglobulin expression vectors can be stably transfected into host cells. As a more recommended prior art, mammalian expression systems will result in glycosylation of the antibody, particularly at the N-terminal site of the Fc region. Positive clones are expanded in a medium in a bioreactor to produce antibodies. The culture with the secreted antibody can be purified using conventional techniques, for example, using an A or G Sepharose FF column. Nonspecifically bound fractions are washed away. The bound antibody is eluted using pH gradient method, and the antibody fragments are detected using SDS-PAGE and collected. The antibody can be filtered and concentrated using conventional methods. Soluble mixtures and polymers can also be removed using conventional methods, such as molecular sieves and ion exchange. The resulting product needs to be immediately frozen, e.g., at −70° C., or lyophilized.

The term "peptide" refers to a compound fragment between an amino acid and a protein. It is formed by connecting 2 or more amino acid molecules by peptide bonds, and is a structural and functional fragment of the protein.

The term "sugar" refers to biomacromolecules consisting of C, H and O elements. They can be classified into monosaccharides, disaccharides, polysaccharides and the like.

The term "alkyl" refers to a saturated aliphatic hydrocarbon group that is a linear or branched group containing 1 to 20 carbon atoms, preferably alkyl containing 1 to 12 carbon atoms, more preferably alkyl containing 1 to 10 carbon atoms, and most preferably alkyl containing 1 to 6 carbon atoms (containing 1, 2, 3, 4, 5 or 6 carbon atoms). Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various side-chain isomers thereof, and the like. More preferred is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. Alkyl may be substituted or unsubstituted. When substituted, the substituent may be substituted at any available connection site, wherein the substituent is preferably one or more of the following groups independently selected from the group consisting of alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio, heterocycloalkylthio and oxo.

The term "heteroalkyl" refers to alkyl containing one or more heteroatoms selected from the group consisting of N, O and S, wherein the alkyl is as defined above.

The term "alkylene" refers to a saturated linear or branched aliphatic hydrocarbon group having 2 residues derived from the parent alkane by removal of two hydrogen atoms from the same carbon atom or two different carbon atoms. It is a linear or branched group containing 1 to 20 carbon atoms, preferably alkylene containing 1 to 12 carbon atoms, more preferably alkylene containing 1 to 6 carbon atoms (containing 1, 2, 3, 4, 5 or 6 carbon atoms). Non-limiting examples of alkylene include, but are not limited to, methylene($-CH_2-$), 1,1-ethylidene($-CH(CH_3)-$), 1,2-ethylidene($-CH_2CH_2)-$, 1,1-propylidene($-CH(CH_2CH_3)-$), 1,2-propylidene($-CH_2CH(CH_3)-$), 1,3-propylidene($-CH_2CH_2CH_2-$), 1,4-butylidene($-CH_2CH_2CH_2CH_2-$), 1,5-butylidene($-CH_2CH_2CH_2CH_2CH_2-$) and the like. The alkylene may be substituted or unsubstituted. When substituted, the substituent may be substituted at any available connection site with one or more substituents preferably independently optionally selected from the group consisting of alkyl, alkenyl, alkynyl, alkoxy, alkylthio, alkylamino, halogen, mercapto, hydroxy, nitro, cyano, cycloalkyl, heterocyclyl, aryl, heteroaryl, cycloalkoxy, heterocycloalkoxy, cycloalkylthio, heterocycloalkylthio and oxo.

The term "alkoxy" refers to —O-(alkyl) and —O-(unsubstituted cycloalkyl), wherein the alkyl or cycloalkyl is as defined above. Non-limiting examples of alkoxy include: methoxy, ethoxy, propoxy, butoxy, cyclopropyloxy, cyclobutoxy, cyclopentyloxy and cyclohexyloxy. Alkoxy may be optionally substituted or unsubstituted, and when it is substituted, the substituent is preferably one or more of the following groups independently selected from the group consisting of: alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio and heterocycloalkylthio.

The term "haloalkyl" refers to an alkyl group in which the hydrogen is substituted with one or more halogens, wherein the alkyl is as defined above.

The term "deuterated alkyl" refers to an alkyl group in which the hydrogen is substituted with one or more deuterium atoms, wherein the alkyl is as defined above.

The term "hydroxyalkyl" refers to an alkyl group in which the hydrogen is substituted with one or more hydroxy groups, wherein the alkyl is as defined above.

The term "hydroxy" refers to —OH group.

The term "halogen" refers to fluorine, chlorine, bromine or iodine.

The term "amino" refers to $—NH_2$.

The term "nitro" refers to $—NO_2$.

The term "cyano" refers to —CN.

The present disclosure also comprises various deuterated forms of the compounds of formula (I). Each available hydrogen atom connected to a carbon atom may be independently substituted with a deuterium atom. Those skilled in the art are able to synthesize the compounds of formula (I) in deuterated form with reference to the relevant literature. Commercially available deuterated starting materials can be used in preparing the deuterated forms of the compounds of formula (I), or they can be synthesized using conventional techniques with deuterated reagents including, but not limited to, deuterated borane, tri-deuterated borane in tetrahydrofuran, deuterated lithium aluminum hydride, deuterated iodoethane, deuterated iodomethane, and the like.

The term "optional" or "optionally" means that the event or circumstance subsequently described may, but not necessarily, occur, and that the description includes instances where the event or circumstance occurs or does not occur. For example, "a heterocyclyl group optionally substituted with alkyl" means that alkyl may be, but not necessarily, present, and that the description includes instances where the heterocyclyl group is or is not substituted with alkyl.

The term "substituted" means that one or more, preferably up to 5, more preferably 1, 2 or 3 hydrogen atoms in the group are independently substituted with a substituent. A substituent is only in its possible chemical position, and those skilled in the art will be able to determine (experimentally or theoretically) possible or impossible substitution without undue efforts. For example, it may be unstable when amino or hydroxy having a free hydrogen is bound to a carbon atom having an unsaturated (e.g., olefinic) bond.

The term "pharmaceutical composition" refers to a mixture containing one or more of the compounds described herein or a physiologically/pharmaceutically acceptable salt or pro-drug thereof, and other chemical components, for example physiologically/pharmaceutically acceptable carriers and excipients. The purpose of the pharmaceutical composition is to promote the administration to an organism, which facilitates the absorption of the active ingredient, thereby exerting biological activities.

The term "pharmaceutically acceptable salt" refers to a salt of the antibody drug conjugates of the present disclosure, or a salt of the active compound described in the present disclosure. Such salts are safe and effective when used in a subject and possess the required biological activity. The ligand drug conjugate of the present disclosure at least comprises one amino group and thus may form a salt with an acid. Non-limiting examples of pharmaceutically acceptable salts include: hydrochloride, hydrobromide, hydriodate, sulphate, bisulfate, citrate, acetate, succinate, ascorbate, oxalate, nitrate, sorbate, hydrophosphate, dihydrophosphate, salicylate, hydrocitrate, tartrate, maleate, fumarate, formate, benzoate, mesylate, ethanesulfonate, benzenesulphonate and p-toluenesulfonate.

In one embodiment of the present disclosure, the cytotoxic drug is conjugated to a mercapto group of the antibody by a linker unit.

The loading of the ligand cytotoxic drug conjugate can be controlled by the following non-limiting methods, including:

(1) controlling a molar ratio of a linking reagent to a monoclonal antibody, (2) controlling reaction time and temperature, and (3) selecting different reagents.

For preparation of conventional pharmaceutical compositions, reference is made to Chinese Pharmacopoeia.

The term "pharmaceutically acceptable carrier" for the drug of the present disclosure refers to a system that can alters the manner in which the drug gets into a subject and the distribution of the drug in the subject, controls the release rate of the drug, and delivers the drug to a targeted organ. The drug carrier release and targeted system can reduce drug degradation and loss, reduce side effects and improve bioavailability. For example, polymeric surfactants that can be used as carriers can self-assemble due to their unique amphiphilic structures to form various forms of aggregates, such as micelles, microemulsions, gels, liquid crystals and vesicles, as preferred examples. The aggregates have the capability of encapsulating drug molecules and have good permeability for membranes, and therefore can be used as excellent drug carriers.

The term "excipient" is an addition, apart from the active compound, to a pharmaceutical composition. It may also be referred to as an adjuvant. For example, binders, fillers, disintegrants, lubricants in tablets; base part in semisolid ointment and cream preparations; preservatives, antioxidants, corrigents, fragrances, cosolvents, emulsifiers, solubilizers, tonicity adjusting agents, colorants and the like in liquid formulations can all be referred to as excipients.

The term "diluent", also referred to as a filler, is used primarily to increase the weight and volume of the tablet. The addition of the diluent not only ensures a certain volume, but also reduces the dose deviation of the main ingredients, and improves the drug's compression moldability and the like. When the drug in tablet form contains oily components, an absorbent is necessarily added to absorb the oily components so as to maintain a "dry" state and thus to facilitate the preparation of the tablet. Examples include starch, lactose, inorganic salts of calcium, microcrystalline cellulose and the like.

The pharmaceutical composition may be in the form of a sterile injectable aqueous solution. Available and acceptable vehicles or solvents include water, Ringer's solution and isotonic sodium chloride solution. The sterile injectable formulation may be a sterile injectable oil-in-water microemulsion in which the active ingredient is dissolved in the oil phase. For example, the active ingredient is dissolved in a mixture of soybean oil and lecithin. The oil solution is then added to a mixture of water and glycerol and treated to form a microemulsion. The injection or microemulsion can be locally injected into the bloodstream of a subject in large quantities. Alternatively, it may be desirable to administer the solution and microemulsion in such a way as to maintain a constant circulating concentration of the compound of the present disclosure. To maintain such a constant concentration, a continuous intravenous delivery device may be used. An example of such a device is a Deltec CADD-PLUS™ 5400 intravenous injection pump.

The pharmaceutical composition may be in the form of a sterile injectable aqueous or oily suspension for intramuscular and subcutaneous administration. The suspension can be prepared according to the prior art using those suitable dispersants or wetting agents and suspending agents mentioned above. The sterile injectable formulation may also be a sterile injection or suspension prepared in a parenterally acceptable non-toxic diluent or solvent, e.g., a solution prepared in 1,3-butanediol. In addition, a sterile fixed oil may be conventionally used as a solvent or a suspending medium. For this purpose, any blend fixed oil including synthetic monoglycerides or diglycerides can be used. In addition, fatty acids such as oleic acid may also be used in the preparation of injections.

The present disclosure relates to a cleavable linking arm with a specific structure, an active substance with a specific structure, and an antibody drug conjugate (ADC) consisting of the linking arm, the active substance and an antibody. Such an ADC is a complex formed by linking a toxic substance to an antibody via a spacer. The antibody drug conjugate (ADC) is degraded in vivo to release active molecules, thereby playing an anti-tumor role.

2. Synthesis Method

For the synthesis purpose, the following technical schemes for synthesis are adopted.

A method for preparing a compound of general formula (Pc-$L_a$-Y-D) comprises the following steps:

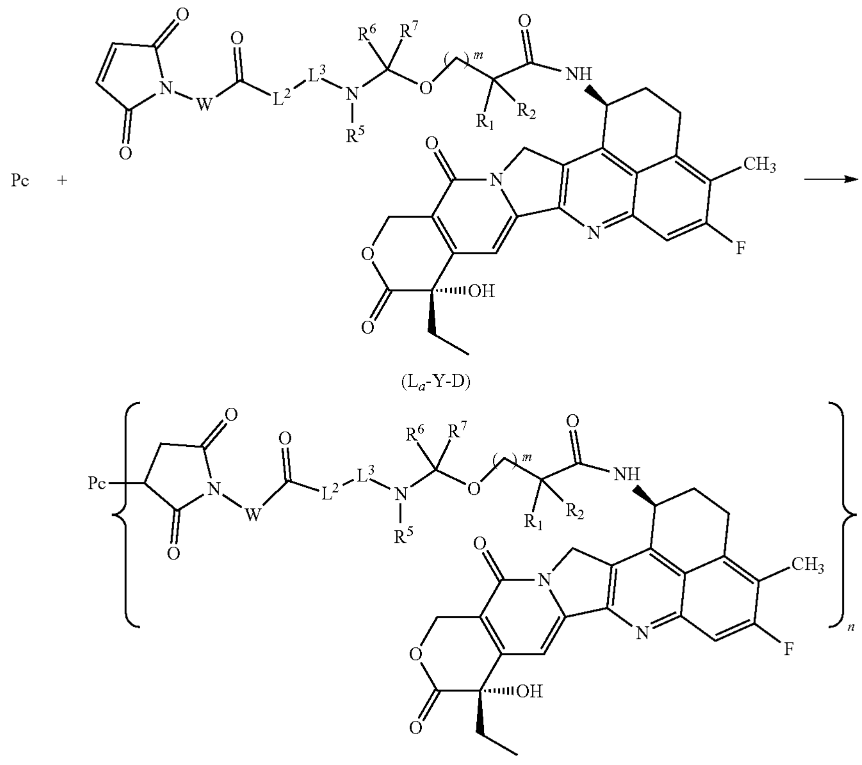

($L_a$-Y-D)

(Pc-$L_a$-Y-D)

subjecting reduced Pc and general formula ($L_a$-Y-D) to a coupling reaction to give a compound of general formula (Pc-$L_a$-Y-D), wherein the reducing agent is preferably TCEP; particularly, the disulfide bonds in the antibody are preferably reduced;

wherein:

Pc, W, $L^2$, $L^3$, $R^1$, $R^2$, $R^5$-$R^7$, m and n are as defined in general formula (Pc-$L_a$-Y-D).

One or more embodiments of the present disclosure are described in detail in the specification above. Although any methods and materials similar or identical to those described herein can also be used to implement or test the present disclosure, preferred methods and materials are described below. Other features, objects and advantages of the present disclosure will be apparent from the description and the claims. In the specification and claims, singular forms include plural referents unless otherwise indicated clearly in the context. Unless otherwise defined, all technical and scientific terms used herein have the meanings generally understood by those of ordinary skill in the art to which the present disclosure belongs. All the patents and publications cited in the specification are incorporated by reference. The following examples are set forth in order to more fully illustrate the preferred embodiments of the present disclosure. These examples should not be construed in any way as limiting the scope of the present disclosure that is defined by the claims.

Example 1: Preparation of CEA Recombinant Protein and Stably Transfected Cell I. Sequences of Recombinant CEA Antigen and CEA Protein Expressed on Cell Surface The amino acid sequences of the human CEA with Fc and His tags were cloned into mammalian cell expression vectors, and recombinant protein was obtained after expression and purification in 293E cells and then was used in experiments of subsequent examples. Meanwhile, the human CEA gene without a label, the human CEACAM1 gene and the monkey CEA gene were transfected into CHO cells to form a CHO cell strain expressing CEA protein on the cell surfaces for the subsequent screening and identification of antibodies. Amino acid sequences of the related proteins are as follows:

1. Amino Acid Sequence of Human CEA-his (hCEA-his):

(SEQ ID NO: 1)

```
KLTIESTPFNVAEGKEVLLLVHNLPQHLFGYSWYKGERVDGNRQIIGYVI
GTQQATPGPAYSGREIIYPNASLLIQNIIQNDTGFYTLHVIKSDLVNEEA
TGQFRVYPELPKPSISSNNSKPVEDKDAVAFTCEPETQDATYLWWVNNQS
LPVSPRLQLSNGNRTLTLFNVTRNDTASYKCETQNPVSARRSDSVILNVL
YGPDAPTISPLNTSYRSGENLNLSCHAASNPPAQYSWFVNGTFQQSTQEL
FIPNITVNNSGSYTCQAHNSDTGLNRTTVTTITVYAEPPKPFITSNNSNP
VEDEDAVALTCEPEIQNTTYLWWVNNQSLPVSPRLQLSNDNRTLTLLSVT
RNDVGPYECGIQNELSVDHSDPVILNVLYGPDDPTISPSYTYYRPGVNLS
LSCHAASNPPAQYSWLIDGNIQQHTQELFISNITEKNSGLYTCQANNSAS
GHSRTTVKTITVSAELPKPSISSNNSKPVEDKDAVAFTCEPEAQNTTYLW
WVNGQSLPVSPRLQLSNGNRTLTLFNVTRNDARAYVCGIQNSVSANRSDP
VTLDVLYGPDTPIISPPDSSYLSGANLNLSCHSASNPSPQYSWRINGIPQ
QHTQVLFIAKITPNNNGTYACFVSNLATGRNNSIVKSITVSASGTSPGLS
AHHHHHH
```

2. Amino Acid Sequence of Human CEA-Fc (hCEA-Fc):

(SEQ ID NO: 2)

```
KLTIESTPFNVAEGKEVLLLVHNLPQHLFGYSWYKGERVDGNRQIIGYVI
GTQQATPGPAYSGREIIYPNASLLIQNIIQNDTGFYTLHVIKSDLVNEEA
TGQFRVYPELPKPSISSNNSKPVEDKDAVAFTCEPETQDATYLWWVNNQS
LPVSPRLQLSNGNRTLTLFNVTRNDTASYKCETQNPVSARRSDSVILNVL
YGPDAPTISPLNTSYRSGENLNLSCHAASNPPAQYSWFVNGTFQQSTQEL
FIPNITVNNSGSYTCQAHNSDTGLNRTTVTTITVYAEPPKPFITSNNSNP
VEDEDAVALTCEPEIQNTTYLWWVNNQSLPVSPRLQLSNDNRTLTLLSVT
RNDVGPYECGIQNELSVDHSDPVILNVLYGPDDPTISPSYTYYRPGVNLS
LSCHAASNPPAQYSWLIDGNIQQHTQELFISNITEKNSGLYTCQANNSAS
GHSRTTVKTITVSAELPKPSISSNNSKPVEDKDAVAFTCEPEAQNTTYLW
```

-continued

```
WVNGQSLPVSPRLQLSNGNRTLTLFNVTRNDARAYVCGIQNSVSANRSDP
VTLDVLYGPDTPIISPPDSSYLSGANLNLSCHSASNPSPQYSWRINGIPQ
QHTQVLFIAKITPNNNGTYACFVSNLATGRNNSIVKSITVSASGTSPGLS
AEPKSSDKTHTCPPCPAPELLGGPSVFLFPPKPKDTLMISRTPEVTCVWD
VSHEDPEVKFNWYVDGVEVHNAKTKPREEQYNSTYRWSVLTVLHQDWLNG
KEYKCKVSNKALPAPIEKTISKAKGQPREPQVYTLPPSRDELTKNQVSLT
CLVKGFYPSDIAVEWESNGQPENNYKTTPPVLDSDGSFFLYSKLTVDKSR
WQQGNVFSCSVMHEALHNHYTQKSLSLSPGK
```

3. Amino Acid Sequence of Cynomolgus Monkey CEA-his (cynoCEA-his):

(SEQ ID NO: 3)

```
QLTIESRPFNVAEGKEVLLLAHNVSQNLFGYIWYKGERVDASRRIGSCVI
RTQQITPGPAHSGRETIDFNASLLIQNVTQSDTGSYTIQVIKEDLVNEEA
TGQFRVYPELPKPYITSNNSNPIEDKDAVALTCEPETQDTTYLWWVNNQS
LPVSPRLELSSDNRTLTVFNIPRNDTTSYKCETQNPVSVRRSDPVTLNVL
YGPDAPTISPLNTPYRAGEYLNLTCHAASNPTAQYFWFVNGTFQQSTQEL
FIPNITVNNSGSYMCQAHNSATGLNRTTVTAITVYAELPKPYITSNNSNP
IEDKDAVTLTCEPETQDTTYLWWVNNQRLSVSSRLELSNDNRTLTVFNIP
RNDTTFYECETQNPVSVRRSDPVTLNVLYGPDAPTISPLNTPYRAGENLN
LSCHAASNPAAQYFWFVNGTFQQSTQELFIPNITVNNSGSYMCQAHNSAT
GLNRTTVTAITVYVELPKPYISSNNSNPIEDKDAVTLTCEPVAENTTYLW
WVNNQSLSVSPRLQLSNGNRILTLLSVTRNDTGPYECGIQNSESAKRSDP
VTLNVTYGPDTPIISPPDLSYRSGANLNLSCHSDSNPSPQYSWLINGTLR
QHTQVLFISKITSNNNGAYACFVSNLATGRNNSIVKNISVSSGDSAPGSS
GLSAHHHHHH
```

4. Amino Acid Sequence of Human CEA Expressed on CHO Cell Surface (hCEA-CHO):

(SEQ ID NO: 4)

```
MESPSAPPHRWCIPWQRLLLTASLLTFWNPPTTAKLTIESTPFNVAEGKE
VLLLVHNLPQHLFGYSWYKGERVDGNRQIIGYVIGTQQATPGPAYSGREI
IYPNASLLIQNIIQNDTGFYTLHVIKSDLVNEEATGQFRVYPELPKPSIS
SNNSKPVEDKDAVAFTCEPETQDATYLWWVNNQSLPVSPRLQLSNGNRTL
TLFNVTRNDTASYKCETQNPVSARRSDSVILNVLYGPDAPTISPLNTSYR
SGENLNLSCHAASNPPAQYSWFVNGTFQQSTQELFIPNITVNNSGSYTCQ
AHNSDTGLNRTTVTTITVYAEPPKPFITSNNSNPVEDEDAVALTCEPEIQ
NTTYLWWVNNQSLPVSPRLQLSNDNRTLTLLSVTRNDVGPYECGIQNELS
VDHSDPVILNVLYGPDDPTISPSYTYYRPGVNLSLSCHAASNPPAQYSWL
IDGNIQQHTQELFISNITEKNSGLYTCQANNSASGHSRTTVKTITVSAEL
PKPSISSNNSKPVEDKDAVAFTCEPEAQNTTYLWWVNGQSLPVSPRLQLS
NGNRTLTLFNVTRNDARAYVCGIQNSVSANRSDPVTLDVLYGPDTPIISP
```

-continued

```
PDSSYLSGANLNLSCHSASNPSPQYSWRINGIPQQHTQVLFIAKITPNNN

GTYACFVSNLATGRNNSIVKSITVSASGTSPGLSAGATVGIMIGVLVGVA

LI
```

5. Amino Acid Sequence of Monkey CEA Expressed on CHO Cell Surface (cynoCEA-CHO):

```
                                           (SEQ ID NO: 5)
MEFGLSWLFLVAILKGVQCQLTIESRPFNVAEGKEVLLLAHNVSQNLFGY

IWYKGERVDASRRIGSCVIRTQQITPGPAHSGRETIDFNASLLIQNVTQS

DTGSYTIQVIKEDLVNEEATGQFRVYPELPKPYITSNNSNPIEDKDAVAL

TCEPETQDTTYLWWVNNQSLPVSPRLELSSDNRTLTVFNIPRNDTTSYKC

ETQNPVSVRRSDPVTLNVLYGPDAPTISPLNTPYRAGEYLNLICHAASNP

TAQYFWFVNGTFQQSTQELFIPNITVNNSGSYMCQAHNSATGLNRTTVTA

ITVYAELPKPYITSNNSNPIEDKDAVTLTCEPETQDTTYLWWVNNQRLSV

SSRLELSNDNRTLTVFNIPRNDTTFYECETQNPVSVRRSDPVTLNVLYGP

VELPKPYISSNNSNPIEDKDAVTLTCEPVAENTTYLWWVNNQSLSVSPRL

QDAPTISPLNTPYRAGENLNLSCHAASNPAAQYFWFVNGTFQQSTQELFI

PNITVNNSGSYMCQAHNSATGLNRTTVTAITVYLSNGNRILTLLSVTRND

TGPYECGIQNSESAKRSDPVTLNVTYGPDTPIISPPDLSYRSGANLNLSC

HSDSNPSPQYSWLINGTLRQHTQVLFISKITSNNNGAYACFVSNLATGRN

NSIVKNISVSSGDSAPGSSGLSARATVGIIIGMLVGVALM
```

6. Amino Acid Sequence of Human CEACAM1 Expressed on CHO Cell Surface (CEACAM1-CHO):

```
                                           (SEQ ID NO: 6)
MGHLSAPLHRVRVPWQGLLLTASLLTFWNPPTTAQLTTESMPFNVAEGKE

VLLLVHNLPQQLFGYSWYKGERVDGNRQIVGYAIGTQQATPGPANSGRET

IYPNASLLIQNVTQNDTGFYTLQVIKSDLVNEEATGQFHVYPELPKPSIS

SNNSNPVEDKDAVAFTCEPETQDTTYLWWINNQSLPVSPRLQLSNGNRTL

TLLSVTRNDTGPYECEIQNPVSANRSDPVTLNVTYGPDTPTISPSDTYYR

PGANLSLSCYAASNPPAQYSWLINGTFQQSTQELFIPNITVNNSGSYTCH

ANNSVTGCNRTTVKTIIVTELSPVVAKPQIKASKTTVTGDKDSVNLTCST

NDTGISIRWFFKNQSLPSSERMKLSQGNTTLSINPVKREDAGTYWCEVFN

PISKNQSDPIMLNVNYNALPQENGLSPGAIAGIVIGVVALVALIAVALAC

FLHFGKTGRASDQRDLTEHKPSVSNHTQDHSNDPPNKMNEVTYSTLNFEA

QQPTQPTSASPSLTATEIIYSEVKKQ
```

II. Purification of Related Proteins

1. Purification of Protein with a His Tag

A cell expression supernatant sample was centrifuged at a high speed to remove impurities. A nickel column was equilibrated with PBS buffer (pH 7.4) and washed with 2-5 column volumes, and the supernatant sample was applied to the Ni Sepharose excel column at a flow rate. The column was washed with PBS buffer until $A_{280}$ reading dropped to baseline. Then, the chromatography column was washed with PBS+10 mM imidazole to remove nonspecifically bound impurity proteins, and the flowing-out fluid was collected. Finally, the target protein was eluted with PBS solution containing 300 mM imidazole, and the elution peak was collected. The collected eluate was concentrated, and the sample buffer was changed to a PBS solution by a desalting column to give a mixture for use in subsequent experiments.

2. Purification of Protein Comprising Fc, Chimeric Antibody and Hybridoma Antibody A cell expression supernatant sample was centrifuged at a high speed to remove impurities, the recombinant protein comprising Fc and chimeric antibody expression supernatant were purified using a Protein A column, and the hybridoma expression supernatant was purified using a Protein G column. The supernatant was applied to the column at a flow rate. The column was washed with PBS until $A_{280}$ reading dropped to baseline. The target protein was eluted with 100 mM acetic acid at pH 3.0 and neutralized with 1 M Tris-HCl at pH 8.0. The eluted sample was concentrated, and the sample buffer was changed to PBS to give a mixture, which was aliquoted for later use.

Example 2: Preparation of Mouse Anti-Human CEA Monoclonal Antibody

1. Immunization and Fusion

Mice were immunized with hCEA-His protein and cyno-CEA-His protein, or cross-immunized with hCEA-CHO cells and cynoCEA-CHO cells. The amount of protein immunization was 50 μg for the first immunization and 25 μg for the subsequent immunizations, the cell immunization was at $10^7$ cells per immunization, and the immunization was performed once every two weeks. After 3 immunizations, the blood was taken to determine the potency of antibodies in the serum. Mice in which the antibody titer in serum was high and was reaching a plateau were selected for splenocyte fusion. Spleen lymphocytes and myeloma cells, Sp2/0 cells (ATCC® CRL-8287™), were fused by a PEG-mediated fusion procedure to give hybridoma cells. The fused hybridoma cells were resuspended in MC semisolid complete medium (RPMI-1640 medium containing 20% FBS, 1×HAT, 1×OPI and 2% methyl cellulose) at a density of $0.5\text{-}1\times10^6$ cells/mL, and the suspension was aliquoted into 35 mm cell culture dishes and incubated at 37° C. with 5% $CO_2$ for 7-9 days. On day 7-9 after the fusion, according to the cell clone size, single cell clones were picked up into a 96-well cell culture plate to which 200 μL/well of HT complete medium (RPMI-1640 medium containing 20% FBS, 1×HT and 1×OPI) was added, cultured at 37° C. with 5% $CO_2$ for 3 days, and then detected.

2. Screening of Hybridoma Cells

The primary screening of antibodies was performed based on enzyme-linked immunosorbent assay (ELISA) of cell surface antigens. The cells were applied to an Elisa plate (Corning, Cat #3599) and cultured overnight in an incubator at 37° C. When the cells completely adhered to the wall and nearly filled the whole well, the supernatant was removed. The cells were washed once with PBS, and then fixed with cell fixation buffer (Beyotime, Cat #P0098) at room temperature for 45 min. The fixation buffer was removed, and the plate was washed 3 times using a plate washer, and blocked with 5% skim milk powder at 37° C. for more than 3 h. The blocking buffer was removed, and the plate was washed 3 times using a plate washer. The blocked cell plate was stored at −20° C. or directly used. When the plate was used, gradient diluted hybridoma cell culture supernatant was added, and the plate was incubated at 37° C. for 1 h and washed 3 times using a plate washer. 100 μL of 10,000-fold diluted goat anti-mouse IgG H&L (HRP) secondary antibody (Abcam, Cat #ab205719) was added, and the plate was incubated at 37° C. for 1 h and washed 3 times using a plate washer. 100 μL of TMB (KPL, Cat #5120-0077) was added, and the plate was placed at 37° C. for color developing for 10 min. The reaction was terminated by addition of 100 μL of 1 M sulphuric acid, and the absorbance was read at 450 nm using microplate reader. When the test antibody bound to CEA on the cell surface without being competitively bound by soluble CEA (sCEA), the antibody was incubated with sCEA for 30 min and then added into the cell plate.

The screened positive clones were expanded, frozen for seed preservation and subcloned two to three times until single cell clones were obtained. The screened hybridoma clones were further prepared and purified by serum-free cell culture. The binding of the obtained hybridoma antibody to the CEA protein on the cell surface was detected using a flow cytometer (the method is shown in Test Example 1 of the present disclosure), and hybridoma cell strains with good binding activity were selected. The detection results of the binding activity of monoclonal hybridoma cell strains mAb47, mAb63, mAb67 and mAb103 are shown in Table 1:

TABLE 1

Results of experiment on the binding of murine antibodies to cell surface CEA proteins

| Antibodies | EC50 (nM) MKN45 | cynoCEA-CHO | CEACAM1-CHO |
|---|---|---|---|
| mAb47 | 2.10 | 1.66 | No binding |
| mAb63 | 3.62 | 2.88 | No binding |
| mAb67 | 1.90 | 6.00 | No binding |
| mAb103 | 3.94 | 0.71 | No binding |

3. Sequencing of Hybridoma Antibodies

Monoclonal hybridoma cell strains mAb47, mAb63, mAb67 and mAb103 were selected, and the sequences of the monoclonal antibodies were cloned. The cloning process was as follows: hybridoma cells growing at log phase were collected, and the RNA was extracted using Trizol (Invitrogen, Cat #15596-018) and reverse transcribed into cDNA. After PCR amplification using cDNA as a template, the cDNA was sequenced by a sequencing company, and the amino acid sequences of the antibodies corresponding to the obtained DNA sequences are shown in Table 2 below:

TABLE 2

Variable region sequences of murine anti-CEA antibodies

| Antibodies | Heavy chain variable region sequence VH | Light chain variable region sequence VL |
|---|---|---|
| mAb47 | QIQLVQSGPELKKPGETVKISCKAS GYTFTTYGMSWVKQAPGKGLKW MGWINTYSGVPTYADDFKGRFAF SLETSASTAYLQINNLKNEDTATYF CARRGNYGRWDFDVWGTGTTVT VSS (SEQ ID NO: 7) | EIVLTQSPALMAASPGEKVTIT CSVSSTISSSNLHWYQQKSETS PKPWIYGTSNLASGVPVRFSG SGSGTSYSLTISSMEAEDAATY YCQQWSIYPLTFGAGTKLELK (SEQ ID NO: 8) |
| mAb63 | EVQLQQSGPELVKPGASVKMSCK ASGYTFTDFYMNWVRQSHGKSLE WIGDIFPKNGNTDYNRKFKDKATL TVDKSSNTVYMEFRSLTLEDSAIY FCARSGYGNYVFDYWGQGTIFTV SS (SEQ ID NO: 9) | DVQMTQTPSALSASLGDRVTI SCRTSQDINIYLNWYQQKPDG TVKLLIYYRSGLLSGVPSRFSG SGSGTDYSLTISNLEPEDIATYF CQQGNTLPPTFGGGTKLEIK (SEQ ID NO: 10) |
| mAb67 | EVQLQQSGPELVKPGASVKIYCKA SGYTFTDYHMNWVKQSHGKSLE WIGDINPDIGGTSYNQNFKGKATL TVDKSSSTAYMELRSLTSEDSAVY YCSRWDFDSFANWGQGTLVTVSA (SEQ ID NO: 11) | DIVMTQSPASLAMSLGKRATIS CRASESVSIIGTNLIHWYQQKP GQPPKLLIYHASNLETGVPARF SGSGSGADFTLTIDPVEGDDV ALYYCLQSRKIPYTFGGGTKM EIK (SEQ ID NO: 12) |
| mAb103 | QIQLVQSGPELKKPGETVKISCKAS GYTFTTYGVIWVKQAPGKGLKW MGWINTYSGVPTYADDFKGRFAF SLETSASTAFLQINNLKNEDTATYF CARKKTLTTVTPWFAYWGQGTLV TVSA (SEQ ID NO: 13) | DLVVTQSSSASFSLGASAKLTC TLSSQHSTYTIEWYQQQPLKP PKYVMELKKDGSHSTGDGIPD RFSGSSSGADRYLTISNIQPEDE AIYICGVGNTIKEQFVYVFGG GTKVTVL (SEQ ID NO: 14) |

TABLE 3

CDR sequences of anti-CEA antibodies

| Anti-bodies | Heavy chain CDR sequence | Light chain CDR sequence |
|---|---|---|
| mAb47 | HCDR1TYGMS (SEQ ID NO: 15) | LCDR1SVSSTISSSNLH (SEQ ID NO: 18) |
| | HCDR2WINTYSGVPTYADDFKG (SEQ ID NO: 16) | LCDR2GTSNLAS (SEQ ID NO: 19) |
| | HCDR3RGNYGRWDFDV (SEQ ID NO: 17) | LCDR3QQWSIYPLT (SEQ ID NO: 20) |
| mAb63 | HCDR1DFYMN (SEQ ID NO: 21) | LCDR1RTSQDINIYLN (SEQ ID NO: 24) |
| | HCDR2DIFPKNGNTDYNRKFKD (SEQ ID NO: 22) | LCDR2YRSGLLS (SEQ ID NO: 25) |
| | HCDR3SGYGNYVFDY (SEQ ID NO: 23) | LCDR3QQGNTLPPT (SEQ ID NO: 26) |
| mAb67 | HCDR1DYHMN (SEQ ID NO: 27) | LCDR1RASESVSIIGTNLIH (SEQ ID NO: 30) |
| | HCDR2DINPDIGGTSYNQNFKG (SEQ ID NO: 28) | LCDR2HASNLET (SEQ ID NO: 31) |
| | HCDR3WDFDSFAN (SEQ ID NO: 29) | LCDR3LQSRKIPYT (SEQ ID NO: 32) |
| mAb103 | HCDR1TYGVI (SEQ ID NO: 33) | LCDR1TLSSQHSTYTIE (SEQ ID NO: 35) |
| | HCDR2WINTYSGVPTYADDFKG (SEQ ID NO: 16) | LCDR2LKKDGSHSTGD (SEQ ID NO: 36) |
| | HCDR3KKTLTTVTPWFAY (SEQ ID NO: 34) | LCDR3GVGNTIKEQFVYV (SEQ ID NO: 37) |

Note:
the antibody CDR sequences in the table were determined according to the Kabat numbering system.

4. Preparation of Human IgG1 Chimeric Antibody

The variable region coding gene sequences were obtained by amplifying and sequencing candidate molecules mAb47, mAb63, mAb67 and mAb103 obtained by screening the hybridomas, a head-tail primer was designed using the sequences obtained by sequencing, VH/VK gene fragments were constructed for each antibodies by PCR using the sequenced gene as a template, and homologously recombined with an expression vector pHr (with signal peptide and hIgG1/hkappa/hlambda constant region gene (CH1-Fc/CL) fragment) to construct a recombinant chimeric antibody full-length expression plasmid VH-CH1-Fc-pHr/VL-CL-pHr, and to further obtain chimeric antibodies Ch47, Ch63, Ch67 and Ch103.

Example 3: Humanization of Murine Anti-Human CEA Monoclonal Antibodies

By comparing an IMGT human antibody heavy and light chain variable region germline gene database and an MOE software, heavy and light chain variable region germline genes with high homology were selected as templates, and CDRs of a murine antibody were grafted into corresponding humanized templates to form variable region sequences in a sequence of FR1-CDR1-FR2-CDR2-FR3-CDR3-FR4. The CDR amino acid residues of the antibodies in the following examples were determined and annotated by the Kabat numbering system.

1. Humanization of Murine Antibody mAb47

The heavy and light chain variable region germline genes with high homology were selected as templates; for example, for the murine antibody mAb47, IGKV6-21*01 and IGKJ2*01 were selected as the humanized light chain templates, and IGHV7-4-1*02 and IGHJ6*01 were selected as the humanized heavy chain templates. CDRs of the murine antibody mAb47 were grafted into the corresponding humanized templates for humanization, and the design of the humanized reverse mutations for the murine antibody mAb47 is shown in Table 4 below:

TABLE 4

Humanization design for murine antibody mAb47

| Light chain variable region of humanized antibody of mAb47 | | Heavy chain variable region of humanized antibody of mAb47 | |
|---|---|---|---|
| h47VL1 | Grafted (IGKV6-21*01 + IGKJ2*01) | h47VH1 | Grafted (IGHV7-4-1*02 + IGHJ6*01) |
| h47VL2 | Grafted (IGKV6-21*01 + IGKJ2*01) + L46P, K49Y, F71Y | h47VH2 | Grafted (IGHV7-4-1*02 + IGHJ6*01) + E46K |
| h47VL3 | Grafted (IGKV6-21*01 + IGKJ2*01) + L46P, L47W, K49Y, F71Y | h47VH3 | Grafted(IGHV7-4-1*02 + IGHJ6*01) + R38K, E46K |
| h47VL4 | Grafted (IGKV6-21*01 + IGKJ2*01) + L46P, L47W, K49Y, D70S, F71Y | h47VH4 | Grafted(IGHV7-4-1*02 + IGHJ6*01) + R38K, E46K |

Note: the amino acid positions in the table were numbered using the Kabat numbering scheme; e.g., L46P means that L at position 46 is mutated back to P according to the Kabat numbering system; Grafted means that murine antibody CDRs are grafted into human germline FR region sequences.

In addition, an D61 S mutation was further introduced into the heavy chain variable region h47VH3 (i.e., introducing an amino acid mutation into the antibody HCDR2 so that the sequence of the antibody HCDR2 was changed from WINTYSGVPTYADDFKG (SEQ ID NO: 16) to

WINTYSGVPTYASDFKG (SEQ ID NO: 38))

to obtain the heavy chain variable region h47VH14, with the good activity of the antibody retained.

The specific sequences of the humanized murine antibody mAb47 are shown in Table 5:

TABLE 5

Variable region sequences of humanized murine antibody mAb47

| Variable region Nos. | Variable region sequences of humanized antibody mAb47 |
|---|---|
| h47VH1 | EVQLVQSGSELKKPGASVKVSCKASGYTFTTYGMSWVRQAPGQG LEWMGWINTYSGVPTYADDFKGRFVFSLDTSVSTAYLQISSLKAE DTAVYYCARRGNYGRWDFDVWGQGTTVTVSS (SEQ ID NO: 39) |

TABLE 5-continued

| Variable region sequences of humanized murine antibody mAb47 | |
|---|---|
| Variable region Nos. | Variable region sequences of humanized antibody mAb47 |
| h47VH2 | EVQLVQSGSELKKPGASVKVSCKASGYTFTTYGMSWVRQAPGQG<br>L***K***WMGWINTYSGVPTYADDFKGRFVFSLDTSVSTAYLQISSLKAE<br>DTAVYYCARRGNYGRWDFDVWGQGTTVTVSS<br>(SEQ ID NO: 40) |
| h47VH3 | EVQLVQSGSELKKPGASVKVSCKASGYTFTTYGMSWV***K***QAPGQG<br>L***K***WMGWINTYSGVPTYA***D***DFKGRFVFSLDTSVSTAYLQISSLKAE<br>DTAVYYCARRGNYGRWDFDVWGQGTTVTVSS<br>(SEQ ID NO: 41) |
| h47VH4 | EVQLVQSGSELKKPGASVKVSCKASGYTFTTYGMSWV***K***QAPGQG<br>L***K***WMGWINTYSGVPTYA***S***DFKGRFVFSLDTSVSTAYLQISSLKAE<br>DTAVYYCARRGNYGRWDFDVWGQGTTVTVSS<br>(SEQ ID NO: 42) |
| h47VL1 | EIVLTQSPDFQSVTPKEKVTITCSVSSTISSSNLHWYQQKPDQSPKL<br>LIKGTSNLASGVPSRFSGSGSGTDFTLTINSLEAEDAATYYCQQWSI<br>YPLTFGQGTKLEIK<br>(SEQ ID NO: 43) |
| h47VL2 | EIVLTQSPDFQSVTPKEKVTITCSVSSTISSSNLHWYQQKPDOSPK***P***<br>LI***Y***GTSNLASGVPSRFSGSGSGTDYTLTINSLEAEDAATYYCQQWSI<br>YPLTFGQGTKLEIK<br>(SEQ ID NO: 44) |
| h47VL3 | EIVLTQSPDFQSVTPKEKVTITCSVSSTISSSNLHWYQQKPDOSPK***P***<br>***W***I***Y***GTSNLASGVPSRFSGSGSGTDYTLTINSLEAEDAATYYCQQWS<br>IYPLTFGQGTKLEIK<br>(SEQ ID NO: 45) |
| h47VL4 | EIVLTQSPDFQSVTPKEKVTITCSVSSTISSSNLHWYOQKPDOSPK***P***<br>***W***I***Y***GTSNLASGVPSRFSGSGSGT***SY***TLTINSLEAEDAATYYCQQWSI<br>YPLTFGQGTKLEIK<br>(SEQ ID NO: 46) |

Note:
the CDR regions (determined by the Kabat numbering system) are underlined in the table, and the mutation sites are indicated in bold italics.

2. Humanization of Murine Antibody mAb63

The heavy and light chain variable region germline genes with high homology were selected as templates; for example, for the murine antibody mAb63, IGKV1-39*01 and IGKJ4*01 were selected as the humanized light chain templates, and IGHV1-46*01 and IGHJ1*01 were selected as the humanized heavy chain templates. CDRs of the murine antibody mAb63 were grafted into the corresponding humanized templates for humanization, and the design of the humanized reverse mutation for the murine antibody mAb63 is shown in Table 6 below:

TABLE 6

| Humanized design for murine antibody mAb63 | | | |
|---|---|---|---|
| Light chain variable region of humanized antibody of mAb63 | | Heavy chain variable region of humanized antibody of mAb63 | |
| h63VL1 | Grafted (IGKV1-39*01 + IGKJ4*01) | h63VH1 | Grafted (IGHV1-46*01 + IGHJ1*01) |
| h63VL2 | Grafted (IGKV1-39*01 + IGKJ4*01) + I2V, F71Y | h63VH2 | Grafted (IGHV1-46*01 + IGJ1*01) + M69L, R71V, T73K |
| h63VL3 | Grafted (IGKV1-39*01 + IGKJ4*01) + I2V, K42G, P44V, F71Y | h63VH3 | Grafted (IGHV1-46*01 + IGHJ1*01) + M48I, V67A, M69L, R71V, T73K, L82F |
| | | h63VH4 | Grafted (IGHV1-46*01 + IGHJ1*01) + M48I, R66K, V67A, M69L, R71V, T73K, L82F, S82AR |

Note: the amino acid positions in the table were numbered using the Kabat numbering scheme; e.g., S82AR means that S at position 82A was mutated back to R according to the Kabat numbering system; Grafted means that murine antibody CDRs are grafted into human germline FR region sequences.

In addition, an N54S mutation was further introduced into the heavy chain variable region h63VH1 (i.e., introducing an amino acid mutation into the antibody HCDR2 so that the sequence of the antibody HCDR2 was changed from (SEQ ID NO: 22)
DIFPKNGNTDYNRKFKD
to (SEQ ID NO: 47)
DIFPK*S*GNTDYNRKFKD))

to obtain the heavy chain variable region h63VH5, with the good activity of the antibody retained.

The specific sequences of the humanized and mutated murine antibody mAb63 are shown in Table 7:

TABLE 7

Variable region sequences of humanized murine antibody mAb63

| Variable region Nos. | Variable region sequences of humanized antibody mAb63 |
|---|---|
| h63VH1 | EVQLVQSGAEVKKPGASVKVSCKASGYTFTDFYMNWVRQAPGQGLEWM<br>GDIFPKNGNTDYNRKFKDRVTMTRDTSTSTVYMELSSLRSEDTAVYYCAR<br>SGYGNYVFDYWGQGTLVTVSS<br>(SEQ ID NO: 48) |
| h63VH2 | EVQLVQSGAEVKKPGASVKVSCKASGYTFTDFYMNWVRQAPGQGLEWM<br>GDIFPKNGNTDYNRKFKDRVT***L***T***V***D***K***STSTVYMELSSLRSEDTAVYYCAR<br>SGYGNYVFDYWGQGTLVTVSS<br>(SEQ ID NO: 49) |
| h63VH3 | EVQLVQSGAEVKKPGASVKVSCKASGYTFTDFYMNWVRQAPGQGLEW***I***<br>GDIFPKNGNTDYNRKFKDR***A***T***L***T***V***D***K***STSTVYME***F***SSLRSEDTAVYYCAR<br>SGYGNYVFDYWGQGTLVTVSS<br>(SEQ ID NO: 50) |
| h63VH4 | EVQLVQSGAEVKKPGASVKVSCKASGYTFTDFYMNWVRQAPGQGLEW***I***<br>GDIFPKNGNTDYNRKFKD***KA***T***L***T***V***D***K***STSTVYME***FR***SLRSEDTAVYYCAR<br>SGYGNYVFDYWGQGTLVTVSS<br>(SEQ ID NO: 51) |
| h63VH5 | EVQLVQSGAEVKKPGASVKVSCKASGYTFTDFYMNWVRQAPGQGLEWM<br>GDIFPKSGNTDYNRKFKDRVTMTRDTSTSTVYMELSSLRSEDTAVYYCAR<br>SGYGNYVFDYWGQGTLVTVSS<br>(SEQ ID NO: 52) |
| h63VL1 | DIQMTQSPSSLSASVGDRVTITCRTSQDINIYLNWYQQKPGKAPKLLIYYRS<br>GLLSGVPSRFSGSGSGTDFTLTISSLQPEDFATYYCQQGNTLPPTFGGGTKV<br>EIK<br>(SEQ ID NO: 53) |
| h63VL2 | DVQMTQSPSSLSASVGDRVTITCRTSQDINIYLNWYQQKPGKAPKLLIYYR<br>SGLLSGVPSRFSGSGSGTDFTLTISSLQPEDFATYYCQQGNTLPPTFGGGTK<br>VEIK<br>(SEQ ID NO: 54) |
| h63VL3 | DVQMTQSPSSLSASVGDRVTITCRTSQDINIYLNWYQQKPGGAVKLLIYYR<br>SGLLSGVPSRFSGSGSGTDFTLTISSLQPEDFATYYCQQGNTLPPTFGGGTK<br>VEIK<br>(SEQ ID NO: 55) |

Note:
the CDR regions (determined by the Kabat numbering system) are underlined in the table, and the mutation sites are indicated in bold italics.

3. Humanization of Murine Antibody mAb67

The heavy and light chain variable region germline genes with high homology were selected as templates; for example, for the murine antibody mAb67, IGKV4-1*01 and IGKJ4*01, IGKV3-15*01 and IGKJ4*01, or IGKV1-39*01 and IGKJ4*01 were selected as the humanized light chain templates, and IGHV1-3*01 and IGHJ1*01, or IGHV5-51*01 and IGHJ1*01 were selected as the humanized heavy chain templates. CDRs of the murine antibody mAb67 were grafted into the corresponding humanized templates for humanization, and the design of the humanized reverse mutation for the murine antibody mAb67 is shown in Table 8 below:

TABLE 8

Humanized design for murine antibody mAb67

| Light chain variable region of humanized antibody of mAb67 | | Heavy chain variable region of humanized antibody of mAb67 | |
|---|---|---|---|
| h67VL1 | Graft (IGKV4-1*01 + IGKJ4*01) | h67VH1 | Graft (IGHV1-3*01 + IGHJ1*01) |
| h67VL2 | Graft (IGKV3-15*01 + IGKJ4*01) | h67VH2 | Graft (IGHV5-51*01 + IGHJ1*01) |
| h67VL3 | Graft (IGKV3-15*01 + IGKJ4*01) + A43P, I58V | h67VH3 | Graft (IGHV5-51*01 + IGHJ1*01) + R38K, Q66K, A71V |
| h67VL4 | Graft (IGKV1-39*01 + IGKJ4*01) | | |
| h67VL5 | Graft (IGKV1-39*01 + IGKJ4*01) + Q3V, A43P | | |

Note:
the amino acid positions in the table were numbered using the Kabat numbering scheme; e.g., A43P means that A at position 43 was mutated back to P according to the Kabat numbering system; Grafted means that murine antibody CDRs are grafted into human germline FR region sequences.

The specific sequences of the humanized murine antibody mAb67 are shown in Table 9:

TABLE 9

Variable region sequences of humanized murine antibody mAb67

| Variable region Nos. | Variable region sequences of humanized antibody mAb67 |
|---|---|
| h67VH1 | EVQLVQSGAEVKKPGASVKVSCKASGYTFTDYHMNWVRQAPGQ<br>RLEWMGDINPDIGGTSYNQNFKGRVTITRDTSASTAYMELSSLRSE<br>DTAVYYCARWDFDSFANWGQGTLVTVSS<br>(SEQ ID NO: 56) |
| h67VH2 | EVQLVQSGAEVKKPGESLKISCKGSGYSFTDYHMNWV**R**QMPGKG<br>LEWMGDINPDIGGTSYNQNFKG**Q**VTIS**A**DKSISTAYLQWSSLKAS<br>DTAMYYCARWDFDSFANWGQGTLVTVSS<br>(SEQ ID NO: 57) |
| h67VH3 | EVQLVQSGAEVKKPGESLKISCKGSGYSFTDYHMNWV***K***QMPGKG<br>LEWMGDINPDIGGTSYNQNFKG***K***VTIS***V***DKSISTAYLQWSSLKASD<br>TAMYYCARWDFDSFANWGQGTLVTVSS<br>(SEQ ID NO: 58) |
| h67VL1 | DIVMTQSPDSLAVSLGERATINCRASESVSIIGTNLIHWYQQKPGQP<br>PKLLIYHASNLETGVPDRFSGSGSGTDFTLTISSLQAEDVAVYYCLQ<br>SRKIPYTFGGGTKVEIK<br>(SEQ ID NO: 59) |
| h67VL2 | EIVMTQSPATLSVSPGERATLSCRASESVSIIGTNLIHWYQQKPGQ**A**<br>PRLLIYHASNLETG**I**PARFSGSGSGTEFTLTISSLQSEDFAVYYCLQS<br>RKIPYTFGGGTKVEIK<br>(SEQ ID NO: 60) |
| h67VL3 | EIVMTQSPATESVSPGERATLSCRASESVSIIGTNLIHWYQQKPGQP<br>PRLLIYHASNLETG***V***PARFSGSGSGTEFTLTISSLQSEDFAVYYCLQS<br>RKIPYTFGGGTKVEIK<br>(SEQ ID NO: 61) |
| h67VL4 | DI**Q**MTQSPSSLSASVGDRVTITCRASESVSIIGTNLIHWYQQKPGK**A**<br>PKLLIYHASNLETGVPSRFSGSGSGTDFTLTISSLQPEDFATYYCLQS<br>RKIPYTFGGGTKVEIK<br>(SEQ ID NO: 62) |
| h67VL5 | DI***V***MTQSPSSLSASVGDRVTITCRASESVSIIGTNLIHWYQQKPGK***P***<br>PKLLIYHASNLETGVPSRFSGSGSGTDFTLTISSLQPEDFATYYCLQS<br>RKIPYTFGGGTKVEIK<br>(SEQ ID NO: 63) |

Note: the CDR regions (determined by the Kabat numbering system) are underlined in the table, and the mutation sites are indicated in bold italics.

4. Humanization of Murine Antibody mAb103

The heavy and light chain variable region germline genes with high homology were selected as templates; for example, for the murine antibody mAbf03, IGLV4H69*V1 and IGLJ2*01 were selected as the humanized light chain templates, and IGHV7-4-1*02 and IGHJ1*01 were selected as the humanized heavy chain templates. CDRs of the murine antibody mAb103 were grafted into the corresponding humanized templates for humanization, and the design of the humanized reverse mutation for the murine antibody mAb103 is shown in Table 10 below:

TABLE 10

Humanized design for murine antibody mAb103

| Light chain variable region of humanized antibody of mAb103 | | Heavy chain variable region of humanized antibody of mAb67 | |
|---|---|---|---|
| h103VL1 | Graft (IGLV4-69*01 + IGLJ2*01) + K49E | h103VH1 | Graft (IGHV7-4-1*02 + IGHJ1*01) |
| h103VL2 | Graft (IGLV4-69*01 + IGLJ2*01) + H36Y, K49E | h103VH2 | Graft (IGHV7-4-1*02 + IGHH*01) + R38K, E46K |
| h103VL3 | Graft (IGLV4-69*01 + IGLJ2*01) + H36Y, L47V, K49E | h103VH3 | Graft (IGHV7-4-1*02 + IGHJ1*01) + V2I, R38K, E46K |
| h103VL4 | Graft (IGLV4-69*01 + IGLJ2*01) + L4V, H36Y, L47V, K49E | | |
| h103VL5 | Graft (IGLV4-69*01 + IGLJ2*01) + H36Y, G43P, L47V, K49E, Y87I | | |
| h103VL6 | Graft (IGLV4-69*01 + IGLJ2*01) + L4V, H36Y, G43P, L47V, K49E, Y87I | | |
| h103VL7 | Graft (IGLV4-69*01 + IGLJ2*01) + L4V, H36Y, G43P, L47V, K49E, E70D, Y87I | | |

Note:
the amino acid positions in the table were numbered using the Kabat numbering scheme, e.g., K49E means that K at position 49 was mutated back to E according to the Kabat numbering system; Grafted means that murine antibody CDRs are grafted into human germline FR region sequences.

In addition, an D61S mutation was further introduced into the heavy chain h103VH1 (i.e., introducing an amino acid mutation into the antibody HCDR2 so that the sequence of the antibody HCDR2 was changed from (SEQ ID NO: 16)
WINTYSGVPTYADDFKG
to (SEQ ID NO: 38)
WINTYSGVPTYASDFKG));

and an D56E mutation was introduced into the light chain h103VL3 (i.e., introducing an amino acid mutation into the antibody LCDR2 so that the sequence of the antibody LCDR2 was changed from LKKDGSHSTGD (SEQ ID NO: 36) to LKKDGSHSTGE (SEQ ID NO: 64)), with the good activity of the antibody retained.

The specific sequences of the humanized murine antibody mAb103 are shown in Table 11:

TABLE 11

Variable region sequences of humanized murine antibody mAb103

| Variable region Nos. | Variable region sequences of humanized antibody mAb103 |
|---|---|
| h103VH1 | EVQLVQSGSELKKPGASVKVSCKASGYTFTTYGVIWVRQAPGQ<br>GLEWMGWINTYSGVPTYADDFKGRFVFSLDTSVSTAYLQISSLK<br>AEDTAVYYCARKKTLTTVTPWFAYWGQGTLVTVSS<br>(SEQ ID NO: 65) |
| h103VH2 | EVQLVQSGSELKKPGASVKVSCKASGYTFTTYGVIWV***K***QAPGQ<br>GL***K***WMGWINTYSGVPTYADDFKGRFVFSLDTSVSTAYLQISSLK<br>AEDTAVYYCARKKTLTTVTPWFAYWGQGTLVTVSS<br>(SEQ ID NO: 66) |
| h103VH3 | E***I***QLVQSGSELKKPGASVKVSCKASGYTFTTYGVIWV***K***QAPGQG<br>L***K***WMGWINTYSGVPTYADDFKGRFVFSLDTSVSTAYLQISSLKA<br>EDTAVYYCARKKTLTTVTPWFAYWGQGTLVTVSS<br>(SEQ ID NO: 67) |
| h103VH4 | EVQLVQSGSELKKPGASVKVSCKASGYTFTTYGVIWVRQAPGQ<br>GLEWMGWINTYSGVPTYA***S***DFKGRFVFSLDTSVSTAYLQISSLKA<br>EDTAVYYCARKKTLTTVTPWFAYWGQGTLVTVSS<br>(SEQ ID NO: 68) |
| h103VL1 | ELVLTQSPSASASLGASVKLTCTLSSQHSTYTIEWHQQQPEKGPR<br>YLM***E***LKKDGSHSTGDGIPDRFSGSSSGAERYLTISSLQSEDEADY<br>YCGVGNTIKEQFVYVFGGGTKLTVL<br>(SEQ ID NO: 69) |
| h103VL2 | ELVLTQSPSASASLGASVKLTCTLSSQHSTYTIEW***Y***QQQPEKGPR<br>YLM***E***LKKDGSHSTGDGIPDRFSGSSSGAERYLTISSLQSEDEADY<br>YCGVGNTIKEQFVYVFGGGTKLTVL<br>(SEQ ID NO: 70) |

TABLE 11-continued

Variable region sequences of humanized murine antibody mAb103

| Variable region Nos. | Variable region sequences of humanized antibody mAb103 |
|---|---|
| h103VL3 | ELVLTQSPSASASLGASVKLTCTLSSQHSTYTIEW***Y***QQQPEKGPR<br>Y***V***M***E***LKKDGSHSTGDGIPDRFSGSSSGAERYLTISSLQSEDEADY<br>YCGVGNTIKEQFVYVFGGGTKLTVL<br>(SEQ ID NO: 71) |
| h103VL4 | ELV***V***TQSPSASASLGASVKLTCTLSSQHSTYTIEW***Y***QQQPEKGPR<br>Y***V***M***E***LKKDGSHSTGDGIPDRFSGSSSGAERYLTISSLQSEDEADY<br>YCGVGNTIKEQFVYVFGGGTKLTVL<br>(SEQ ID NO: 72) |
| h103VL5 | ELVLTQSPSASASLGASVKLTCTLSSQHSTYTIEW***Y***QQQPEK***P***PRY<br>***V***M***E***LKKDGSHSTGDGIPDRFSGSSSGAERYLTISSLQSEDEADY***I***C<br>GVGNTIKEQFVYVFGGGTKLTVL<br>(SEQ ID NO: 73) |
| h103VL6 | ELV***V***TQSPSASASLGASVKLTCTLSSQHSTYTIEW***Y***QQQPEK***P***PR<br>Y***V***M***E***LKKDGSHSTGDGIPDRFSGSSSGAERYLTISSLQSEDEADY***I***<br>CGVGNTIKEQFVYVFGGGTKLTVL<br>(SEQ ID NO: 74) |
| h103VL7 | ELV***V***TQSPSASASLGASVKLTCTLSSQHSTYTIEW***Y***QQQPEK***P***PR<br>Y***V***M***E***LKKDGSHSTGDGIPDRFSGSSSGA***D***RYLTISSLQSEDEADY<br>***I***CGVGNTIKEQFVYVFGGGTKLTVL<br>(SEQ ID NO: 75) |
| h103VL8 | ELVL**T**QSPSASASLGASVKLTCTLSSQHSTYTIEW***Y***QQQPEKGPR<br>Y***V***M***E***LKKDGSHSTG***E***GIPDRFSGSSSGAERYLTISSLQSEDEADY<br>YCGVGNTIKEQFVYVFGGGTKLTVL<br>(SEQ ID NO: 76) |

Note:
the CDR regions (determined by the Kabat numbering system) are underlined in the table, and the mutation sites are indicated in bold italics.

5. Preparation of Humanized Antibodies

Expression vectors of the light chain and the heavy chain of an antibody were constructed, respectively; cross-pairing combination was performed on the light chain and the heavy chain of a humanized antibody, the culture supernatant was collected and purified after 293E cells were transfected to obtain the humanized full-length antibody. The heavy chain constant region of humanized antibody may be selected from the group consisting of the constant regions of IgG1, IgG2, IgG3 and IgG4, and variants thereof; illustratively, the human heavy chain IgG1 constant region (as set forth in SEQ ID NO: 77) was joined to the aforementioned humanized heavy chain variable region to form a full-length heavy chain of the antibody. The light chain constant region of the humanized antibody may be selected from the group consisting of the constant regions of human κ and χ chains or variants thereof; illustratively, the human light chain constant region κ chain (as set forth in SEQ ID NO: 78) or human light chain constant region λ chain (as set forth in SEQ ID NO: 79) was joined to the aforementioned humanized light chain variable region to form a full-length light chain of the antibody.

The constant region sequences of exemplary antibodies are as follows:

Heavy Chain Constant Region of Human IgG1:

SEQ ID NO: 77

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

-continued

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDSRWK

QQGNVFSCSVMHEALHNHYTQKSLSLSPGK

Human Light Chain Constant Region κ Chain:

SEQ ID NO: 78

RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC

Human Light Chain Constant Region λ Chain:

SEQ ID NO: 79

GQPKANPTVTLFPPSSEELQANKATLVCLISDFYPGAVTVAWKADGSPVK

AGVETTKPSKQSNNKYAASSYLSLTPEQWKSHRSYSCQVTHEGSTVEKTV

APTECS

Illustratively, the aforementioned heavy chain variable region of the humanized antibody derived from mAb47 as shown in Table 5 was joined to the amino-terminus of the human heavy chain IgG1 constant region having a sequence set forth in SEQ ID NO: 77 to form a full-length heavy chain of the antibody, and the light chain variable region of the humanized antibody as shown in Table 5 was joined to the amino-terminus of the human light chain κ constant region having a sequence set forth in SEQ ID NO: 78 to form a full-length light chain of the antibody, resulting in a range of humanized antibodies of mAb47 shown in Table 12 below:

TABLE 12

| Humanized antibodies of mAb47 | | | | |
|---|---|---|---|---|
| | VH | | | |
| VL | h47VH1 | h47VH2 | h47VH3 | h47VH4 |
| h47VL1 | Hu47-1 | Hu47-5 | Hu47-9 | Hu47-13 |
| h47VL2 | Hu47-2 | Hu47-6 | Hu47-10 | Hu47-14 |
| h47VL3 | Hu47-3 | Hu47-7 | Hu47-11 | Hu47-15 |
| h47VL4 | Hu47-4 | Hu47-8 | Hu47-12 | Hu47-16 |

Note: in the table, for example, "Hu47-14" indicates that the light chain variable region of the humanized antibody numbered Hu47-14 is h47VL2, and the heavy chain variable region is h47VH4; and the heavy chain constant region sequence is set forth in SEQ ID NO: 77, and the light chain constant region sequence is set forth in SEQ ID NO: 78.

Illustratively, the aforementioned heavy chain variable region of humanized antibody derived from mAb63 as shown in Table 7 was joined to the amino-terminus of the human heavy chain IgG1 constant region having a sequence set forth in SEQ ID NO: 77 to form a full-length heavy chain of the antibody, and the light chain variable region of humanized antibody as shown in Table 7 was joined to the amino-terminus of the human light chain κ constant region having a sequence set forth in SEQ ID NO: 78 to form a full-length light chain of the antibody, resulting in a range of humanized antibodies of mAb63 shown in Table 13 below:

TABLE 13

| Humanized antibodies of mAb63 | | | | | |
|---|---|---|---|---|---|
| | VH | | | | |
| VL | h63VH1 | h63VH2 | h63VH3 | h63VH4 | h63VH5 |
| h63VL1 | Hu63-1 | Hu63-4 | Hu63-7 | Hu63-10 | Hu63-13 |
| h63VL2 | Hu63-2 | Hu63-5 | Hu63-8 | Hu63-11 | Hu63-14 |
| h63VL3 | Hu63-3 | Hu63-6 | Hu63-9 | Hu63-12 | Hu63-15 |

Note: in the table, for example, "Hu63-13" indicates that the light chain variable region of the humanized antibody numbered Hu63-13 is h63VL1, and the heavy chain variable region is h63VH5; and the heavy chain constant region sequence is set forth in SEQ ID NO: 77, and the light chain constant region sequence is set forth in SEQ ID NO: 78.

Illustratively, the aforementioned heavy chain variable region of humanized antibody derived from mAb67 as shown in Table 9 was joined to the amino-terminus of the human heavy chain IgG1 constant region having a sequence set forth in SEQ ID NO: 77 to form a full-length heavy chain of the antibody, and the light chain variable region of the humanized antibody as shown in Table 9 was joined to the amino-terminus of the human light chain κ constant region having a sequence set forth in SEQ ID NO: 78 to form a full-length light chain of the antibody, resulting in a range of humanized antibodies of mAb67 shown in Table 14 below.

TABLE 14

| Humanized antibodies of mAb67 | | | |
|---|---|---|---|
| | VH | | |
| VL | h67VH1 | h67VH2 | h67VH3 |
| h67VL1 | Hu67-1 | Hu67-6 | Hu67-11 |
| h67VL2 | Hu67-2 | Hu67-7 | Hu67-12 |
| h67VL3 | Hu67-3 | Hu67-8 | Hu67-13 |
| h67VL4 | Hu67-4 | Hu67-9 | Hu67-14 |
| h67VL5 | Hu67-5 | Hu67-10 | Hu67-15 |

Note: in the table, for example, "Hu67-14" indicates that the light chain variable region of the humanized antibody numbered Hu67-14 is h67VL4, and the heavy chain variable region is h67VH3; and the heavy chain constant region sequence is set forth in SEQ ID NO: 77, and the light chain constant region sequence is set forth in SEQ ID NO: 78.

Illustratively, the aforementioned heavy chain variable region of humanized antibody derived from mAb103 as shown in Table 11 was joined to the amino-terminus of the human heavy chain IgG1 constant region having a sequence set forth in SEQ ID NO: 77 to form a full-length heavy chain of the antibody, and the light chain variable region of the humanized antibody as shown in Table 11 was joined to the amino-terminus of the human light chain λ constant region having a sequence set forth in SEQ ID NO: 79 to form a full-length light chain of the antibody, resulting in a range of humanized antibodies of mAb103 shown in Table 15 below:

TABLE 15

| Humanized antibodies of mAb103 | | | | |
|---|---|---|---|---|
| | VH | | | |
| VL | h103VH1 | h103VH2 | h103VH3 | h103VH4 |
| h103VL1 | Hu103-1 | Hu103-9 | Hu103-17 | Hu103-25 |
| h103VL2 | Hu103-2 | Hu103-10 | Hu103-18 | Hu103-26 |
| h103VL3 | Hu103-3 | Hu103-11 | Hu103-19 | Hu103-27 |
| h103VL4 | Hu103-4 | Hu103-12 | Hu103-20 | Hu103-28 |
| h103VL5 | Hu103-5 | Hu103-13 | Hu103-21 | Hu103-29 |
| h103VL6 | Hu103-6 | Hu103-14 | Hu103-22 | Hu103-30 |
| h103VL7 | Hu103-7 | Hu103-15 | Hu103-23 | Hu103-31 |
| h103VL8 | Hu103-8 | Hu103-16 | Hu103-24 | Hu103-32 |

Note: in the table, for example, "Hu103-32" indicates that the light chain variable region of the humanized antibody numbered Hu103-32 is h103VL8, and the heavy chain variable region is h103VH4; and the heavy chain constant region sequence is set forth in SEQ ID NO: 77, and the light chain constant region sequence is set forth in SEQ ID NO: 79.

Illustratively, the light/heavy chain full-length sequences of the humanized antibodies are shown in Table 16 below:

TABLE 16

| Light and heavy chain sequences of humanized antibodies | | |
|---|---|---|
| Antibody Nos. | Heavy chain sequence | Light chain sequence |
| Hu63-13 | EVQLVQSGAEVKKPGASVKVSCKASG<br>YTFTDFYMNWVRQAPGQGLEWMGDIF<br>PKSGNTDYNRKFKDRVTMTRDTSTSTV | DIQMTQSPSSLSASVGD<br>RVTITCRTSQDINIYLN<br>WYQQKPGKAPKLLIYY |

TABLE 16-continued

| Light and heavy chain sequences of humanized antibodies | | |
|---|---|---|
| Antibody Nos. | Heavy chain sequence | Light chain sequence |
| | YMELSSLRSEDTAVYYCARSGYGNYVF<br>DYWGQGTLVTVSSASTKGPSVFPLAPSS<br>KSTSGGTAALGCLVKDYFPEPVTVSWNSG<br>ALTSGVHTFPAVLQSSGLYSLSSVVTVPSSS<br>LGTQTYICNVNHKPSNTKVDKKVEPKSC<br>DKTHTCPPCPAPELLGGPSVFLFPPKPK<br>DTLMISRTPEVTCVVVDVSHEDPEVKFN<br>WYVDGVEVHNAKTKPREEQYNSTYRVVS<br>VLTVLHQDWLNGKEYKCKVSNKALPAPIE<br>KTISKAKGQPREPQVYTLPPSRDELTKNQ<br>VSLTCLVKGFYPSDIAVEWESNGQPENNY<br>KTTPPVLDSDGSFFLYSKLTVDKSRWQQG<br>NVFSCSVMHEALHNHYTQKSLSLSPGK<br>SEQ ID NO: 80 | RSGLLSGVPSRFSGSGS<br>GTDFTLTISSLQPEDFAT<br>YYCQQGNTLPPTFGGG<br>TKNEWRTVAAPSVFIFP<br>PSDEQLKSGTASVVCLLN<br>NFYPREAKVQWKVDNA<br>LQSGNSQESVTEQDSKD<br>STYSLSSTLTLSKADYEK<br>HKVYACEVTHQGLSSPV<br>TKSFNRGEC<br>SEQ ID NO: 81 |
| Hu47-14 | EVQLVQSGSELKKPGASVKVSCKASGY<br>TFTTYGMSWVKQAPGQGLKWMGWIN<br>TYSGVPTYASDFKGRFVFSLDTSVSTAY<br>LQISSLKAEDTAVYYCARRGNYGRWDF<br>DVWGQGTTVTVSSASTKGPSVFPLAPSS<br>KSTSGGTAALGCLVKDYFPEPVTVSWNSG<br>ALTSGVHTFPAVLQSSGLYSLSSVVTVPSSS<br>LGTQTYICNVNHKPSNTKVDKKVEPKSC<br>DKTHTCPPCPAPELLGGPSVFLFPPKPK<br>DTLMISRTPEVTCVVVDVSHEDPEVKFN<br>WYVDGVEVHNAKTKPREEQYNSTYRVVS<br>VLTVLHQDWLNGKEYKCKVSNKALPAPIE<br>KTISKAKGQPREPQVYTLPPSRDELTKNQ<br>VSLTCLVKGFYPSDIAVEWESNGQPENNY<br>KTTPPVLDSDGSFFLYSKLTVDKSRWQQG<br>NVFSCSVMHEALHNHYTQKSLSLSPGK<br>SEQ ID NO: 82 | EIVLTQSPDFQSVTPKE<br>KVTITCSVSSTISSSNLH<br>WYQQKPDQSPKPLIYG<br>TSNLASGVPSRFSGSGS<br>GTDYTLTINSLEAEDAA<br>TYYCQQWSIYPLTFGQ<br>GTKLEIKRTVAAPSVFIF<br>PPSDEQLKSGTASVVCLL<br>NNFYPREAKVQWKVDN<br>ALQSGNSQESVTEQDSK<br>DSTYSLSSTLTLSKADYE<br>KHKVYACEVTHQGLSSP<br>VTKSFNRGEC<br>SEQ ID NO: 83 |
| Hu67-14 | EVQLVQSGAEVKKPGESLKISCKGSGY<br>SFTDYHMNWVKQMPGKGLEWMGDIN<br>PDIGGTSYNQNFKGKVTISVDKSISTAY<br>LQWSSLKASDTAMYYCARWDFDSFAN<br>WGQGTLVTVSSASTKGPSVFPLAPSSKST<br>SGGTAALGCLVKDYFPEPVTVSWNSGALT<br>SGVHTFPAVLQSSGLYSLSSVVTVPSSSLGT<br>QTYICNVNHKPSNTKVDKKVEPKSCDKT<br>HTCPPCPAPELLGGPSVFLFPPKPKDTL<br>MISRTPEVTCVVVDVSHEDPEVKFNWYV<br>DGVEVHNAKTKPREEQYNSTYRVVSVLTV<br>LHQDWLNGKEYKCKVSNKALPAPIEKTIS<br>KAKGQPREPQVYTLPPSRDELTKNQVSLT<br>CLVKGFYPSDIAVEWESNGQPENNYKTTP<br>PVLDSDGSFFLYSKLTVDKSRWQQGNVFS<br>CSVMHEALHNHYTQKSLSLSPGK<br>SEQ ID NO: 84 | DIQMTQSPSSLSASVGD<br>RVTITCRASESVSIIGTN<br>LIHWYQQKPGKAPKLL<br>IYHASNLETGVPSRFSG<br>SGSGTDFTLTISSLQPED<br>FATYYCLQSRKIPYTFG<br>GGTKVEIKRTVAAPSVFI<br>FPPSDEQLKSGTASVVCL<br>LNNFYPREAKVQWKVD<br>NALQSGNSQESVTEQDS<br>KDSTYSLSSTLTLSKADY<br>EKHKVYACEVTHQGLSS<br>PVTKSFNRGEC<br>SEQ ID NO: 85 |
| Hu103-32 | EVQLVQSGSELKKPGASVKVSCKASGY<br>TFTTYGVIWVRQAPGQGLEWMGWINT<br>YSGVPTYASDFKGRFVFSLDTSVSTAYL<br>QISSLKAEDTAVYYCARKKTLTTVTPW<br>FAYWGQGTLVTVSSASTKGPSVFPLAPS<br>SKSTSGGTAALGCLVKDYFPEPVTVSWNS<br>GALTSGVHTFPAVLQSSGLYSLSSVVTVPSS<br>SLGTQTYICNVNHKPSNTKVDKKVEPKSC<br>DKTHTCPPCPAPELLGGPSVFLFPPKPK<br>DTEMISRTPEVTCVVVDVSHEDPEVKFN<br>WYVDGVEVHNAKTKPREEQYNSTYRVVS<br>VLTVLHQDWLNGKEYKCKVSNKALPAPIE<br>KTISKAKGQPREPQVYTLPPSRDELTKNQ<br>VSLTCLVKGFYPSDIAVEWESNGQPENNY<br>KTTPPVLDSDGSFFLYSKLTVDKSRWQQG<br>NVFSCSVMHEALHNHYTQKSLSLSPGK<br>SEQ ID NO: 86 | ELVLTQSPSASASLGAS<br>VKLTCTLSSQHSTYTIE<br>WYQQQPEKGPRYVME<br>LKKDGSHSTGEGIPDRF<br>SGSSSGAERYLTISSLQS<br>EDEADYYCGVGNTIKE<br>QFVYVFGGGTKLTVLG<br>QPKANPTVTLFPPSSEEL<br>QANKATLVCLISDFYPGA<br>VTVAWKADGSPVKAGVE<br>TTKPSKQSNNKYAASSYL<br>SLTPEQWKSHRSYSCQV<br>THEGSTVEKTVAPTECS<br>SEQ ID NO: 87 |

Note:
in the table, italics represent constant region sequences and upright letters represent variable region sequences.

Currently 2 known CEA target ADC molecules are SAR-408701 and labetuzumab govitecan (also referred to as Lmab-CL2A-SN38), in which the light and heavy chain sequences of the antibodies are as follows:

Heavy Chain Sequence of the Antibody in SAR-408701 (Sanofi):

SEQ ID NO: 88

```
EVQLQESGPGLVKPGGSLSLSCAASGFVFSSYDMSWVRQTPERGLEWVAY
ISSGGGITYAPSTVKGRFTVSRDNAKNTLYLQMNSLTSEDTAVYYCAAHY
FGSSGPFAYWGQGTLVTVSSASTKGPSVFPLAPSSKSTSGGTAALGCLVK
DYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK
```

Light Chain Sequence of the Antibody in SAR-408701 (Sanofi for Short)

SEQ ID NO: 89

```
DIQMTQSPASLSASVGDRVTITCRASENIFSYLAWYQQKPGKSPKLLVYN
TRTLAEGVPSRFSGSGSGTDFSLTISSLQPEDFATYYCQHHYGTPFTFGS
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC
```

Heavy Chain Sequence of the Antibody Labetuzumab in Lmab-CL2A-SN38 (Lmab for Short)

SEQ ID NO: 90

```
EVQLVESGGGVVQPGRSLRLSCSASGFDFTTYWMSWVRQAPGKGLEWIGE
IHPDSSTINYAPSLKDRFTISRDNAKNTLFLQMDSLRPEDTGVYFCASLY
FGFPWFAYWGQGTPVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKRVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPGK
```

Light Chain Sequence of Labetuzumab in Lmab-CL2A-SN38 (Lmab)

SEQ ID NO: 91

```
DIQLTQSPSSLSASVGDRVTITCKASQDVGTSVAWYQQKPGKAPKLLIYW
TSTRHTGVPSRFSGSGSGTDFTFTISSLQPEDIATYYCQQYSLYRSFGQG
TKVEIKRTVAAPSVFIFPPSDEQLKSGTASVVCLLNNFYPREAKVQWKVD
```

-continued

```
NALQSGNSQESVTEQDSKDSTYSLSSTLTLSKADYEKHKVYACEVTHQGL
SSPVTKSFNRGEC
```

The above antibodies were cloned, expressed and purified using conventional gene cloning and recombinant expression methods.

Example 4: Preparation of Compounds

Experimental procedures without conditions specified in the examples of the present disclosure, are generally conducted according to conventional conditions, or according to conditions recommended by the manufacturer of the starting materials or commercial products. Reagents without specific origins indicated are commercially available conventional reagents.

The structure of the compounds were determined by nuclear magnetic resonance (NMR) or mass spectrometry (MS). NMR spectra were measured using a Bruker AVANCE-400 nuclear magnetic resonance instrument, with deuterated dimethyl sulfoxide (DMSO-d6), deuterated chloroform ($CDCl_3$) and deuterated methanol ($CD_3OD$) as solvents and tetramethylsilane (TMS) as internal standard. Chemical shifts are given in unit of $10^{-6}$ (ppm).

MS analysis was performed using a FINNIGAN LCQAd (ESI) mass spectrometer (manufacturer: Thermo, model: Finnigan LCQ advantage MAX).

UPLC analysis was performed using a Waters Acquity UPLC SQD liquid chromatography-mass spectrometry system.

HPLC analysis was performed using an Agilent 1200DAD high pressure liquid chromatograph (Sunfire C18 150×4.6 mm chromatography column) and a Waters 2695-2996 high pressure liquid chromatograph (Gimini C18 150×4.6 mm chromatography column).

UV-HPLC analysis was performed using a Thermo nanodrop2000 ultraviolet spectrophotometer.

Proliferation inhibition rates and $IC_{50}$ values were measured using a PHERA starFS microplate reader (BMG, Germany).

Huanghai HSGF254 or Qingdao GF254 silica gel plates of specifications 0.15 mm to 0.2 mm were adopted for thin layer chromatography (TLC) analysis and 0.4 mm to 0.5 mm for TLC separation and purification.

Yantai Yellow Sea silica gel of 200-300 mesh is generally used as a carrier in column chromatography.

Known starting materials of the present disclosure may be synthesized using or according to methods known in the art, or may be purchased from ABCR GmbH & Co.KG, Acros Organnics, Aldrich Chemical Company, Accela ChemBio Inc, Chembee Chemicals and the like.

In the examples, the reactions were performed in an argon atmosphere or a nitrogen atmosphere unless otherwise stated.

An argon atmosphere or a nitrogen atmosphere means that the reaction flask is connected to a balloon containing about 1 L of argon or nitrogen.

A hydrogen atmosphere means that the reaction flask is connected to a balloon containing about 1 L of hydrogen.

Parr 3916EKX hydrogenator, Qinglan QL-500 hydrogenator or HC2-SS hydrogenator was used for pressurized hydrogenation reactions.

The hydrogenation reaction usually involved 3 cycles of vacuumization and hydrogen purge.

A CEM Discover-S 908860 microwave reactor was used for the microwave reaction.

In the examples, the solution in the reaction refers to an aqueous solution unless otherwise stated.

In the examples, the reaction temperature is room temperature unless otherwise stated.

The room temperature is the optimum reaction temperature, which ranges from 20° C. to 30° C.

Preparation of PBS buffer at pH 6.5 in examples: 8.5 g of $KH_2PO_4$, 8.56 g of $K_2HIPO_4.3H_2O$, 5.85 g of NaCl and 1.5 g of EDTA were added to a flask, and the volume was brought to 2 L. The additions were all ultrasonically dissolved, and the solution was well mixed by shaking to give the desired buffer.

The eluent system for column chromatography and the developing solvent system for thin layer chromatography used for compound purification include: A: dichloromethane and isopropanol system, B: dichloromethane and methanol system, and C: petroleum ether and ethyl acetate system. The volume ratio of solvents was adjusted according to the polarity of the compound, or by adding a small amount of triethylamine and acidic or basic reagent.

Some of the compounds of the present disclosure are characterized by Q-TOF LC/MS. Q-TOF LC/MS analysis used an Agilent 6530 accurate-mass quadrupole time-of-flight mass spectrometer and an Agilent 1290-Infinity ultra-high performance liquid chromatograph (Agilent Poroshell 300SB-C8 5 m, 2.1×75 mm chromatography column).

Y-D drug portion of the antibody drug conjugates of the present disclosure is found in PCT/CN2019/107873, and the synthesis and tests of relevant compounds are incorporated herein by reference. Non-limiting examples of synthesis are incorporated by reference as follows:

1. Synthesis of Toxin Drugs of the Present Disclosure

(S)-2-cyclopropyl-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-2-hydroxyacetamide 1-A

(R)-2-cyclopropyl-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-2-hydroxyacetamide 1-B

1-A

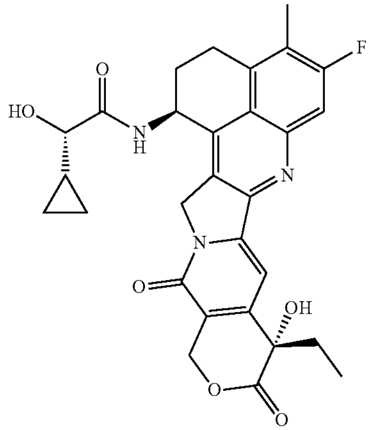

-continued

1-B

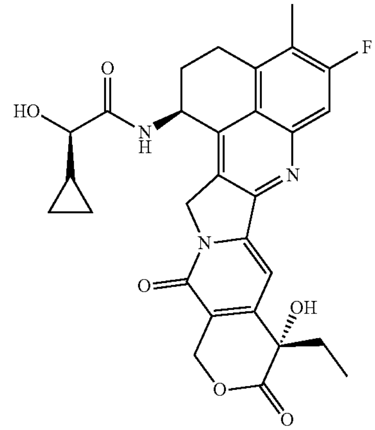

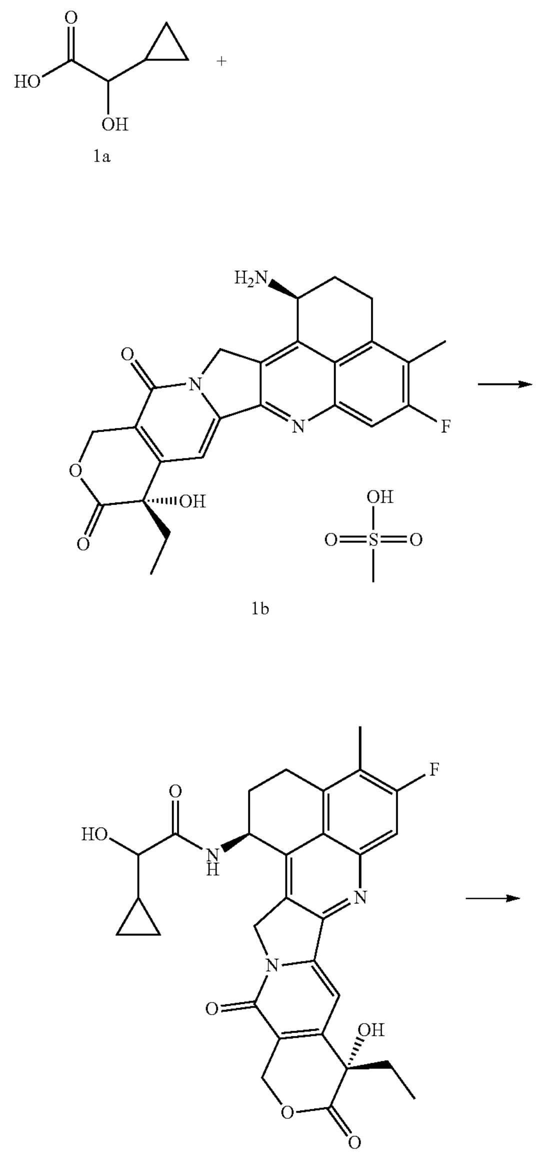

1a

1b

1

-continued

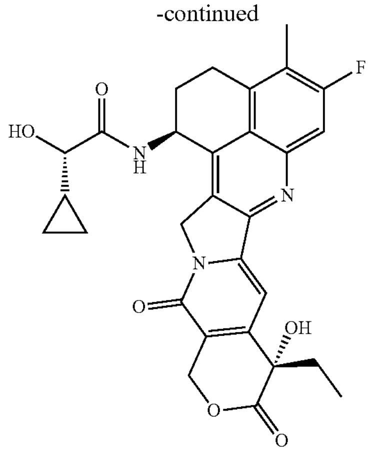

+

1-A

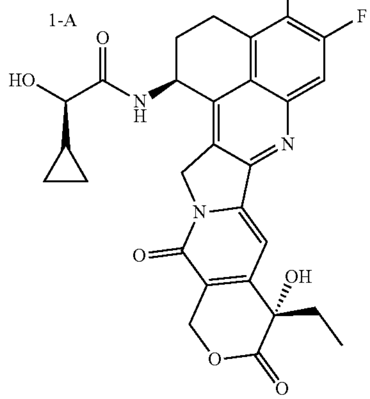

1-B

To 1b (4 mg, 7.53 μmol) were added 2 mL of ethanol and 0.4 mL of N,N-dimethylformamide. The system was purged with argon three times, and the mixture was cooled to 0-5° C. in an ice-water bath, followed by dropwise addition of 0.3 mL of N-methylmorpholine. The reaction mixture was stirred until it became clear. To the reaction mixture were successively added 2-cyclopropyl-2-hydroxyacetic acid 1a (2.3 mg, 19.8 μmol, prepared as disclosed in Patent Application "WO2013106717"), 1-hydroxybenzotriazole (3 mg, 22.4 μmol) and 1-(3-dimethylaminopropyl)-3-ethylcarbodiimide hydrochloride (4.3 mg, 22.4 μmol). After addition, the reaction mixture was stirred at 0-5° C. for 1 h. The ice-water bath was removed, and the reaction mixture was heated to 30° C., stirred for 2 h, and concentrated under reduced pressure. The resulting crude compound 1 was purified by high performance liquid chromatography (separation conditions: chromatography column: XBridge Prep C18 OBD 5 m 19×250 mm; mobile phase: A-water (10 mmol of $NH_4OAc$), B-acetonitrile, gradient elution, flow rate: 18 mL/min), and the corresponding fractions were collected and concentrated under reduced pressure to give the title product (1-A: 1.5 mg, 1-B: 1.5 mg).

MS m/z (ESI): 534.0 [M+1].

Single-Configuration Compound 1-B (Shorter Retention Time)

UPLC analysis: retention time: 1.06 min; purity: 88% (chromatography column: ACQUITY UPLC BEHC18 1.7 m 2.1×50 mm; mobile phase: A-water (5 mmol of $NH_4OAc$), B-acetonitrile).

$^1$H NMR (400 MHz, DMSO-$d_6$): δ 8.37 (d, 1H), 7.76 (d, 1H), 7.30 (s, 1H), 6.51 (s, 1H), 5.58-5.56 (m, 1H), 5.48 (d, 1H), 5.41 (s, 2H), 5.32-5.29 (m, 2H), 3.60 (t, 1H), 3.19-3.13 (m, 1H), 2.38 (s, 3H), 2.20-2.14 (m, 1H), 1.98 (q, 2H), 1.87-1.83 (m, 1H), 1.50-1.40 (m, 1H), 1.34-1.28 (m, 1H), 0.86 (t, 3H), 0.50-0.39 (m, 4H).

Single-Configuration Compound 1-A (Longer Retention Time)

UPLC analysis: retention time: 1.10 min; purity: 86% (chromatography column: ACQUITY UPLC BEHC18 1.7 m 2.1×50 mm; mobile phase: A-water (5 mmol of $NH_4OAc$), B-acetonitrile).

$^1$H NMR (400 MHz, DMSO-$d_6$): δ 8.35 (d, 1H), 7.78 (d, 1H), 7.31 (s, 1H), 6.52 (s, 1H), 5.58-5.53 (m, 1H), 5.42 (s, 2H), 5.37 (d, 1H), 5.32 (t, 1H), 3.62 (t, 1H), 3.20-3.15 (m, 2H), 2.40 (s, 3H), 2.25-2.16 (m, 1H), 1.98 (q, 2H), 1.87-1.82 (m, 1H), 1.50-1.40 (m, 1H), 1.21-1.14 (m, 1H), 0.87 (t, 3H), 0.47-0.35 (m, 4H).

2. Synthesis of Linker Toxin Drugs of the Present Disclosure

N-((2R,10S)-10-benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadecan-16-yl)-6-(2,5-dioxo-2,5-dihydro-1H-pyrrol-1-yl)hexanamide 2-A N-((2S,10S)-10-benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadecan-16-yl)-6-(2,5-dioxo-2,5-dihydro-1H-pyrrol-1-yl)hexanamide 2-B

2-A

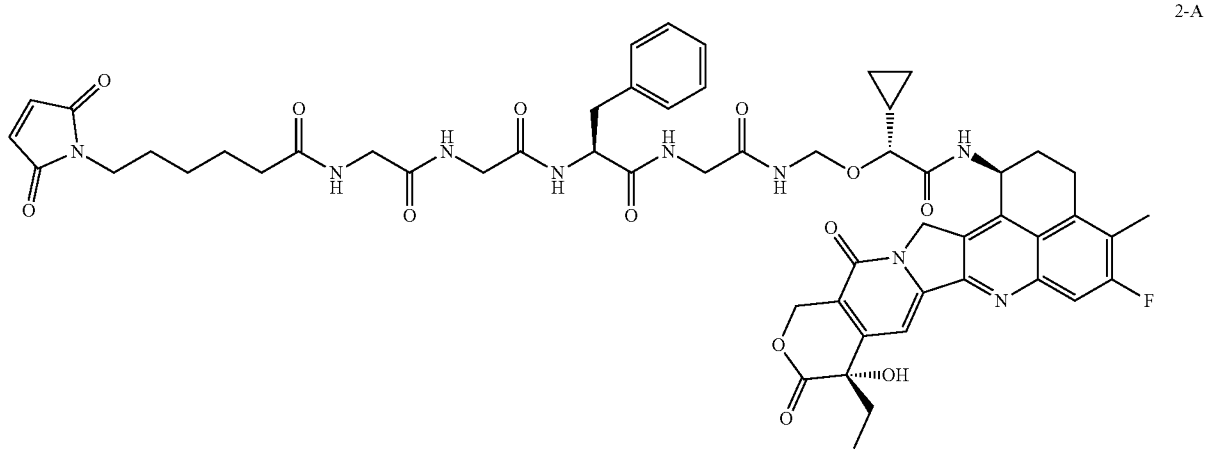

-continued
2-B
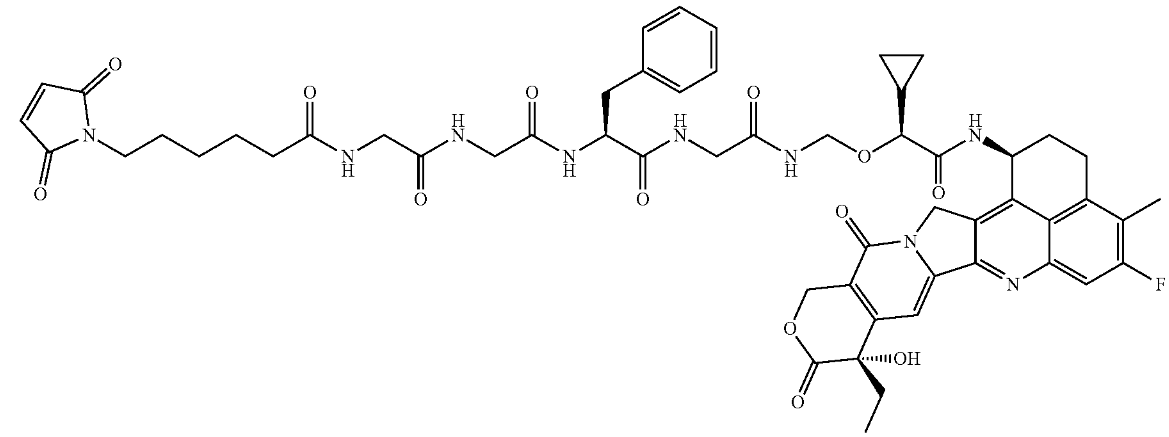
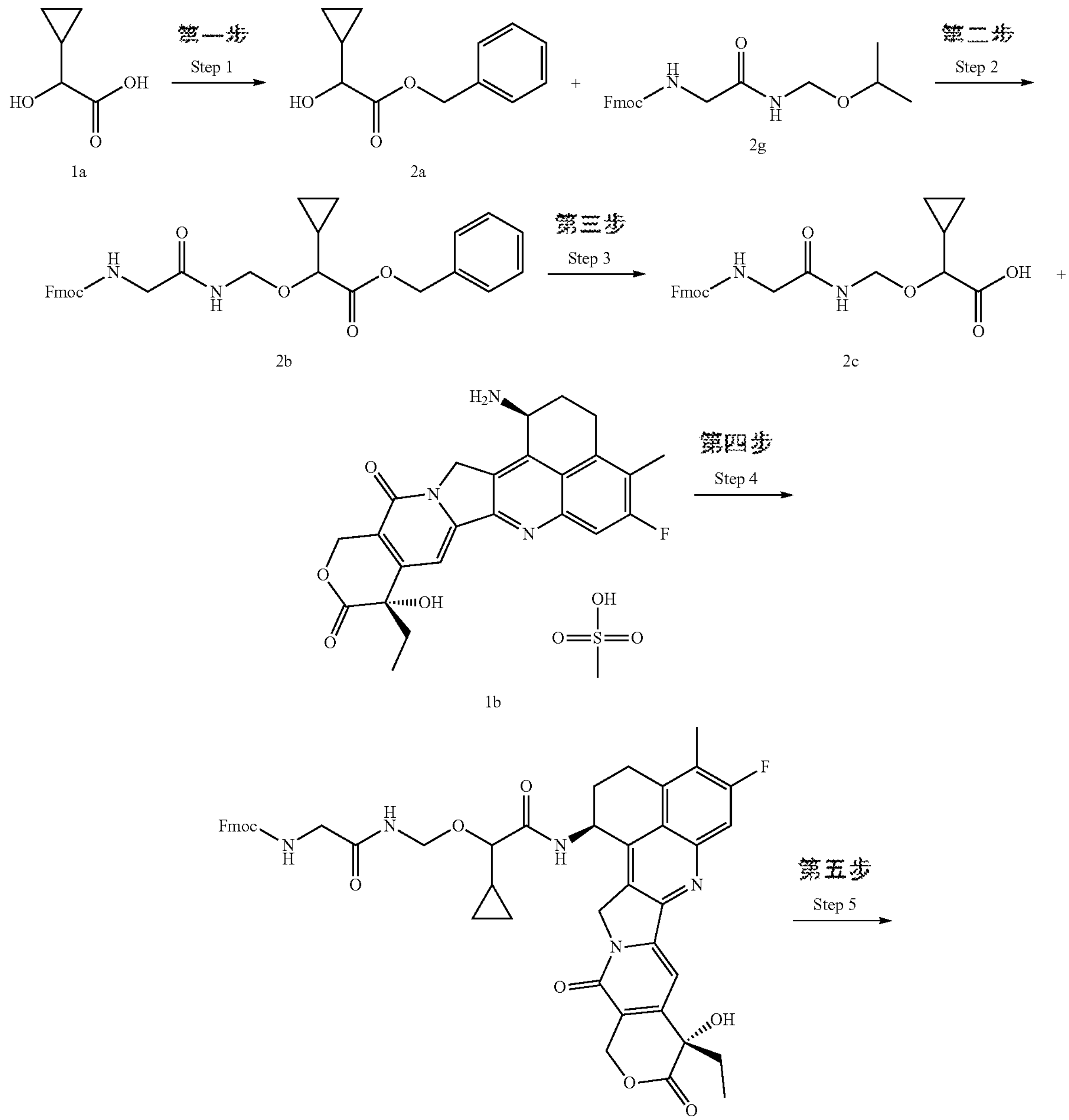
1a 2a 2g
2b 2c
1b
2d

-continued
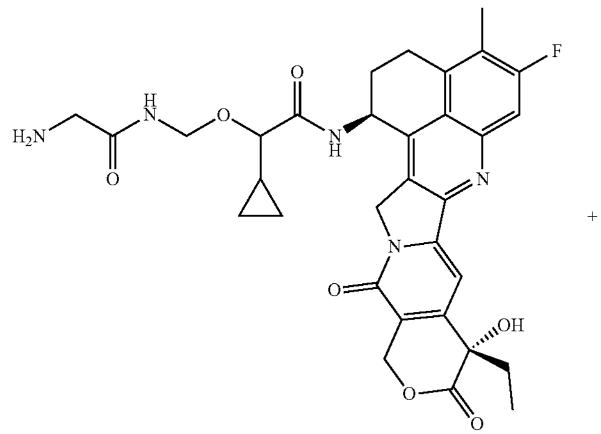
2e
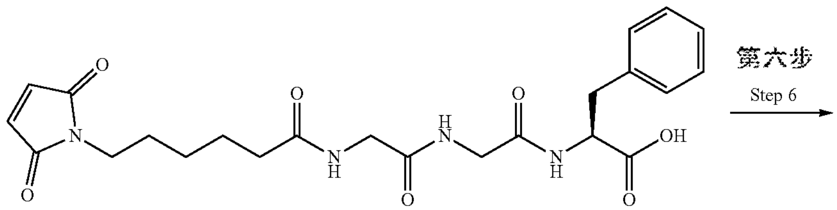
2f
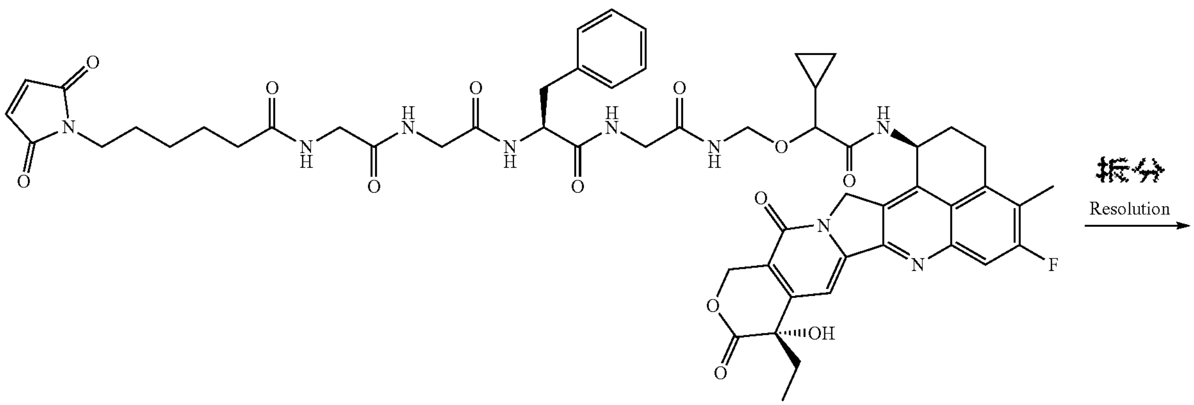
2
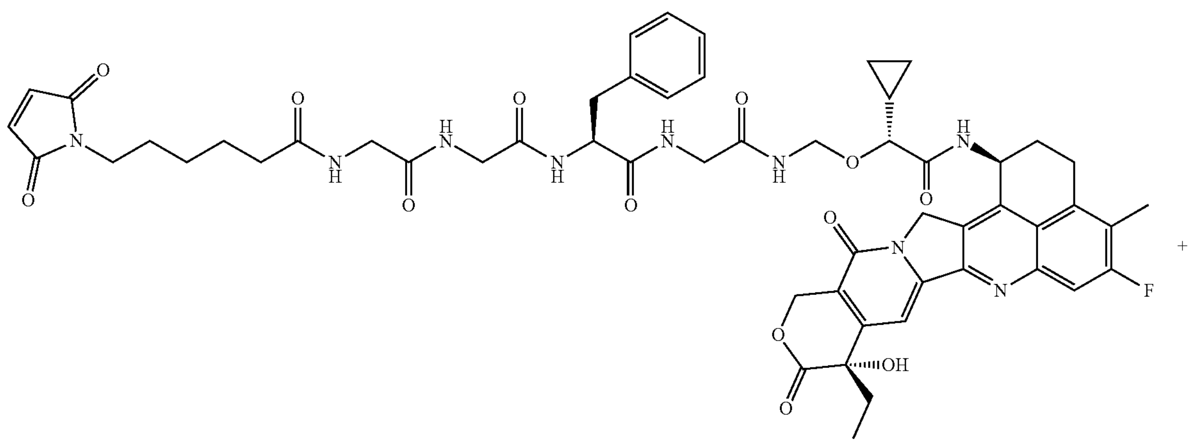
2-A

-continued

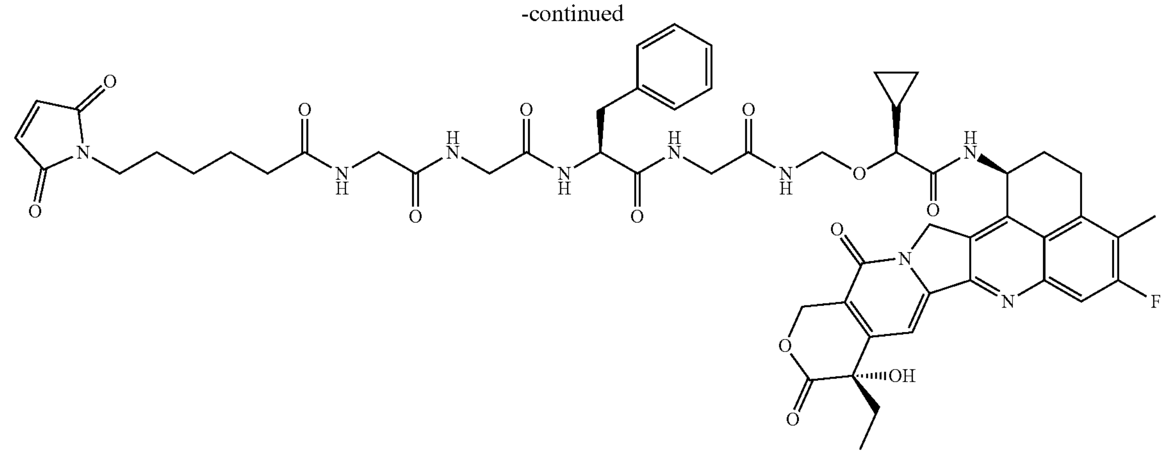

2-B

Step 1

Benzyl 2-cyclopropyl-2-hydroxyacetate 2a 1a (1.3 g, 11.2 mmol; prepared as disclosed in Patent Application "WO2013/106717") was dissolved in 50 mL of acetonitrile, and potassium carbonate (6.18 g, 44.8 mmol), benzyl bromide (1.33 mL, 11.2 mmol) and tetrabutyl ammonium iodide (413 mg, 1.1 mmol) were successively added. The reaction mixture was stirred at room temperature for 48 h and filtered through celite, and the filter cake was rinsed with ethyl acetate (10 mL). The filtrates were combined and concentrated under reduced pressure, and the resulting residue was purified by silica gel column chromatography with developing solvent system C to give the title product 2a (2 g, 86.9% yield).

Step 2

Benzyl 10-cyclopropyl-1-(9H-fluoren-9-yl)-3,6-dioxo-2,9-dioxa-4,7-diazaundecan-11-oate 2b 2a (120.9 mg, 0.586 mmol) and 2 g (180 mg, 0.489 mmol, prepared as disclosed in Patent Application "CN105829346A") were added to a reaction flask, and 4 mL of tetrahydrofuran was added. The system was purged with argon three times, and the reaction mixture was cooled to 0-5° C. in an ice-water bath, followed by addition of potassium tert-butoxide (109 mg, 0.98 mmol). The ice bath was removed, and the reaction mixture was warmed to room temperature and stirred for 40 min, followed by addition of 10 mL of ice water and by extraction with ethyl acetate (20 mL×2) and chloroform (10 mL×5). The organic phases were combined and concentrated. The resulting residue was dissolved in 4 mL of dioxane, and 2 mL of water, sodium bicarbonate (49.2 mg, 0.586 mmol) and 9-fluorenylmethyl chloroformate (126 mg, 0.49 mmol) were added. The mixture was stirred at room temperature for 2 h. 20 mL of water was added, followed by extraction with ethyl acetate (10 mL×3). The organic phase was washed with saturated sodium chloride solution (20 mL), dried over anhydrous sodium sulfate, and filtered. The filtrate was concentrated under reduced pressure. The resulting residue was purified by silica gel column chromatography with developing solvent system C to give the title product 2b (48 mg, 19% yield).

MS m/z (ESI): 515.0 [M+1].

Step 3

10-Cyclopropyl-1-(9H-fluoren-9-yl)-3,6-dioxo-2,9-dioxa-4,7-diazaundecan-11-oic acid 2c 2b (20 mg, 0.038 mmol) was dissolved in 4.5 mL of a solvent mixture of tetrahydrofuran and ethyl acetate (V:V=2:1), and palladium on carbon (12 mg, 10% loading, dry basis) was added. The system was purged with hydrogen three times, and the reaction mixture was stirred at room temperature for 1 h. The reaction mixture was filtered through celite, and the filter cake was rinsed with ethyl acetate. The filtrate was concentrated to give the crude title product 2c (13 mg), which was directly used in the next step without purification.

MS m/z (ESI): 424.9 [M+1].

Step 4

(9H-fluoren-9-yl)methyl(2-(((1-cyclopropyl-2-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-2-oxoethoxy)methyl)amino)-2-oxoethyl)carbamate 2d 1b (10 mg, 18.8 μmol) was added to a reaction flask, and 1 mL of N,N-dimethylformamide was added. The system was purged with argon three times, and the mixture was cooled to 0-5° C. in an ice-water bath, followed by addition of a drop of triethylamine, crude 5c (13 mg, 30.6 μmol), and 4-(4,6-dimethoxy-1,3,5-triazin-2-yl)-4-methylmorpholinium chloride (16.9 mg, 61.2 μmol). The reaction mixture was stirred in an ice bath for 40 min. 10 mL of water was added, followed by extraction with ethyl acetate (10 mL×3). The organic phases were combined, washed with saturated sodium chloride solution (10 mL×2), dried over anhydrous sodium sulfate, and filtered. The filtrate was concentrated under reduced pressure. The resulting residue was purified by thin layer chromatography with developing solvent system B to give the title product 2d (19 mg, 73.6% yield).

MS m/z (ESI): 842.1 [M+1].

Step 5

2-((2-Aminoacetamido)methoxy)-2-cyclopropyl-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)acetamide 2e 2d (19 mg, 22.6 μmol) was dissolved in 2 mL of dichloromethane, and 1 mL of diethylamine was added. The reaction mixture was stirred at room temperature for 2 h and concentrated under reduced pressure. 1 mL of toluene was added, followed by concentration under reduced pressure; the procedures were repeated twice. The residue was slurried with 3 mL of n-hexane and let stand. Then, the supernatant was removed, and the solid was kept. The solid residue was concentrated under reduced pressure and dried using an oil pump to give the crude title product 2e (17 mg), which was directly used in the next step without purification.

MS m/z (ESI): 638.0 [M+18].

Step 6

N-((2R,10S)-10-benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadecan-16-yl)-6-(2,5-dioxo-2,5-dihydro-1H-pyrrol-1-yl)hexanamide 2-A N-((2S,10S)-10-benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadecan-16-yl)-6-(2,5-dioxo-2,5-dihydro-1H-pyrrol-1-yl)hexanamide 2-B Crude 2e (13.9 mg, 22.4 μmol) was dissolved in 0.6 mL of N,N-dimethylformamide. The system was purged with argon three times, and the solution was cooled to 0-5° C. in an ice-water bath. A solution of 2f (21.2 mg, 44.8 μmol, prepared as disclosed in Patent Application "EP2907824") in 0.3 mL of N,N-dimethylformamide was added, followed by addition of 4-(4,6-dimethoxy-1,3,5-triazin-2-yl)-4-methylmorpholinium chloride (18.5 mg, 67.3 μmol). The reaction mixture was stirred in an ice bath for 10 min. Then, the ice bath was removed, and the reaction mixture was warmed to room temperature and stirred for 1 h to produce compound 2. The reaction mixture was purified by high performance liquid chromatography (separation conditions: chromatography column: XBridge Prep C18 OBD 5 m 19×250 mm; mobile phase: A-water (10 mmol of $NH_4OAc$), B-acetonitrile, gradient elution, flow rate: 18 mL/min). The corresponding fractions were collected and concentrated under reduced pressure to give the title products (2-A: 2.4 mg, 2-B: 1.7 mg).

MS m/z (ESI): 1074.4 [M+1].

Single-Configuration Compound 2-A (Shorter Retention Time):

UPLC analysis: retention time: 1.14 min; purity: 85% (chromatography column: ACQUITY UPLC BEHC18 1.7 m 2.1×50 mm; mobile phase: A-water (5 mmol of $NH_4OAc$), B-acetonitrile).

$^1$H NMR (400 MHz, DMSO-$d_6$): δ 8.60 (t, 1H), 8.51-8.49 (d, 1H), 8.32-8.24 (m, 1H), 8.13-8.02 (m, 2H), 8.02-7.96 (m, 1H), 7.82-7.75 (m, 1H), 7.31 (s, 1H), 7.26-7.15 (m, 4H), 6.99 (s, 1H), 6.55-6.48 (m, 1H), 5.65-5.54 (m, 1H), 5.41 (s, 2H), 5.35-5.15 (m, 3H), 4.74-4.62 (m, 1H), 4.54-4.40 (m, 2H), 3.76-3.64 (m, 4H), 3.62-3.48 (m, 2H), 3.20-3.07 (m, 2H), 3.04-2.94 (m, 1H), 2.80-2.62 (m, 12H), 2.45-2.30 (m, 3H), 2.25-2.15 (m, 2H), 2.15-2.04 (m, 2H), 1.93-1.78 (m, 2H), 1.52-1.39 (m, 3H), 1.34-1.12 (m, 5H), 0.87 (t, 3H), 0.64-0.38 (m, 4H).

Single-Configuration Compound 2-B (Longer Retention Time):

UPLC analysis: retention time: 1.16 min; purity: 89% (chromatography column: ACQUITY UPLC BEHC18 1.7 m 2.1×50 mm; mobile phase: A-water (5 mmol of $NH_4OAc$), B-acetonitrile).

$^1$H NMR (400 MHz, DMSO-$d_6$): δ 8.68-8.60 (m, 1H), 8.58-8.50 (m, 1H), 8.32-8.24 (m, 1H), 8.13-8.02 (m, 2H), 8.02-7.94 (m, 1H), 7.82-7.75 (m, 1H), 7.31 (s, 1H), 7.26-7.13 (m, 3H), 6.99 (s, 1H), 6.55-6.48 (m, 1H), 5.60-5.50 (m, 1H), 5.41 (s, 2H), 5.35-5.15 (m, 2H), 4.78-4.68 (m, 1H), 4.60-4.40 (m, 2H), 3.76-3.58 (m, 4H), 3.58-3.48 (m, 1H), 3.20-3.10 (m, 2H), 3.08-2.97 (m, 2H), 2.80-2.72 (m, 2H), 2.45-2.30 (m, 3H), 2.25-2.13 (m, 2H), 2.13-2.04 (m, 2H), 2.03-1.94 (m, 2H), 1.91-1.78 (m, 2H), 1.52-1.39 (m, 3H), 1.34-1.12 (m, 4H), 0.91-0.79 (m, 3H), 0.53-0.34 (m, 4H).

Example 5: Preparation of Antibody Drug Conjugates (ADCs)

Drug-Loading Analysis of ADC Stock Solution

Purpose and Principle of Experiment

ADC stock solution is an antibody cross-linked drug, and the mechanism of treating diseases thereof is to transport toxin molecules into cells depending on the targeting performance of the antibody so as to kill the cells. The drug loading plays a decisive role in the drug efficacy. The drug loading of the ADC stock solution was determined using the UV method.

Experimental Procedures

Cuvettes containing sodium succinate buffer were placed into the reference cell and sample cell, and the absorbance of the solvent blank was subtracted. Then, a cuvette containing test solution was placed into the sample cell, and the absorbances at 280 nm and 370 nm were determined.

Calculation for results: the loading capacity of the ADC stock solution was determined by ultraviolet spectrophotometry (instrument: Thermo nanodrop2000 ultraviolet spectrophotometer), based on the principle that the total absorbance of the ADC stock solution at a certain wavelength was the sum of the absorbance values of the drug and the monoclonal antibody at that wavelength, namely:

$$A_{280\ nm}=\varepsilon_{mab\text{-}280}bC_{mab}+\varepsilon_{Drug\text{-}280}bC_{Drug} \quad (1)$$

$\varepsilon_{Drug\text{-}280}$: the mean molar attenuation coefficient of the drug at 280 nm is 5100;

$C_{Drug}$: the concentration of the drug;

$\varepsilon_{mab\text{-}280}$: the mean molar attenuation coefficient of the monoclonal antibody stock solution at 280 nm is 214,600;

$C_{mab}$: the concentration of the monoclonal antibody stock solution;

b: the optical path length is 1 cm.

Similarly, an equation for the total absorbance of the sample at 370 nm can be given as:

$$A_{370\ nm}=\varepsilon_{mab\text{-}370}bC_{mab}+\varepsilon_{Drug\text{-}370}bC_{Drug} \quad (2)$$

$\varepsilon_{Drug\text{-}370}$: the mean molar attenuation coefficient of the drug at 370 nm was 19,000;

$C_{Drug}$: the concentration of the drug;

$\varepsilon_{mab\text{-}370}$: the attenuation coefficient of the monoclonal antibody stock solution at 370 nm is 0;

$C_{mab}$: the concentration of the monoclonal antibody stock solution;

b: the optical path length is 1 cm.

The drug loading can be calculated using both equations (1) and (2) as well as the attenuation coefficients of the monoclonal antibody and the drug at both wavelengths and their concentrations.

$$\text{Drug loading}=C_{Drug}/C_{mab}.$$

1. Preparation of Antibody Drug Conjugates (ADCs) of the Present Disclosure

The toxin compound 1-B is a DNA topoisomerase I inhibitor, and a complex formed by the toxin compound, topoisomerase I and DNA can cause single-strand breaks in DNA, preventing DNA replication and effectively inhibiting cell proliferation in cells.

The ADC was prepared as follows: a humanized antibody (selected from the group consisting of Hu63-13, Hu47-14, Hu67-14 and Hu103-32) was placed in a 0.05 M aqueous PBS buffer (with the antibody at a concentration of 10 mg/mL) at pH 6.5, and a 10 mM aqueous solution of tris(2-carboxyethyl)phosphine (TCEP) (Innochem, CAS: 51805-45-9, Cat #B45573) was added in a molar amount that was 5.3 times that of the antibody; the mixture was allowed to react in a shaking incubator at a constant temperature of 37° C. for 3 h. The above reaction mixture was cooled to 25° C. in an ice bath.

The toxin compound 2-A was dissolved in dimethyl sulfoxide in a molar amount that was 15 times that of the antibody, and the resulting solution was added into the above reaction mixture, which was then allowed to react on a shaker at room temperature for 3 h before the reaction was terminated. The reaction mixture was desalted and purified through a Sephadex G25 gel column (elution phase: 0.05 M PBS buffer at pH 6.5, containing 0.01 M EDTA) to obtain the target antibody drug conjugate molecule with a drug-to-antibody ratio (DAR, value n) of 6-8.

Those skilled in the art can obtain conjugates with different DAR values by adjusting the reaction conditions and reagents. For example, ADC molecules with a drug-to-antibody molar ratio (DAR, value n) of 3-5 were obtained by adjusting the molar ratio of the antibody to TCEP to the toxin compound by adding a 10 mM aqueous solution of tris(2-carboxyethyl)phosphine (TCEP) in a molar amount that was 2.5 times that of the antibody and adding the toxin compound 2-A in a molar amount that was 10 times that of the antibody.

The specific ADCs prepared are as follows:

| ADC samples | Antibody comprised | DAR value (n) |
|---|---|---|
| Hu47-14-2-A | Hu47-14 | 6.6 |
| Hu63-13-2-A | Hu63-13 | 6.29 |
| Hu67-14-2-A | Hu67-14 | 6.41 |
| Hu103-32-2-A | Hu103-32 | 6.94 |
| Hu63-13-2-A | Hu63-13 | 3.97 |
| Hu67-14-2-A | Hu67-14 | 4.28 |
| Hu103-32-2-A | Hu103-32 | 4.8 |

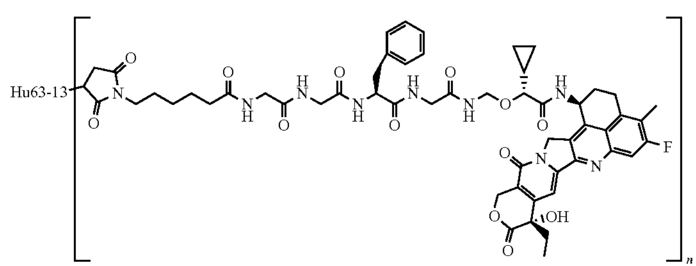

Hu63-13-2-A

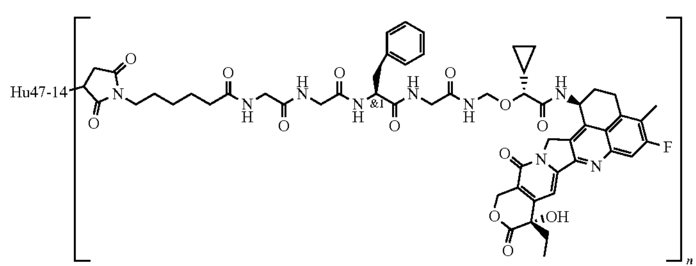

Hu47-14-2-A

-continued

| ADC samples | Antibody comprised | DAR value (n) |
|---|---|---|

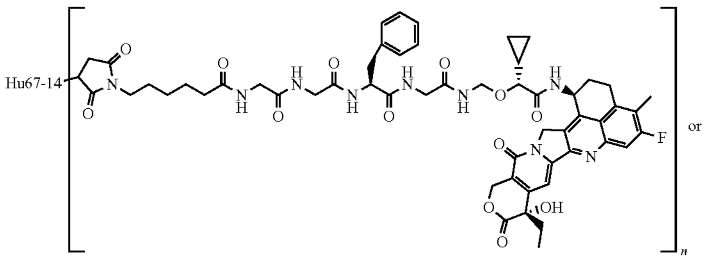

or

Hu67-14-2-A

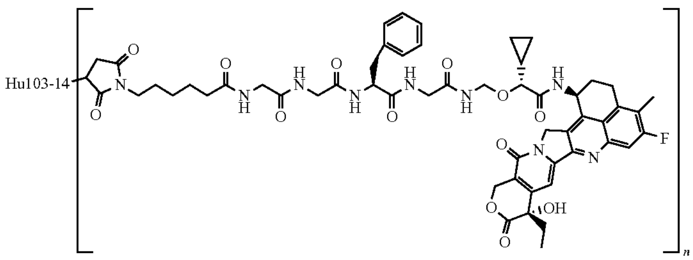

Hu103-32-2-A

The present disclosure also prepares ADCs with other DAR values as required by test examples, see the following test examples for details.

2. Preparation of Control ADC Lmab-CL2A-SN38 (ADC-4)

In order to evaluate the differences between the constructed ADC in the present disclosure and the control ADC molecule Lmab-CL2A-SN38, toxin CL2A-SN38 was synthesized with reference to the structure described in *WHO Drug Information* Vol. 30, No. 1, 2016 and the method described in the *Mol pharm.* 2015 Jun. 1; 12(6):1836-47, and conjugated to Lmab to form ADC molecules Lmab-CL2A-SN38 with different DAR values by adjusting the reaction conditions as described in the preparation of ADCs above. The prepared ADC molecules were stored at −20° C. for later use.

TEST EXAMPLES

Test Example 1: FACS Binding Assay

In order to detect the binding of the antibody to the CEA protein on the cell surface, the binding activity of the antibody was determined by FACS using cells expressing CEA on the cell surface. Cells were harvested and centrifuged at 400 g at 4° C. for 5 min. Pre-cooled PBS containing FBS at final concentration 10% was added, and the mixture was centrifuged at 400 g at 4° C. for 5 min; the procedures were repeated twice. The cells were seeded into a 96-well plate at $10^5$ cells/well, and 100 μL of gradient diluted antibody solution was added to each well. The plate was incubated at 4° C. for 60 min and centrifuged, and the supernatant was removed. 250 μL of pre-cooled PBS containing FBS at final concentration 10% was added to each well to resuspend the cells, and the suspension was centrifuged at 400 g at 4° C. for 5 min, followed by the removal of the supernatant; the procedures were repeated twice. 50 μL of 1:200 diluted secondary antibody Alexa Fluor@488 goat anti-human IgG (H+L) (Lifetechologies, Cat #A11013) was added. The plate was incubated in the dark at 4° C. for 45 min and centrifuged, and the supernatant was removed. 250 μL of pre-cooled PBS containing FBS at final concentration 10% was added to each cell to resuspend the cells, and the suspension was centrifuged at 400 g at 4° C. for 5 min; the procedures were repeated twice. 100 μL of pre-cooled PBS was added to each well to resuspend the cells. The plate was analyzed by a flow cytometer (BD, FACS-verse) for fluorescence signal values. Higher values indicate higher binding activity of the antibody to the protein on the cell surface. Binding curves were plotted using PRISM analysis software based on the assay results, and the $EC_{50}$ values for the binding activity of the antibody to the cell surface proteins human CEA (MKN45 human gastric cancer cells, Nanjing Kebai Biotechnology Co., Ltd., Cat #CBP60488), cynoCEA-CHO and CEACAM1-CHO were obtained by fitting. The binding activity of the humanized antibodies is shown in Tables 17 and 18 below

TABLE 17

Binding activity of humanized antibodies to cell surface CEA proteins of different species

| Antibodies | $EC_{50}$ (nM) MKN45 | cynoCEA-CHO | CEACAM1-CHO |
|---|---|---|---|
| Hu63-13 | 2.93 | 1.71 | No binding |
| Hu47-14 | 4.19 | 2.70 | No binding |
| Hu67-14 | 1.58 | 2.89 | No binding |
| Hu103-32 | 1.79 | 1.24 | No binding |
| Sanofi | 2.64 | 17.27 | No binding |
| Lmab | 2.45 | No binding | No binding |

The results of the binding activity of other humanized antibodies to cell surface CEA proteins (MKN45 and cyno-CEA-CHO) are shown in Table 18 below:

TABLE 18

Binding activity of humanized antibodies to cell surface CEA proteins

| | $EC_{50}$ (nM) | | | $EC_{50}$ (nM) | |
|---|---|---|---|---|---|
| Antibodies | MKN45 | cynoCEA-CHO | Antibodies | MKN45 | cynoCEA-CHO |
| Hu103-1 | 2.37 | 2.49 | Hu47-6 | 2.50 | 0.30 |
| Hu103-2 | 2.18 | 1.26 | Hu47-10 | 2.27 | 0.27 |
| Hu103-3 | 1.91 | 1.18 | Hu63-1 | 4.23 | 1.24 |
| Hu103-4 | 2.62 | 1.32 | Hu63-2 | 3.73 | 2.64 |
| Hu103-5 | 2.38 | 1.47 | Hu63-3 | 3.56 | 2.01 |
| Hu103-6 | 1.27 | 1.56 | Hu63-4 | 5.18 | 1.95 |
| Hu103-7 | 2.20 | 1.62 | Hu63-5 | 3.70 | 2.14 |
| Hu103-9 | 2.95 | 1.61 | Hu63-6 | 3.71 | 2.88 |
| Hu103-10 | 2.23 | 1.00 | Hu63-8 | 3.24 | 2.43 |
| Hu103-11 | 2.71 | 0.92 | Hu63-9 | 4.87 | 2.47 |
| Hu103-12 | 2.38 | 1.08 | Hu63-10 | 4.95 | 1.88 |
| Hu103-13 | 2.53 | 1.01 | Hu63-11 | 4.35 | 2.29 |
| Hu103-14 | 2.41 | 1.37 | Hu63-12 | 4.04 | 2.23 |
| Hu103-15 | 2.13 | 1.36 | Hu67-1 | 2.46 | 4.57 |
| Hu103-17 | 2.92 | 1.52 | Hu67-4 | 3.25 | 3.06 |
| Hu103-18 | 2.75 | 0.89 | Hu67-5 | 2.86 | 3.50 |
| Hu103-19 | 2.42 | 0.96 | Hu67-7 | 3.88 | 7.20 |
| Hu103-20 | 2.19 | 0.98 | Hu67-9 | 3.75 | 3.72 |
| Hu103-21 | 1.34 | 1.17 | Hu67-10 | 3.19 | 5.37 |
| Hu103-22 | 3.64 | 1.02 | Hu67-11 | 2.26 | 4.66 |
| Hu103-23 | 2.90 | 0.93 | Hu67-12 | 3.20 | 5.31 |

The experimental results show that the screened humanized antibodies in the present disclosure maintained similar binding activity to that of murine antibodies, and all could be bound with human CEA proteins on the cell surface; and that the screened humanized antibodies in the present disclosure could be bound to monkey CEA proteins on the cell surface, and the binding activity of the humanized antibodies to the monkey CEA proteins was better than that of the positive control antibody.

Test Example 2: Experiment on Competition with Soluble CEA (sCEA)

In order to test whether the antibodies were also preferentially bound to CEA on the cell membrane surface in the presence of sCEA, a gradient-diluted antibody and certain solubility of sCEA (5 μg/mL) were pre-incubated for 30 min, and then MKN45 cells were harvested and seeded in a 96-well plate. The gradient-diluted antibody and the pre-incubated mixed solution of the antibody and sCEA was added into each well. The plate was incubated at 4° C. for 60 min and centrifuged, and the supernatant was removed. The cells were washed twice with pre-cooled PBS containing FBS at final concentration 10%. 50 μL of 1:200 diluted secondary antibody Alexa Fluor@488 goat anti-human IgG (H+L) (Lifetechologies, Cat #A11013) was added. The plate was incubated at 4° C. for 45 min in the dark and centrifuged, and the supernatant was removed. The cells were washed twice with 250 μL of pre-cooled PBS with FBS at final concentration 10%. 100 μL of pre-cooled PBS was added to each well to resuspend the cells. The suspension was analyzed by a flow cytometer (FACS) (BD, FACSverse) for fluorescence signal values. If the ratio of the signal value obtained in the absence of sCEA to that obtained in the presence of sCEA is less than 2 for each concentration of the antibody, it indicates that the binding curve of the antibody do not greatly change in the presence of sCEA, and that the antibody still preferentially binds to CEA on the cell membrane surface. The experimental results are shown in Tables 19 and 20, wherein the ratios of the fluorescence signal value obtained in the absence of sCEA to that obtained in the presence of sCEA for different concentrations of Hu63-13, Hu47-14, Hu67-14, Hu103-32 and positive control Lmab antibodies are shown in Table 19 below, and the maximum ratios of the fluorescence signal value obtained in the absence of sCEA to that obtained in the presence of sCEA are shown in Table 20 below:

TABLE 19

Ratios of fluorescence signal value obtained in the absence of sCEA to that obtained in the presence of sCEA for humanized antibodies

| Antibody | Ratio of fluorescence signal values | | | | |
|---|---|---|---|---|---|
| concentration (μg/mL) | Hu63-13 | Hu47-14 | Hu67-14 | Hu103-32 | Lmab |
| 40 | 0.92 | 1.09 | 0.94 | 0.91 | 1.10 |
| 1.6 | 1.36 | 1.18 | 1.73 | 1.67 | 2.78 |
| 0.32 | 1.59 | 1.23 | 1.78 | 1.24 | 5.18 |
| 0.064 | 1.59 | 1.24 | 1.25 | 1.44 | 4.15 |
| 0.0128 | 1.43 | 1.09 | 1.50 | 1.28 | 2.72 |
| 0.00256 | 1.24 | 1.15 | 1.58 | 1.09 | 1.74 |
| 0.000512 | 1.02 | 1.07 | 1.08 | 0.86 | 1.20 |

TABLE 20

Maximum ratios of fluorescence signal value obtained in the absence of sCEA to that obtained in the presence of sCEA for antibodies

| Antibodies | Maximum ratio of fluorescence signals | Antibodies | Maximum ratio of fluorescence signals |
|---|---|---|---|
| Hu47-2 | 1.04 | Hu103-1 | 1.30 |
| Hu47-3 | 1.10 | Hu103-2 | 1.17 |
| Hu47-4 | 1.13 | Hu103-3 | 1.14 |
| Hu47-6 | 1.26 | Hu103-4 | 1.17 |
| Hu47-7 | 1.11 | Hu103-5 | 1.15 |
| Hu47-8 | 1.04 | Hu103-6 | 1.15 |
| Hu47-10 | 1.13 | Hu103-7 | 1.07 |
| Hu47-12 | 1.08 | Hu103-9 | 1.57 |
| Hu63-1 | 1.31 | Hu103-10 | 1.19 |
| Hu63-3 | 1.14 | Hu103-11 | 1.16 |
| Hu67-1 | 1.35 | Hu103-12 | 1.24 |
| Hu67-2 | 1.21 | Hu103-13 | 1.16 |
| Hu67-4 | 1.25 | Hu103-14 | 1.10 |
| Hu67-5 | 1.09 | Hu103-15 | 1.23 |
| Hu67-6 | 1.22 | Hu103-17 | 1.12 |
| Hu67-7 | 1.03 | Hu103-18 | 1.22 |
| Hu67-9 | 1.10 | Hu103-19 | 1.36 |
| Hu67-10 | 1.34 | Hu103-20 | 1.22 |
| Hu67-11 | 1.18 | Hu103-21 | 1.27 |
| Hu67-12 | 1.31 | Hu103-22 | 1.33 |
| Hu67-15 | 1.05 | Hu103-23 | 1.31 |
| mAb63 | 1.43 | mAb103 | 1.02 |
| mAb47 | 1.08 | Sanofi | 2.65 |

Experimental results show that the ratios of the fluorescence signal value obtained in the absence of sCEA to that obtained in the presence of sCEA for different concentrations of humanized antibodies Hu63-13, Hu47-14, Hu67-14 and Hu103-32 are all less than 2; for example, the maximum ratio for Hu63-13 is 1.59, while the maximum ratio for positive control Lmab is 5.18. The screened antibodies in the present disclosure are superior to the control antibody. The maximum ratios of the fluorescence signal value obtained in the absence of sCEA to that obtained in the presence of sCEA for the screened humanized antibodies in the present disclosure are all less than 2 and less than that of the positive control antibody, which indicates that the screened humanized antibodies in the present disclosure still preferentially bind to CEA on the cell membrane surface in the presence of sCEA and are superior to the positive control antibody.

Test Example 3: Determination of Affinity of Antibodies for Soluble CEA Using Biacore The affinity of a test humanized antibody for human and monkey soluble CEA was determined using a Biacore (GE, T200) instrument. According to the method in the instructions of a human antibody capture kit (GE, Cat #BR-1008-39), the human antibody capture antibody was covalently conjugated to a biosensor chip CM5 (GE, Cat #BR-1005-30) of the Biacore instrument to affinity-capture a certain amount of the test antibody, then a series of concentration gradients of soluble CEA antigens were allow to flow through the surface of the chip, and reaction signals were detected in real time using Biacore, so that an association and dissociation curve was obtained. After each cycle of dissociation was completed, the biochip was washed and regenerated with a regeneration solution prepared in the human antibody capture kit. The data obtained from the experiment were fitted with the (1:1) Langmuir model using BIAevaluation version 4.1 software to obtain affinity values. Since it is desirable that the binding activity of the screened antibodies in the present disclosure to CEA on the cell membrane surface is higher than that to the soluble CEA, lower affinity of the antibodies for soluble CEA is desired. The assay results of the affinity of the humanized antibodies for soluble CEA are shown in Table 21 below:

TABLE 21

Affinity of humanized antibodies for human soluble CEA

| | Human soluble CEA | | |
|---|---|---|---|
| Antibodies | ka (1/Ms) | kd (1/s) | KD (M) |
| Hu63-13 | 2.99E+04 | 4.31E−03 | 1.44E−07 |
| Hu47-14 | 1.31E+05 | 1.88E−01 | 1.43E−06 |
| Hu67-14 | 3.76E+04 | 8.59E−03 | 2.28E−07 |
| Hu103-32 | 3.33E+04 | 1.03E−03 | 3.11E−08 |
| Sanofi | 5.95E+04 | 3.08E−03 | 5.17E−08 |
| Lmab | 5.58E+04 | 3.31E−04 | 5.93E−09 |

The test results show that the humanized antibodies Hu63-13, Hu47-14 and Hu67-14 all have lower affinity for soluble CEA protein, significantly lower than the control antibodies Sanofi and Lmab. This indicates that Hu63-13, Hu47-14 and Hu67-14 are not easily neutralized by soluble CEA in blood in vivo, and a large amount of antibodies can bind to cells expressing CEA on the cell membrane surface.

Test Example 4: Endocytic Activity of Anti-CEA Antibody in CEA-Highly Expressing Cells MKN45

After the anti-CEA antibody conjugate in the present disclosure is endocytosed by cells, the conjugate can release toxin to kill the cells. Therefore, the endocytic activity of the CEA antibody in the CEA-expressing cells can promote ADC to exert activity. In order to evaluate the endocytic activity of humanized antibodies in MKN45 cells, MKN45 cells were plated in a 96-well plate (corning, Cat #3795) and cultured overnight; the humanized CEA antibodies Hu63-13, Hu47-14, Hu67-14 and Hu103-32 were pre-incubated the next day with iFL Green Human IgG Labeling Reagent (Invitrogen, Cat #Z25611) for 15 min, during which the iFL reagent would bind to the Fc of the humanized antibodies; then, the complexes of the antibodies and iFL were added to the cell culture plate, and the cell culture solution was removed after 6 h and 24 h; the cells were washed twice with PBS, digested and collected, and the intensity of fluorescent signals in the cells was detected by FACS. iFL bound on the Fc of the antibodies was brought into the cells after the antibodies were endocytosed, and the fluorescent signals could be detected only in an acid environment after the iFL was endocytosed by the cells; therefore, stronger signals detected indicate higher endocytotic activity of the antibodies. The endocytic activity of the humanized antibodies is shown in FIG. 1: all of the humanized antibodies can be endocytosed by MKN45 cells, and more antibodies were endocytosed over time.

Test Example 5: Cytotoxicity of ADCs to Cancer Cells with Different CEA Expression Levels Following conjugation of humanized CEA antibodies to toxin 2-A, cytotoxicity of each ADC to cancer cell lines with different CEA expression levels was evaluated. The CEA-highly expressing cells MKN45, the CEA-moderately expressing cells LS174T and the CEA-expressing negative cells HCT116 were plated in 96-well plates; gradient-diluted ADC samples were added to the cells the next day, and the cells were cultured at 37° C. for 5 days. 50 μL of Cell Titer-Glo reagent (Promega, Cat #G9242) was added to each well, and after incubation for 10 min in the dark, the luminescence signals were detected by a cell imaging detector (BioTek, Cytation5). An inhibition curve was plotted with the detection results using PRISM analysis software, and fitted to obtain an $IC_{50}$ value of the inhibitory activity of the ADC against cell proliferation. The cytotoxicity of each ADC is shown as follows:

TABLE 22

Cytotoxicity of ADCs to cells with different CEA expression levels

| | | $IC_{50}$ (nM) | | | $IC_{50}$ ratio | |
|---|---|---|---|---|---|---|
| ADC samples | DAR | MKN45 (with high CEA expression) | LS174T (with moderate CEA expression) | HCT116 (without CEA expression) | HCT116/ LS174T | HCT116/ MKN45 |
| Hu47-14-2-A | 6.6 | 6.58 | 10.3 | 106.3 | 10.32 | 16.16 |
| Hu63-13-2-A | 6.29 | 3.933 | 13.08 | 87.64 | 6.70 | 22.28 |
| Hu67-14-2-A | 6.41 | 3.331 | 9.236 | 71.83 | 7.78 | 21.56 |
| Hul03-32-2-A | 6.94 | 2.998 | 2.374 | 78.1 | 32.90 | 26.05 |
| Lmab-CL2A-SN38 | 7 | 0.665 | 0.3456 | 0.4276 | 1.24 | 0.64 |
| Hu63-13-2-A | 3.97 | 34.02 | 19.76 | 165.1 | 8.36 | 4.85 |

TABLE 22-continued

Cytotoxicity of ADCs to cells with different CEA expression levels

| ADC samples | DAR | $IC_{50}$ (nM) MKN45 (with high CEA expression) | LS174T (with moderate CEA expression) | HCT116 (without CEA expression) | $IC_{50}$ ratio HCT116/ LS174T | HCT116/ MKN45 |
|---|---|---|---|---|---|---|
| Hu67-14-2-A | 4.28 | 9.388 | 15.58 | 71.95 | 4.62 | 7.66 |
| Hul03-32-2-A | 4.8 | 2.863 | 3.076 | 83.58 | 27.17 | 29.19 |
| Lmab-CL2A-SN38 | 4.15 | 1.595 | 0.6618 | 1.059 | 1.60 | 0.66 |

The ADC molecules conjugated to toxin 2-A shows CEA expression level dependent cytotoxicity: the higher the CEA expression level, the more toxic the ADC to cells. Meanwhile, ADCs with high DAR values and low DAR values have stronger cytotoxicity to the CEA-expressing cells and weaker cytotoxicity to CEA-non-expressing cells. The control ADC molecule Lmab-CL2A-SN38 have similar cytotoxicity to all three cell lines, showing non-specific cytotoxicity. The $IC_{50}$ ratio can indirectly reflect the safety of an ADC molecule. A greater ratio indicates that the ADC molecule is less toxic to cells that do not express CEA and may be safer in vivo.

Test Example 6: Bystander Effect and Cytotoxicity of ADCs

After an ADC is endocytosed into a cell, the toxin is released from the ADC to produce a toxic effect on the cell. After death and lysis of the cell, the toxin is released out of the cell and can further enter nearby cells to produce toxic effects on them.

In order to evaluate the bystander effect and cytotoxicity of the ADC, the CEA-highly expressing cell line MKN45 and the CEA-expressing negative cell line HCT116 were cultured in a 6-well cell culture plate for 24 h, and then an ADC sample was added at a final concentration of 4 nM. The cells were cultured in a cell incubator at 37° C. for another 5 days.

The cells were digested with pancreatin and collected, and CEA Monoclonal Antibody FITC (ThermoFisher, Cat #MA1-80578) was added at a final concentration of 10 μg/mL. The cells were incubated on ice in the dark for 1 h, washed twice with PBS, and counted using a flow cytometer. Cells that produced fluorescent signals were CEA-expressing MKN45 cells and cells that did not produce a signal were non-CEA-expressing HCT116 cells.

Figure 2:
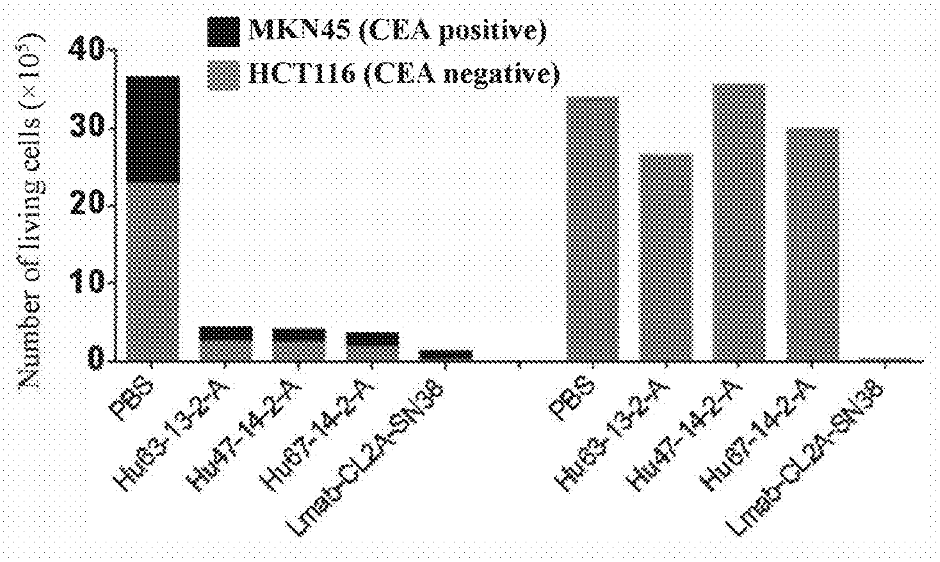
FIG. 2 shows the bystander effect and cytotoxicity of ADC molecules; the data show that all the ADC molecules have strong bystander effect and cytotoxicity, and when MKN45 and HCT116 are co-cultured, the ADC molecules can inhibit the proliferation of both the types of cells, while when the HCT116 is cultured alone, the ADC molecules coupled with 2-A are fundamentally not toxic to the cells.

The results of bystander effect and cytotoxicity of ADC samples are shown in FIG. 2: all the ADC molecules have strong bystander effects and cytotoxicity. When MKN45 and HCT116 were co-cultured, the ADC molecules can inhibit the proliferation of both the types of cells, while when the HCT116 was cultured alone, the ADC molecules coupled with 2-A are fundamentally not toxic to the cells. The control ADC molecule Lmab-CL2A-SN38 is very toxic to both cells co-cultured and cultured alone.

The DAR values of the ADC molecules used in the experiments are as follows: Hu63-13-2-A DAR 6.29; Hu47-14-2-A DAR 6.6; Hu67-14-2-A DAR 6.41; Lmab-CL2A-SN38 DAR 7.0.

Test Example 7: In Vivo Inhibitory Activity of ADC Molecules Against Tumors

The in vivo efficacy of the ADC molecules was evaluated using LS174T and MKN45 xenograft tumor models. BALB/c nude mice (SPF grade, Shanghai Slac Laboratory Animal Co., Ltd., certificate no.: 201833814, license no.: SCXK (Jiangsu) 2016-0010) were housed in a 12/12 hour light/dark cycle at a temperature of 23±1° C. with humidity at 40-50%, with food (standard sterilized feed for mice) and water ad libitum. The mice were acclimatized for 10 days in a laboratory environment before the start of the experiment and then inoculated subcutaneously on the right flank with LS174T cells ($5\times10^5$ cells/mouse) or MKN45 cells ($4\times10^6$ cells/mouse). Tumors were allowed to grow to a size of about 150 $mm^3$, and then the mice were randomized into groups of 8. After grouping, the mice in the experimental groups were intraperitoneally injected with ADC samples in a dose of 1 mg/kg or 3 mg/kg, and those in the blank control group were intraperitoneally injected with PBS, only once. The sizes of the tumors on the mice were observed, measured and recorded. Tumor volume (V) was calculated as: $V=1/2\times L_{long}\times L_{short}^2$; relative tumor volume (RTV)=$V_T/V_0$; tumor inhibition rate (%)=$(C_{RTV}-T_{RTV})/C_{RTV}$ (%); wherein $V_0$ and $V_T$ are the tumor volumes at the beginning and end of the experiment, respectively; and $C_{RTV}$ and $T_{RTV}$ are the relative tumor volumes of the blank control group and the experimental groups, respectively, at the end of the experiment.

Figure 3:
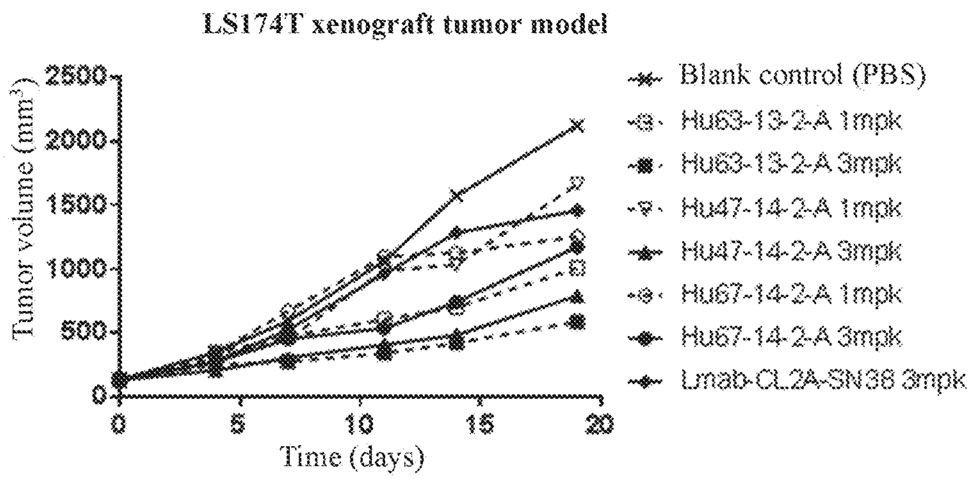
FIG. 3 shows the effect of ADC molecules on tumor volume in an LS174T xenograft tumor model; the data show that all the ADC molecules have effects in inhibiting the increase of tumors in volume compared to the control group (PBS), and the inhibitory effects on tumors in the 3-mpk groups are better than those in the 1-mpk groups; among the 3-mpk groups, Hu63-13-2-A has the best inhibitory effect on tumors, followed by Hu47-14-2-A and then Hu67-14-2-A, and Lmab-CL2A-SN38 has the worst inhibitory effect on tumors.
Figure 4:
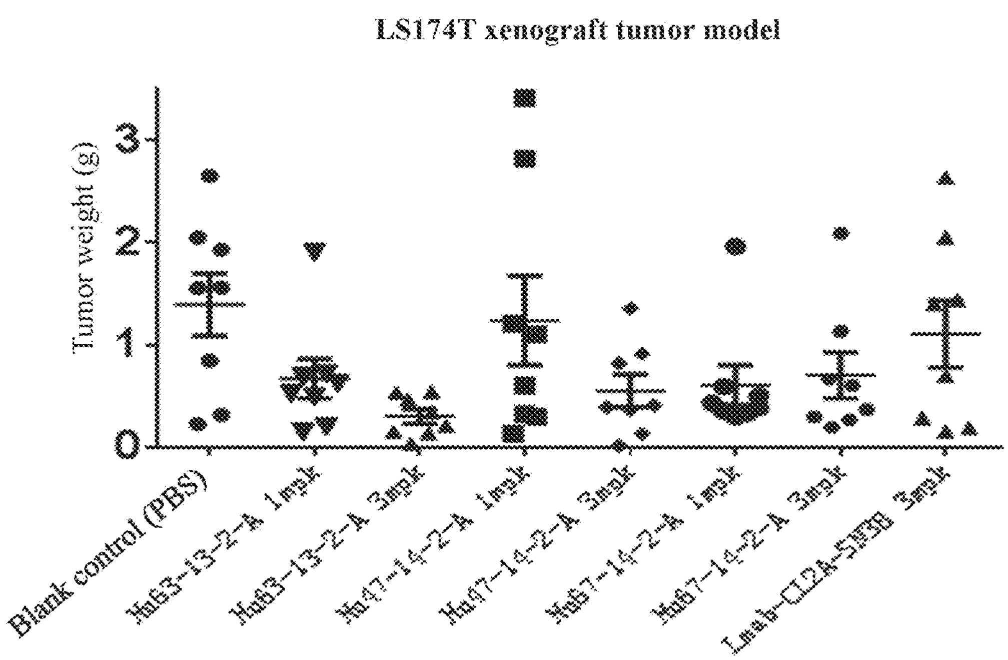
FIG. 4 shows the effect of ADC molecules on tumor weight in an LS174T xenograft tumor model; the data show that all the ADC molecules have effects in inhibiting the increase of tumors in weight at both low and high doses compared to the control group (PBS); among the 3-mpk groups, Hu63-13-2-A has the best inhibitory effect on tumors, followed by Hu47-14-2-A and then Hu67-14-2-A, and Lmab-CL2A-SN38 has the worst inhibitory effect on tumors.
Figure 5:
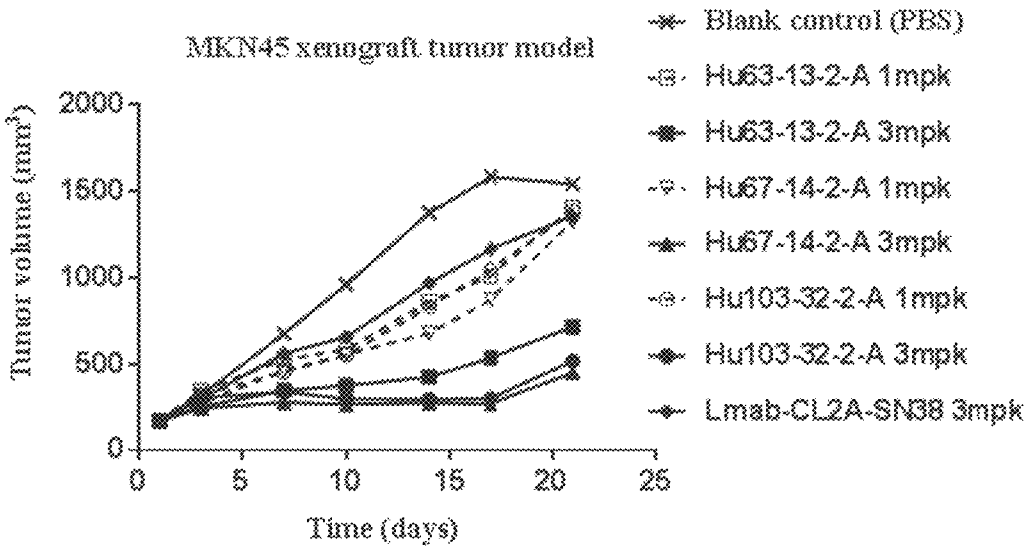
FIG. 5 shows the effect of ADC molecules on tumor volume in an MKN45 xenograft tumor model; the data show that all the ADC molecules have effects in inhibiting the increase of tumors in volume compared to the control group (PBS), and the inhibitory effects on tumors in the 3-mpk groups are better than those in the 1-mpk groups; among the 3-mpk groups, Hu67-14-2-A has the best inhibitory effect on tumors, followed by Hul03-32-2-A and then Hu63-13-2-A, and Lmab-CL2A-SN38 has the worst inhibitory effect on tumors.
Figure 6:
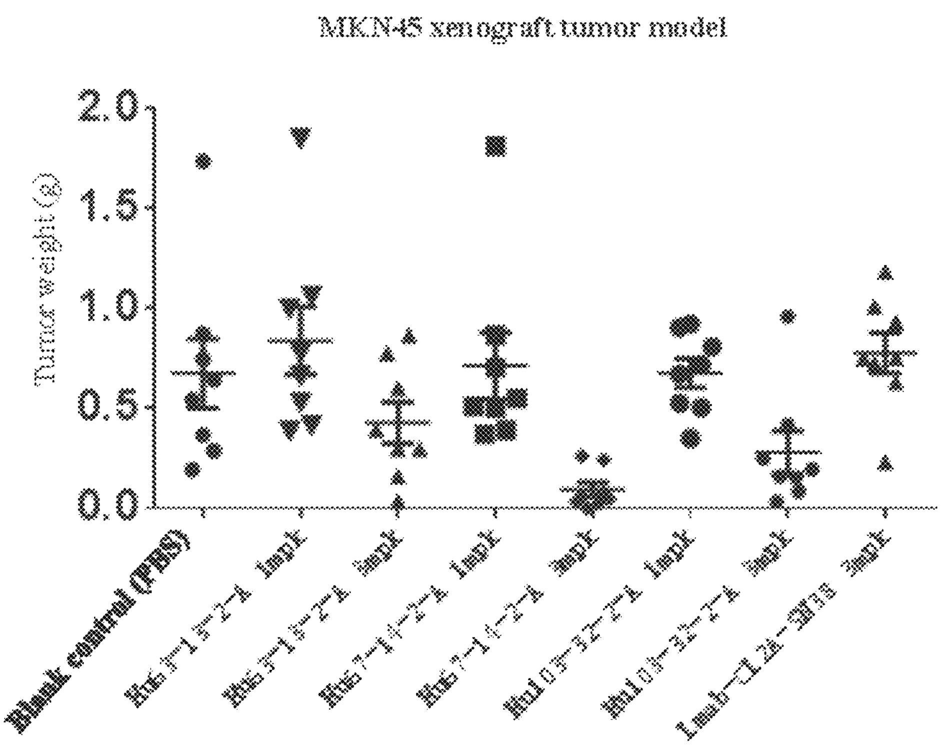
FIG. 6 shows the effect of ADC molecules on tumor weight in an MKN45 xenograft tumor model; the data show that all the ADC molecules have effects in inhibiting the increase of tumors in weight at both low and high doses compared to the control group (PBS); among the 3-mpk groups, Hu67-14-2-A has the best inhibitory effect on tumors, followed by Hu103-32-2-A and then Hu63-13-2-A, and Lmab-CL2A-SN38 has the worst inhibitory effect on tumors.

In terms of the in vivo efficacy, compared to PBS in the control group, all the ADC molecules have effects in inhibiting the increase of tumors in volume and weight, in a dose-dependent manner to some extent: the inhibitory effects on tumors in the 3-mpk groups are better than those in the 1-mpk groups. In the LS174T xenograft tumor model, the results are shown in FIG. 3 (changes in tumor volume) and FIG. 4 (tumor weight on the last day): among the 3-mpk groups, Hu63-13-2-A has the best inhibitory effect on tumors, followed by Hu47-14-2-A and then Hu67-14-2-A, and Lmab-CL2A-SN38 has the worst inhibitory effect on tumors. In the MKN45 xenograft tumor model, the results are shown in FIG. 5 (changes in tumor volume) and FIG. 6 (tumor weight on the last day): among the 3-mpk groups, Hu67-14-2-A has the best inhibitory effect on tumors, followed by Hu103-32-2-A and then Hu63-13-2-A, and Lmab-CL2A-SN38 has the worst inhibitory effect on tumors.

The in vivo tumor inhibition rates of the ADC molecules are shown in Tables 23 and 24 below: the tumor inhibition rates of ADCs show a significant dose effect; specifically, in the LS174T xenograft tumor model, among the low-dose groups (1 mpk), Hu63-13-2-A has the highest tumor inhibition rate (55.95%), followed by Hu67-14-2-A (43.71%), and Hu47-14-2-A has the lowest tumor inhibition rate (23.04%); among the high-dose groups (3 mpk), Hu63-13-2-A has the highest tumor inhibition rate (77.13%), followed by Hu47-14-2-A (66.87%) and then Hu67-14-2-A (47.66%), and Lmab-CL2A-SN38 has the lowest tumor inhibition rate (33.44%); in the MKN45 xenograft tumor model, among the low-dose groups (1 mpk), Hu67-14-2-A has the highest tumor inhibition rate (15.88%), followed by Hu103-32-2-A (11.39%), and Hu63-13-2-A has the lowest tumor inhibition rate (9.89%); among the high-dose groups (3 mpk), Hu67-14-2-A has the highest tumor inhibition rate (79.51%), followed by Hu103-32-2-A (74.66%) and then Hu63-13-2-A (60.26%), and Lmab-CL2A-SN38 has the lowest tumor inhibition rate (13.51%).

TABLE 23

In vivo tumor inhibition rates of ADCs

| Group | DAR | Dose | Tumor inhibition rate (%) | P value (compared to control group) |
|---|---|---|---|---|
| Blank control group | NA | NA | NA | NA |
| Hu63-13-2-A | 6.3 | 1 mpk | 55.95%* | 0.0159 |
| Hu63-13-2-A | 6.3 | 3 mpk | 77.13%** | 0.0013 |
| Hu47-14-2-A | 6.6 | 1 mpk | 23.04% | 0.4590 |
| Hu47-14-2-A | 6.6 | 3 mpk | 66.87%** | 0.0052 |
| Hu67-14-2-A | 6.13 | 1 mpk | 43.71% | 0.0561 |
| Hu67-14-2-A | 6.13 | 3 mpk | 47.66% | 0.0794 |
| Lmab-CL2A-SN38 | 7.0 | 3 mpk | 33.44% | 0.1791 |

Note:
*indicates P < 0.05,
**indicates P < 0.01, and
NA indicates not applicable.

TABLE 24

In vivo tumor inhibition rates of ADCs in MKN45 xenograft tumor model

| Group | DAR | Dose | Tumor inhibition rate (%) | P value (compared to control group) |
|---|---|---|---|---|
| Blank control group | NA | NA | NA | NA |
| Hu63-13-2-A | 6.3 | 1 mpk | 9.89% | 0.6492 |
| Hu63-13-2-A | 6.3 | 3 mpk | 60.26%* | 0.0124 |
| Hu67-14-2-A | 6.13 | 1 mpk | 15.88% | 0.5336 |
| Hu67-14-2-A | 6.13 | 3 mpk | 79.51%** | 0.0087 |
| Hu103-32-2-A | 6.94 | 1 mpk | 11.39% | 0.5219 |
| Hu103-32-2-A | 6.94 | 3 mpk | 74.66%** | 0.0033 |
| Lmab-CL2A-SN38 | 7.0 | 3 mpk | 13.51% | 0.4980 |

Note:
*indicates P < 0.05,
**indicates P < 0.01, and
NA indicates not applicable.

Test Example 8: In Vivo Pharmacokinetic Study of ADC Molecules

An In vivo pharmacokinetic study was performed in SD rats. SD rats (Shanghai Sippr-BK Laboratory Animal Co. Ltd.) were randomized into groups of 3, and the drugs were administered by intravenous injection at a dose of 3 mg/kg. 0.3 mL of whole blood samples were collected from the administration groups at the following time points: before administration, and 5 min, 8 h, 1 day, 2 days, 4 days, 7 days, 10 days, 14 days, 21 days and 28 days after administration, and no anticoagulant was added. The collected whole blood sample were left at 4° C. for 30 min and centrifuged at 1000 g for 15 min, and the supernatant was collected, placed in an EP tube and stored at −80° C. The blood concentration in serum was determined by ELISA, and the pharmacokinetic parameters were calculated for the test drugs by Winnolin software. The results are shown as follows:

TABLE 25

In vivo pharmacokinetic parameters of ADC molecules

| Samples | Hu63-13-2-A (DAR 6.8) | | Hu47-14-2-A (DAR 6.72) | | Hu67-14-2-A (DAR 6.7) | | Hul03-32-2-A (DAR 6.91) | |
|---|---|---|---|---|---|---|---|---|
| | Intact ADC | Antibodies | Intact ADC | Antibodies | Intact ADC | Antibodies | Intact ADC | Antibodies |
| Parameters | Average value | Average value | Average value | Average value | Average value | Average value | Average value | Average value |
| t1/2(h) | 169.7 | 192.7 | 158.5 | 188.8 | 170.8 | 180.6 | 135.19 | 157.87 |
| t1/2(d) | 7.1 | 8.0 | 6.6 | 7.9 | 7.1 | 7.5 | 5.63 | 6.58 |
| Cmax(ug/ml) | 62.9 | 67.6 | 51.5 | 55.2 | 50.8 | 49.6 | 64.94 | 66.35 |
| AUC 0-t (ug/ml * h) | 4280 | 4949 | 3283 | 3444 | 4037 | 4038 | 3609 | 3235 |
| AUC 0-∞ (ug/ml * h) | 4600 | 5451 | 3456 | 3741 | 4309 | 4356 | 3699 | 3357 |
| Vz(ml/kg) | 159.8 | 153.0 | 198.3 | 218.8 | 171.9 | 179.9 | 160.09 | 206.29 |
| CL(ml/day/kg) | 15.7 | 13.2 | 20.9 | 19.3 | 16.8 | 16.6 | 19.70 | 21.75 |
| MRT 0-∞ (h) | 212.1 | 239.0 | 184.7 | 216.6 | 226.6 | 237.7 | 144.63 | 160.14 |

All the ADC molecules have good pharmacokinetic properties, and the half-lives of the antibodies are slightly longer than those of the ADC molecules. The in vivo half-life of Hu63-13-2-A is 7.1 days, and the half-life of the antibody is 8 days; the in vivo half-life of Hu47-14-2-A is 6.6 days, and the half-life of the antibody is 7.9 days; the in vivo half-life of Hu67-14-2-A is 7.1 days, and the half-life of the antibody is 7.5 days; the in vivo half-life of Hu103-32-2-A is 5.63 days, and the half-life of the antibody is 6.58 days.

Test Example 9: In Vitro Stability Study of ADC Molecules in Plasma

In order to evaluate the in vitro stability of the ADC molecules in plasma, the ADC molecules were added to human and monkey plasma at a concentration of 100 μg/mL, and the mixtures were let stand at 37° C. for 21 days. Mixture samples were taken once a week, and analyzed by LC/MS/MS (Shimadzu, LC-30AD ultra high performance liquid chromatography system; Applied Biosystems, API4000 triple quadrupole tandem mass spectrometer) for the free-toxin content in the plasma. The detection results are as follows:

TABLE 26

| Percentages of toxins in plasma | | | | | | | | | | | | |
|---|---|---|---|---|---|---|---|---|---|---|---|---|
| | Percentages of toxins in plasma (%) | | | | | | | | | | | |
| | Hu63-13-2-A (DAR 7.24) | | | Hu47-14-2-A (DAR 6.85) | | | Hu67-14-2-A (DAR 6.7) | | | Hul03-32-2-A (DAR 6.05) | | |
| Days | BSA | Human | Monkey | BSA | Human | Monkey | BSA | Human | Monkey | BSA | Human | Monkey |
| 0 | 0 | 0 | 0 | 0 | 0 | 0 | 0 | 0 | 0 | 0 | 0 | 0 |
| 7 | 0 | 0 | 0 | 0 | 0 | 0 | 0 | 0 | 0 | 0 | 0.93 | 0.38 |
| 14 | 0 | 0.21 | 0 | 0 | 0.28 | 0 | 0 | 0.18 | 0.21 | 0 | 0.78 | 0.92 |
| 21 | 0 | 0.32 | 0.4 | 0 | 0.34 | 0.29 | 0 | 0.4 | 0.24 | 0 | 1.13 | 0.96 |

The detection result 0 indicates that the free-toxin content in the plasma is below the lower limit of detection and cannot be detected. All the ADC molecules have good stability in the plasma of human and monkey. The free-toxin content in the plasma of human and monkey for Hu63-13-2-A was 0.32% and 0.4%, respectively, after incubation at 37° C. for 21 days; the free-toxin content in the plasma of human and monkey for Hu47-14-2-A was 0.34% and 0.29%, respectively; the free-toxin content in the plasma of human and monkey for Hu67-14-2-A was 0.4% and 0.24%, respectively; the free-toxin content in the plasma of human and monkey for Hu103-32-2-A was 1.13% and 0.96%, respectively.

Test Example 10: Test for Inhibition of In Vitro Proliferation of Tumor Cells by Compounds I. Purpose This experiment was intended to test the inhibitory activity of the pharmaceutical compounds of the present disclosure against the in vitro proliferation of U87MG cells (Cell Bank, Chinese Academy of Sciences, Cat #TCHu138) and SK-BR-3 tumor cells (human breast cancer cells, ATCC, Cat #HTB-30). The cells were treated in vitro with a compound at different concentrations. After 6 days of culture, the proliferation of cells was tested using CTG (CellTiter-Glo® Luminescent Cell Viability Assay, Promega, Cat #G7573) reagents, and the in vitro activity of the compound was evaluated according to $IC_{50}$ value.

II. Method

The test for the inhibition of the in vitro proliferation of U87MG cells was taken as an example to illustrate the method of the present invention for testing the inhibitory activity of the compounds of the present invention against the in vitro proliferation of tumor cells. The method was also applicable to, but not limited to, the test for the inhibitory activity against the in vitro proliferation of other tumor cells.

1. Cell culture: U87MG and SK-BR-3 cells were cultured in EMEM medium (GE, Cat #SH30024.01) containing 10% FBS and McCoy's 5A medium (Gibco, Cat #16600-108) containing 10% FBS, respectively.
2. Cell preparation: U87MG and SK-BR-3 cells growing at log phase were washed once with PBS (phosphate buffer, Shanghai BasalMedia Technologies Co., LTD.) and then digested with 2-3 mL of trypsin (0.25% Trypsin-EDTA (1×), Gibico, Life Technologies) for 2-3 min. After the cells were completely digested, 10-15 mL of cell culture media were added to elute the digested cells. The mixtures were centrifuged at 1000 rpm for 5 min, and the supernatants were discarded. Then the cells were resuspended in 10-20 mL of cell culture media to give single-cell suspensions.
3. Cell plating: the U87MG and SK-BR-3 single-cell suspensions were each well mixed and adjusted with cell culture media to cell densities of $2.75\times10^3$ cells/mL and $8.25\times10^3$ cells/mL, respectively. The adjusted cell suspensions were each well mixed and added to 96-well cell culture plates at 180 μL/well. Only 200 μL of media was added to the peripheral wells of the 96-well plate. The plate was incubated in an incubator for 24 h (37° C., 5% $CO_2$).
4. Compound preparation: the compound was dissolved in DMSO (dimethyl sulfoxide, Shanghai Titan Scientific Co., Ltd.) to prepare a stock solution at an initial concentration of 10 mM.

Small molecule compounds were prepared at an initial concentration of 500 nM as follows.

Different test samples at 100 μM (30 μL) were added to the first column of a 96-well U-bottom plate, and 20 μL of DMSO was added to each well of the second column through the eleventh column. The samples in the first column (10 μL) were added to the 20 μL of DMSO in the second column, and the mixtures were well mixed. 10 μL of mixtures were added to the third column, and so on to the tenth column. The drugs in the plate (5 μL per well) were transferred to EMEM media (95 μL), and the mixtures were well mixed for later use.

ADCs were prepared at an initial concentration of 10 nM or 500 nM as follows.

Different test samples at 100 nM or 5 μM (100 μL) were added to the first column of a 96-well plate, and 100 μL of PBS was added to each well of the second column through the eleventh column. The samples in the first column (50 μL) were added to the 100 μL of PBS in the second column, and the mixtures were well mixed. 50 μL of mixtures were added to the third column, and so on, by 3-fold dilution, to the tenth column.

5. Sample adding: the test samples prepared at different concentrations (20 μL) were added to the culture plate, with two duplicate wells set for each sample. The plate was incubated in an incubator for 6 days (37° C., 5% $CO_2$).
6. Color developing: the 96-well cell culture plate was taken out, and 90 μL of CTG solution was added to each well, followed by 10 min of incubation at room temperature.
7. Plate reading: the 96-well cell culture plate was taken out and tested in a microplate reader (BMG labtech, PHERAstar FS) for chemiluminescence.

III. Data Analysis

Data were processed and analyzed using Microsoft Excel and Graphpad Prism 5. The experimental results are shown in the table below.

TABLE 27

$IC_{50}$ values of the small molecule fragments of the present disclosure in inhibiting in vitro proliferation of SK-BR-3 cells and U87 cells

| | $IC_{50}$ (nM) | |
|---|---|---|
| Compound No. | SK-BR-3 | U87 |
| Shorter retention time 1-B | 0.33 | 0.86 |
| Longer retention time 1-A | 8.11 | 2.31 |

Conclusion: the small molecular fragments of the present disclosure have significant inhibitory activity against the proliferation of SK-BR-3 cells and U87 cells, and the chiral centers have certain influence on the inhibitory activity of the compounds.

The invention claimed is:

1. An antibody drug conjugate, comprising: an anti-CEA antibody or an antigen-binding fragment thereof conjugated to a toxin drug by a linker, wherein the anti-CEA antibody or the antigen-binding fragment thereof comprises a heavy chain variable region and a light chain variable region, wherein:

(i) the heavy chain variable region comprises a HCDR1, a HCDR2 and a HCDR3 set forth in SEQ ID NO: 21, SEQ ID NO: 22 and SEQ ID NO: 23, respectively, and the light chain variable region comprises a LCDR1, a LCDR2 and a LCDR3 set forth in SEQ ID NO: 24, SEQ ID NO: 25 and SEQ ID NO: 26, respectively; or the heavy chain variable region comprises a HCDR1, a HCDR2 and a HCDR3 set forth in SEQ ID NO: 21, SEQ ID NO: 47 and SEQ ID NO: 23, respectively, and the light chain variable region comprises a LCDR1, a LCDR2 and a LCDR3 set forth in SEQ ID NO: 24, SEQ ID NO: 25 and SEQ ID NO: 26, respectively;

(ii) the heavy chain variable region comprises a HCDR1, a HCDR2 and a HCDR3 set forth in SEQ ID NO: 15, SEQ ID NO: 16 and SEQ ID NO: 17, respectively, and the light chain variable region comprises a LCDR1, a LCDR2 and a LCDR3 set forth in SEQ ID NO: 18, SEQ ID NO: 19 and SEQ ID NO: 20, respectively; or the heavy chain variable region comprises an HCDR1, a HCDR2 and a HCDR3 set forth in SEQ ID NO: 15, SEQ ID NO: 38 and SEQ ID NO: 17, respectively, and the light chain variable region comprises a LCDR1, a LCDR2 and a LCDR3 set forth in SEQ ID NO: 18, SEQ ID NO: 19 and SEQ ID NO: 20, respectively;

(iii) the heavy chain variable region comprises a HCDR1, a HCDR2 and a HCDR3 set forth in SEQ ID NO: 27, SEQ ID NO: 28 and SEQ ID NO: 29, respectively, and the light chain variable region comprises a LCDR1, a LCDR2 and a LCDR3 set forth in SEQ ID NO: 30, SEQ ID NO: 31 and SEQ ID NO: 32, respectively; or (iv) the heavy chain variable region comprises a HCDR1 and a HCDR3 set forth in SEQ ID NO: 33 and SEQ ID NO: 34, respectively, and a HCDR2 set forth in SEQ ID NO: 16 or SEQ ID NO: 38; the light chain variable region comprises a LCDR1 and a LCDR3 set forth in SEQ ID NO: 35 and SEQ ID NO: 37, respectively, and a LCDR2 set forth in SEQ ID NO: 36 or SEQ ID NO: 64.

2. The antibody drug conjugate according to claim 1, wherein the anti-CEA antibody is a murine antibody, a chimeric antibody or a humanized antibody.

3. The antibody drug conjugate according to claim 1, wherein the anti-CEA antibody or the antigen-binding fragment thereof comprises a heavy chain variable region and a light chain variable region, wherein:

(a) the heavy chain variable region has an amino acid sequence set forth in SEQ ID NO: 9; and/or the light chain variable region has an amino acid sequence set forth in SEQ ID NO: 10; or (b) the heavy chain variable region has an amino acid sequence set forth in SEQ ID NO: 7; and/or the light chain variable region has an amino acid sequence set forth in SEQ ID NO: 8; or (c) the heavy chain variable region has an amino acid sequence set forth in SEQ ID NO: 11; and/or the light chain variable region has an amino acid sequence set forth in SEQ ID NO: 12; or (d) the heavy chain variable region has an amino acid sequence set forth in SEQ ID NO: 13; and/or the light chain variable region has an amino acid sequence set forth in SEQ ID NO: 14.

4. The antibody drug conjugate according to claim 1, wherein the anti-CEA antibody or the antigen-binding fragment thereof comprises a heavy chain variable region and a light chain variable region, wherein:

(e) the heavy chain variable region has an amino acid sequence set forth in SEQ ID NO: 48, 49, 50, 51 or 52, or an amino acid sequence having at least 90% identity to any one amino acid sequence set forth in SEQ ID NO: 48, 49, 50, 51 or 52; and/or the light chain variable region has an amino acid sequence set forth in SEQ ID NO: 53, 54 or 55, or an amino acid sequence having at least 90% identity to any one amino acid sequence set forth in SEQ ID NO: 53, 54 or 55; or (f) the heavy chain variable region has an amino acid sequence set forth in SEQ ID NO: 39, 40, 41 or 42, or an amino acid sequence having at least 90% identity to any one amino acid sequence set forth in SEQ ID NO: 39, 40, 41 or 42; and/or the light chain variable region has an amino acid sequence set forth in SEQ ID NO: 43, 44, 45 or 46, or an amino acid sequence having at least 90% identity to any one amino acid sequence set forth in SEQ ID NO: 43, 44, 45 or 46; or (g) the heavy chain variable region has an amino acid sequence set forth in SEQ ID NO: 56, 57 or 58, or an amino acid sequence having at least 90% identity to any one amino acid sequence set forth in SEQ ID NO: 56, 57 or 58; and/or the light chain variable region has an amino acid sequence set forth in SEQ ID NO: 59, 60, 61, 62 or 63, or an amino acid sequence having at least 90% identity to any one amino acid sequence set forth in SEQ ID NO: 59, 60, 61, 62 or 63; or (h) the heavy chain variable region has an amino acid sequence set forth in SEQ ID NO: 65, 66, 67 or 68, or an amino acid sequence having at least 90% identity to any one amino acid sequence set forth in SEQ ID NO: 65, 66, 67 or 68; and/or the light chain variable region has an amino acid sequence set forth in SEQ ID NO: 69, 70, 71, 72, 73, 74, 75 or 76, or an amino acid sequence having at least 90% identity to any one amino acid sequence set forth in SEQ ID NO: 69, 70, 71, 72, 73, 74, 75 or 76.

5. The antibody drug conjugate according to claim 1, wherein the anti-CEA antibody is a humanized antibody comprising a framework region derived from a human antibody or a framework region variant thereof, and the framework region variant is selected from any one of the following (i) to (l):

(i) a framework region of the light chain variable region comprising the LCDR1, the LCDR2 and the LCDR3 having sequences set forth in SEQ ID NO: 24, SEQ ID NO: 25 and SEQ ID NO: 26, respectively, comprising one or more amino acid reverse mutations selected from the group consisting of 2V, 42G, 44V and 71Y, and/or a framework region of the heavy chain variable region comprising the HCDR1 having a sequence set forth in SEQ ID NO: 21, the HCDR2 having a sequence set forth in SEQ ID NO: 22 or SEQ ID NO: 47 and the HCDR3 having a sequence set forth in SEQ ID NO: 23, comprising one or more amino acid reverse mutations selected from the group consisting of 48I, 66K, 67A, 69L, 71V, 73K, 82F and 82A R;

(i) a framework region of the light chain variable region comprising the LCDR1, the LCDR2 and the LCDR3 having sequences set forth in SEQ ID NO: 18, SEQ ID NO: 19 and SEQ ID NO: 20, respectively, comprising one or more amino acid reverse mutations selected from the group consisting of 46P, 47W, 49Y, 70S and 71Y, and/or a framework region of the heavy chain variable region comprising the HCDR1 having a sequence set forth in SEQ ID NO: 15, the HCDR2 having a sequence set forth in SEQ ID NO: 16 or SEQ ID NO: 38 and the HCDR3 having a sequence set forth in SEQ ID NO: 17, comprising one or more amino acid reverse mutations selected from the group consisting of 38K and 46K;

(k) a framework region of the light chain variable region comprising the LCDR1, the LCDR2 and the LCDR3 having sequences set forth in SEQ ID NO: 30, SEQ ID NO: 31 and SEQ ID NO: 32, respectively, comprising one or more amino acid reverse mutations selected from the group consisting of 3V, 43P and 58V, and/or a framework region of the heavy chain variable region comprising the HCDR1, the HCDR2 and the HCDR3 having sequences set forth in SEQ ID NO: 27, SEQ ID NO: 28 and SEQ ID NO: 29, comprising one or more amino acid reverse mutations selected from the group consisting of 38K, 66K and 71V; and (I) a framework region of the light chain variable region comprising the LCDR1 having a sequence set forth in SEQ ID NO: 35, the LCDR2 having a sequence set forth in SEQ ID NO: 36 or SEQ ID NO: 64 and the LCDR3 having a sequence set forth in SEQ ID NO: 37, comprising one or more amino acid reverse mutations selected from the group consisting of 4V, 36Y, 43P, 47V, 49E, 70D and 871; and/or a framework region of the heavy chain variable region comprising the HCDR1 having a sequence set forth in SEQ ID NO: 33, the HCDR2 having a sequence set forth in SEQ ID NO: 16 or SEQ ID NO: 38 and the HCDR3 having a sequence set forth in SEQ ID NO: 34, comprising one or more amino acid reverse mutations selected from the group consisting of the group consisting of 2I, 38K and 46K;

wherein sites of the reverse mutations are numbered according to Kabat numbering scheme.

6. The antibody drug conjugate according to claim 1, wherein the anti-CEA antibody or the antigen-binding fragment thereof comprises a heavy chain constant region and a light chain constant region of the antibody; the heavy chain constant region is selected from the group consisting of human IgG1, IgG2, IgG3 and IgG4 constant regions and conventional variants thereof, and the light chain constant region is selected from the group consisting of human antibody K and A chain constant regions and conventional variants thereof.

7. The antibody drug conjugate according to claim 1, wherein the anti-CEA antibody or the antigen-binding fragment thereof comprises the heavy chain variable region of SEQ ID NO: 52 and the light chain variable region of SEQ ID NO: 53.

8. The antibody drug conjugate according to claim 1, wherein the anti-CEA antibody comprises the heavy chain constant region having a sequence set forth in SEQ ID NO: 77 and the light chain constant region having a sequence set forth in SEQ ID NO: 78 or SEQ ID NO: 79.

9. The antibody drug conjugate according to claim 1, wherein the anti-CEA antibody comprises:

(m) the heavy chain having a sequence set forth in SEQ ID NO: 80, and/or the light chain having a sequence set forth in SEQ ID NO: 81;

(n) the heavy chain having a sequence set forth in SEQ ID NO: 82, and/or the light chain having a sequence set forth in SEQ ID NO: 83;

(o) the heavy chain having a sequence set forth in SEQ ID NO: 84, and/or the light chain having a sequence set forth in SEQ ID NO: 85; or (p) the heavy chain having a sequence set forth in SEQ ID NO: 86, and/or the light chain having a sequence set forth in SEQ ID NO: 87.

10. A pharmaceutical composition comprising the antibody drug conjugate according to claim 1 and one or more pharmaceutically acceptable excipients, diluents or carriers.

11. The antibody drug conjugate according to claim 1, wherein the antibody drug conjugate is an antibody drug conjugate of general formula (Pc-L-Y-D):

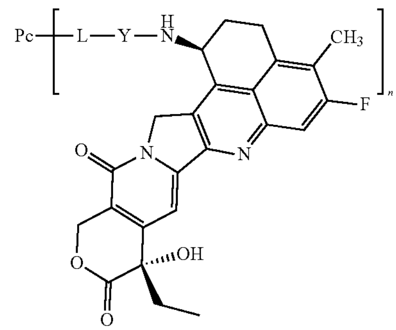

(Pc-L-Y-D)

wherein:

Y is selected from the group consisting of —O—$(CR^aR^b)_m$—$CR^1R^2$—C(O)—, —O—$CR^1R^2$—$(CR^aR^b)_m$—, —O—$CR^1R^2$—, —NH—$(CR^aR^b)_m$—$CR^1R^2$—C(O)— and —S—$(CR^aR^b)_m$—$CR^1R^2$—C(O)—;

$R^a$ and $R^b$ are identical or different and are each independently selected from the group consisting of hydrogen, deuterium, halogen, alkyl, haloalkyl, deuterated alkyl, alkoxy, hydroxy, amino, cyano, nitro, hydroxyalkyl, cycloalkyl and heterocyclyl; or, $R^a$ and $R^b$, together with carbon atoms connected thereto, form cycloalkyl and heterocyclyl;

$R^1$ is selected from the group consisting of halogen, haloalkyl, deuterated alkyl, cycloalkyl, cycloalkylalkyl, alkoxyalkyl, heterocyclyl, aryl and heteroaryl; $R^2$ is selected from the group consisting of hydrogen, halogen, haloalkyl, deuterated alkyl, cycloalkyl, cycloalkylalkyl, alkoxyalkyl, heterocyclyl, aryl and heteroaryl; or, $R^1$ and $R^2$, together with carbon atoms connected thereto, form cycloalkyl or heterocyclyl;

or, $R^a$ and $R^2$, together with carbon atoms connected thereto, form cycloalkyl or heterocyclyl;

m is an integer from 0 to 4;

n is a calculated mean, which is a decimal or an integer from 1 to 10;

L is a linker unit;

Pc is the anti-CEA antibody or the antigen-binding fragment thereof according to claim 1.

12. The antibody drug conjugate according to claim 11, wherein n is a calculated mean, which is an integer or a decimal from 2 to 8.

13. The antibody drug conjugate according to claim 11, wherein n is a calculated mean, which is an integer or a decimal from 4 to 6.

14. The antibody drug conjugate according to claim 11, wherein $L^3$ is a tetrapeptide residue of glycine-glycine-phenylalanine-glycine (GGFG, SEQ ID NO: 92).

15. The antibody drug conjugate according to claim 11, wherein-L- is:

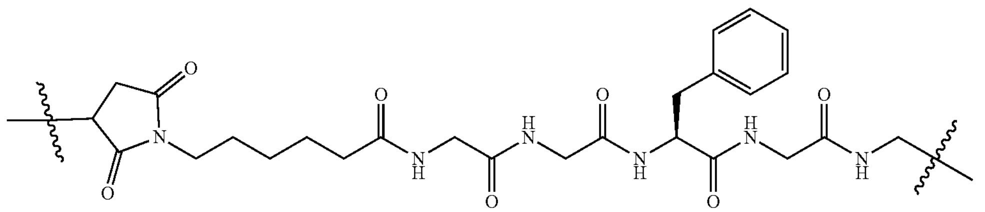

16. The antibody drug conjugate according to claim 11, wherein:

Y is —O—$(CR^aR^b)_m$—$CR^1R^2$—C(O)—;

$R^a$ and $R^b$ are identical or different and are each independently selected from the group consisting of hydrogen, deuterium, halogen and alkyl;

$R^1$ is haloalkyl or $C_{3-6}$ cycloalkyl;

$R^2$ is selected from the group consisting of hydrogen, haloalkyl and $C_{3-6}$ cycloalkyl;

or, $R^1$ and $R^2$, together with carbon atoms connected thereto, form $C_{3-6}$ cycloalkyl;

m is 0 or 1.

17. The antibody drug conjugate according to claim 16, wherein Y is selected from the group consisting of:

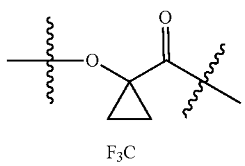
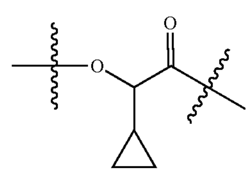
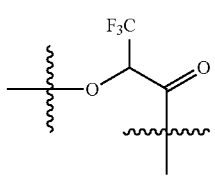
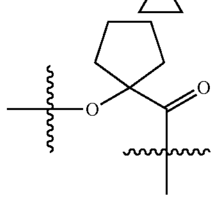
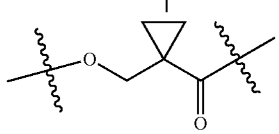
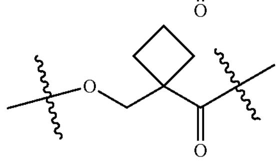
and
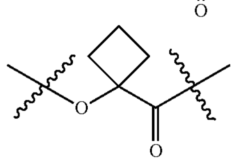
;

wherein the O terminus of Y is connected to the linker unit L.

18. The antibody drug conjugate according to claim 11, wherein the antibody drug conjugate is an antibody drug conjugate of general formula (Pc-L-D):

Pc-L-D

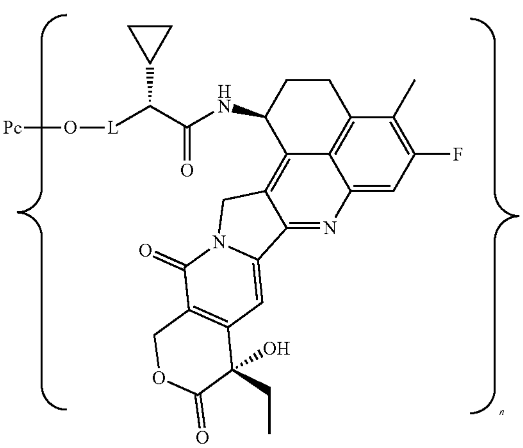

wherein:

L is a linker unit;

wherein Pc and n are as defined in claim 11.

19. The antibody drug conjugate according to claim 11, wherein the linker unit -L- is $-L^1-L^2-L^3-L^4-$, wherein $L^1$ is selected from the group consisting of -(succinimidyl-3-yl-N)—W—C(O)—, —$CH_2$—C(O)—$NR^3$—W—C(O)— and —C(O)—W—C(O)—, wherein W is selected from the group consisting of $C_{1-8}$ alkyl, $C_{1-8}$ alkyl-cycloalkyl and linear heteroalkyl of 1 to 8 atoms, and the heteroalkyl comprises 1 to 3 heteroatoms selected from the group consisting of N, O and S;

$L^2$ is selected from the group consisting of —$NR^4(CH_2CH_2O)p^1CH_2CH_2C(O)$—, —$NR^4(CH_2CH_2O)p^1CH_2C(O)$—, —$S(CH_2)p^1C(O)$— and a chemical bond, wherein $p^1$ is an integer from 1 to 20;

$L^3$ is a peptide residue consisting of 2 to 7 amino acids, wherein the amino acids are selected from the group consisting of amino acid residues formed from amino acids from phenylalanine, glycine, valine, lysine, citrulline, serine, glutamic acid and aspartic acid;

$L^4$ is selected from the group consisting of —$NR^5(CR^6R^7)_t$—, —$C(O)NR^5$—, —$C(O)NR^5(CH_2)_t$— and a chemical bond, wherein t is an integer from 1 to 6;

$R^3$, $R^4$ and $R^5$ are identical or different and are each independently selected from the group consisting of hydrogen, alkyl, haloalkyl, deuterated alkyl and hydroxyalkyl;

$R^6$ and $R^7$ are identical or different and are each independently selected from the group consisting of hydrogen, halogen, alkyl, haloalkyl, deuterated alkyl and hydroxyalkyl.

20. The antibody drug conjugate according to claim 11, wherein the linker unit -L- is $-L^1-L^2-L^3-L^4-$, wherein $L^1$ is

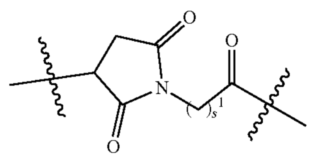

, and $s^1$ is an integer from 2 to 8;

$L^2$ is a chemical bond;

$L^3$ is a tetrapeptide residue;

$L^4$ is $—NR^5(CR^6R^7)_t—$, wherein $R^5$, $R^6$ and $R^7$ are identical or different and are each independently hydrogen or alkyl, and t is 1 or 2;

wherein the $L^1$ terminus is connected to Pc, and the $L^4$ terminus is connected to Y.

21. The antibody drug conjugate according to claim 11, wherein the antibody drug conjugate of general formula (Pc-L-Y-D) is an antibody drug conjugate of general formula (Pc-$L_b$-Y-D):

(Pc-$L$b-Y-D)

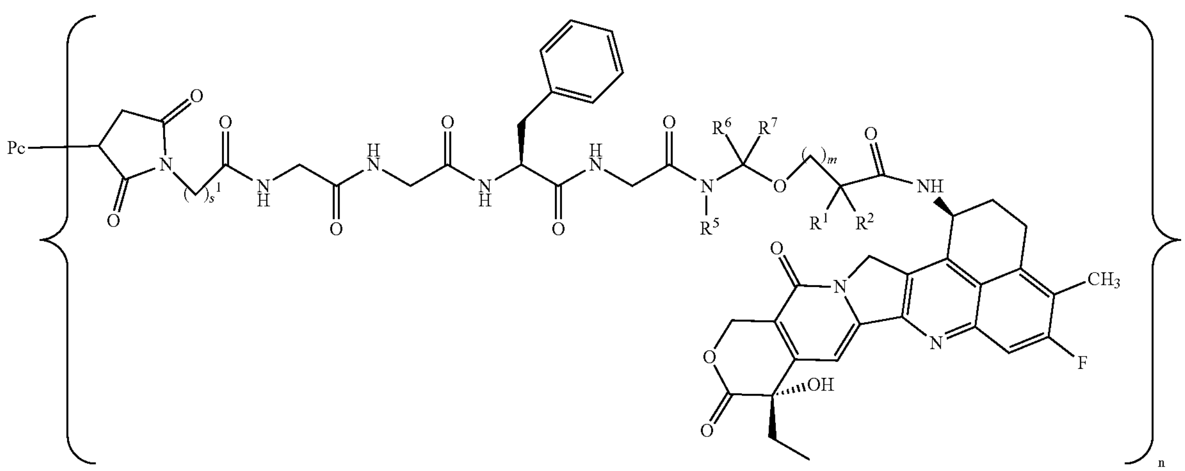

wherein:

$s^1$ is an integer from 2 to 8;

$R^1$ is selected from the group consisting of halogen, haloalkyl, deuterated alkyl, cycloalkyl, cycloalkylalkyl, alkoxyalkyl, heterocyclyl, aryl and heteroaryl; $R^2$ is selected from the group consisting of hydrogen, halogen, haloalkyl, deuterated alkyl, cycloalkyl, cycloalkylalkyl, alkoxyalkyl, heterocyclyl, aryl and heteroaryl; or, $R^1$ and $R^2$, together with carbon atoms connected thereto, form cycloalkyl or heterocyclyl;

or, $R^a$ and $R^2$, together with carbon atoms connected thereto, form cycloalkyl or heterocyclyl;

$R^5$ selected from the group consisting of hydrogen, alkyl, haloalkyl, deuterated alkyl and hydroxyalkyl;

$R^6$ and $R^7$ are identical or different and are each independently selected from the group consisting of hydrogen, halogen, alkyl, haloalkyl, deuterated alkyl and hydroxyalkyl;

m is an integer from 0 to 4;

n is a calculated mean, which is a decimal or an integer from 1 to 10.

22. The antibody drug conjugate according to claim 11, wherein the antibody drug conjugate is selected from the group consisting of:

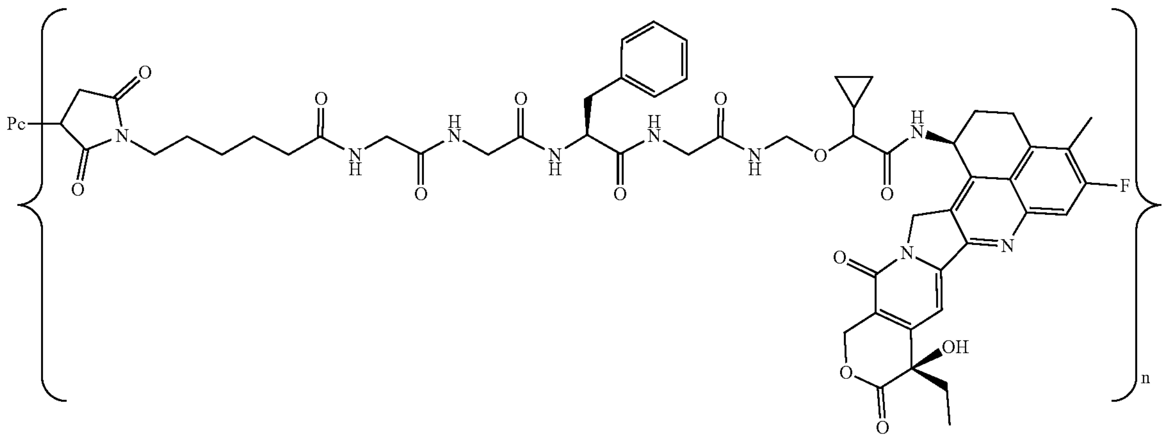
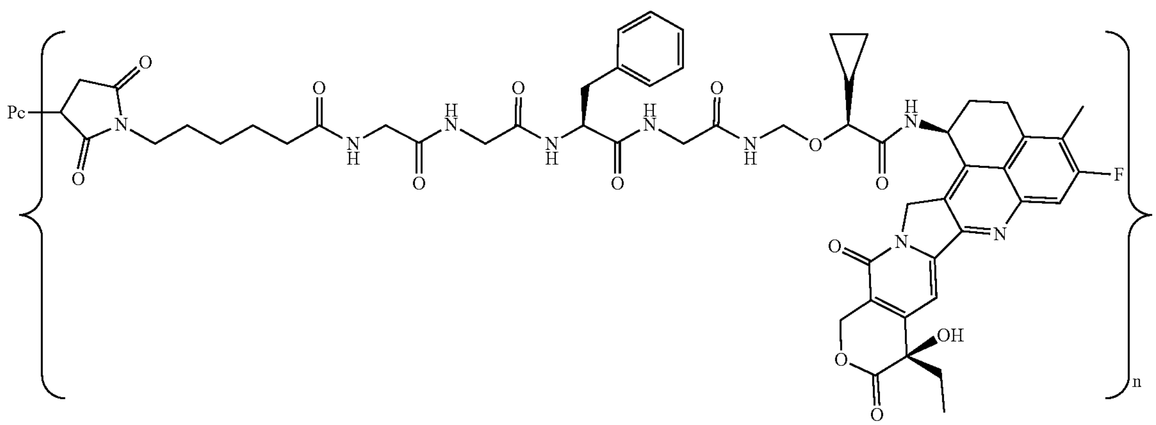
and
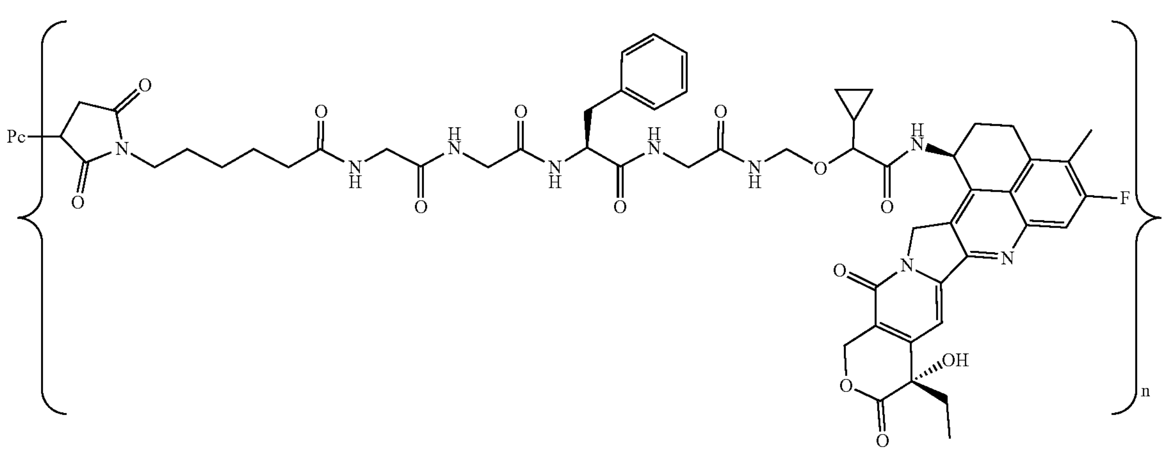
wherein Pc and n are as defined in claim 11.

23. The antibody drug conjugate according to claim 11, wherein the antibody drug conjugate is selected from the group consisting of:
Hu63-13-2-A
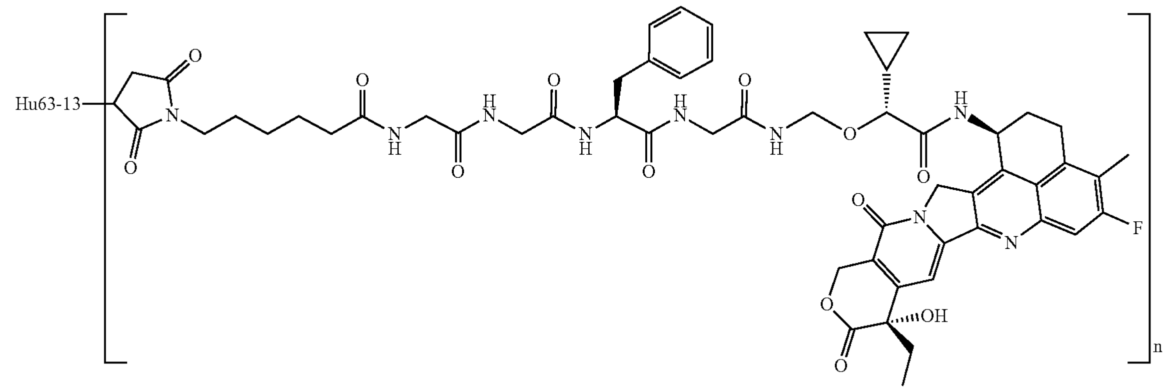
Hu47-14-2-A
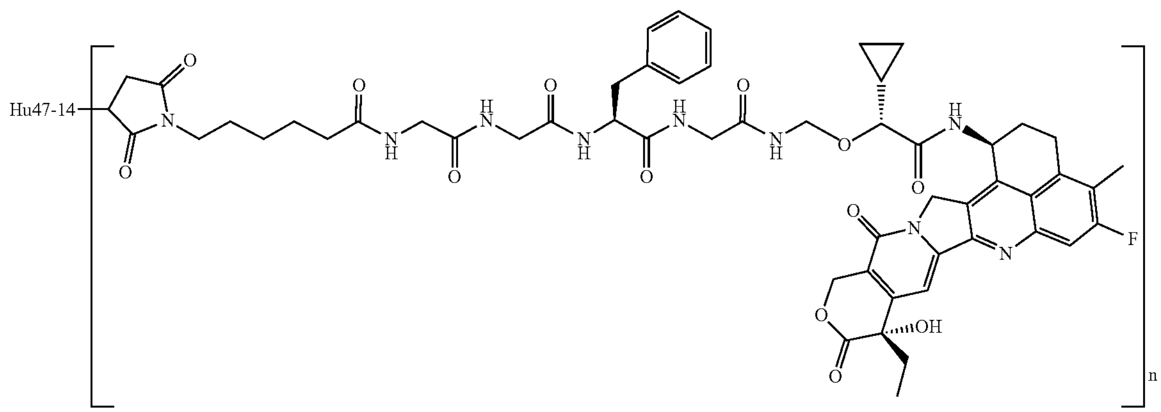
Hu67-14-2-A
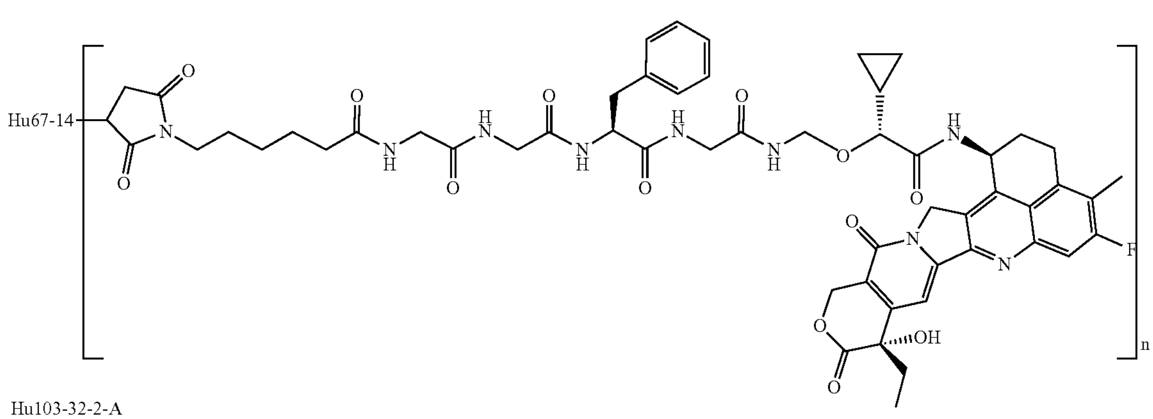
and
Hu103-32-2-A -continued

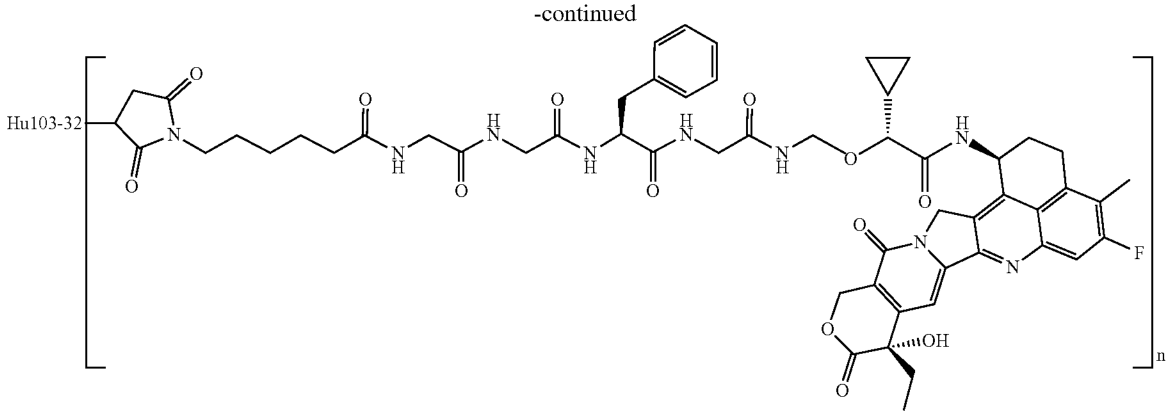

wherein n is as defined in claim 11;

and wherein Hu63-13 comprises the heavy chain having the sequence set forth in SEQ ID NO: 80, and the light chain having the sequence set forth in SEQ ID NO: 81;

Hu47-14 comprises the heavy chain having the sequence set forth in SEQ ID NO: 82, and the light chain having the sequence set forth in SEQ ID NO: 83;

Hu67-14 comprises the heavy chain having the sequence set forth in SEQ ID NO: 84, and the light chain having the sequence set forth in SEQ ID NO: 85;

Hu103-32 comprises the heavy chain having the sequence set forth in SEQ ID NO: 86, and the light chain having the sequence set forth in SEQ ID NO: 87.

24. A method of treating a CEA-mediated disease or condition in a subject in need thereof, the method comprising administering to the subject, the antibody drug conjugate according to claim 1.

25. The method according to claim 24, wherein the CEA-mediated disease or condition is a cancer with high CEA expression.

26. A method of treating a cancer in a subject in need thereof, the method comprising administering to the subject, an effective amount of the antibody drug conjugate according to claim 1.

27. The method according to claim 26, wherein the cancer is head and neck squamous cell carcinoma, head and neck cancer, brain cancer, neuroglioma, glioblastoma multiforme, neuroblastoma, central nervous system carcinoma, neuroendocrine tumor, throat cancer, nasopharyngeal cancer, esophageal cancer, thyroid cancer, malignant pleural mesothelioma, lung cancer, breast cancer, liver cancer, hepatobiliary cancer, pancreatic cancer, stomach cancer, gastrointestinal cancer, intestinal cancer, colon cancer, colorectal cancer, kidney cancer, clear cell renal cell carcinoma, ovarian cancer, endometrial cancer, cervical cancer, bladder cancer, prostate cancer, testicular cancer, skin cancer, melanoma, leukemia, lymphoma, bone cancer, chondrosarcoma, myeloma, multiple myeloma, myelodysplastic syndrome, Krukenberg tumor, myeloproliferative tumor, squamous cell carcinoma, Ewing's sarcoma, systemic light chain amyloidosis or Merkel cell carcinoma.

28. The method according to claim 27, wherein the lymphoma is selected from the group consisting of: Hodgkin's lymphoma, non-Hodgkin's lymphoma, diffuse large B-cell lymphoma, follicular lymphoma, primary mediastinal large B-cell lymphoma, mantle cell lymphoma, small lymphocytic lymphoma, large B-cell lymphoma rich in T-cells/histiocytes and lymphoplasmacytic lymphoma, the lung cancer is selected from the group consisting of non-small cell lung cancer and small cell lung cancer, and the leukemia is selected from the group consisting of: chronic myeloid leukemia, acute myeloid leukemia, lymphocytic leukemia, lymphoblastic leukemia, acute lymphoblastic leukemia, chronic lymphocytic leukemia and myeloid cell leukemia.

* * * * *

SEQUENCE LISTING

```
<160> NUMBER OF SEQ ID NOS: 92

<210> SEQ ID NO 1
<211> LENGTH: 657
<212> TYPE: PRT
<213> ORGANISM: Artificial Sequence
<220> FEATURE:
<223> OTHER INFORMATION: Synthetic Sequence_Protein sequence of human
      CEA-His (hCEA-His)

<400> SEQUENCE: 1

Lys Leu Thr Ile Glu Ser Thr Pro Phe Asn Val Ala Glu Gly Lys Glu
1               5                   10                  15

Val Leu Leu Leu Val His Asn Leu Pro Gln His Leu Phe Gly Tyr Ser
            20                  25                  30

Trp Tyr Lys Gly Glu Arg Val Asp Gly Asn Arg Gln Ile Ile Gly Tyr
        35                  40                  45

Val Ile Gly Thr Gln Gln Ala Thr Pro Gly Pro Ala Tyr Ser Gly Arg
    50                  55                  60

Glu Ile Ile Tyr Pro Asn Ala Ser Leu Leu Ile Gln Asn Ile Ile Gln
65                  70                  75                  80

Asn Asp Thr Gly Phe Tyr Thr Leu His Val Ile Lys Ser Asp Leu Val
                85                  90                  95

Asn Glu Glu Ala Thr Gly Gln Phe Arg Val Tyr Pro Glu Leu Pro Lys
            100                 105                 110

Pro Ser Ile Ser Ser Asn Asn Ser Lys Pro Val Glu Asp Lys Asp Ala
        115                 120                 125

Val Ala Phe Thr Cys Glu Pro Glu Thr Gln Asp Ala Thr Tyr Leu Trp
    130                 135                 140

Trp Val Asn Asn Gln Ser Leu Pro Val Ser Pro Arg Leu Gln Leu Ser
145                 150                 155                 160

Asn Gly Asn Arg Thr Leu Thr Leu Phe Asn Val Thr Arg Asn Asp Thr
                165                 170                 175

Ala Ser Tyr Lys Cys Glu Thr Gln Asn Pro Val Ser Ala Arg Arg Ser
            180                 185                 190

Asp Ser Val Ile Leu Asn Val Leu Tyr Gly Pro Asp Ala Pro Thr Ile
        195                 200                 205

Ser Pro Leu Asn Thr Ser Tyr Arg Ser Gly Glu Asn Leu Asn Leu Ser
    210                 215                 220

Cys His Ala Ala Ser Asn Pro Pro Ala Gln Tyr Ser Trp Phe Val Asn
225                 230                 235                 240
```

-continued

```
Gly Thr Phe Gln Gln Ser Thr Gln Glu Leu Phe Ile Pro Asn Ile Thr
                245                 250                 255

Val Asn Asn Ser Gly Ser Tyr Thr Cys Gln Ala His Asn Ser Asp Thr
            260                 265                 270

Gly Leu Asn Arg Thr Thr Val Thr Thr Ile Thr Val Tyr Ala Glu Pro
        275                 280                 285

Pro Lys Pro Phe Ile Thr Ser Asn Asn Ser Asn Pro Val Glu Asp Glu
    290                 295                 300

Asp Ala Val Ala Leu Thr Cys Glu Pro Glu Ile Gln Asn Thr Thr Tyr
305                 310                 315                 320

Leu Trp Trp Val Asn Asn Gln Ser Leu Pro Val Ser Pro Arg Leu Gln
                325                 330                 335

Leu Ser Asn Asp Asn Arg Thr Leu Thr Leu Leu Ser Val Thr Arg Asn
            340                 345                 350

Asp Val Gly Pro Tyr Glu Cys Gly Ile Gln Asn Glu Leu Ser Val Asp
        355                 360                 365

His Ser Asp Pro Val Ile Leu Asn Val Leu Tyr Gly Pro Asp Asp Pro
    370                 375                 380

Thr Ile Ser Pro Ser Tyr Thr Tyr Tyr Arg Pro Gly Val Asn Leu Ser
385                 390                 395                 400

Leu Ser Cys His Ala Ala Ser Asn Pro Pro Ala Gln Tyr Ser Trp Leu
                405                 410                 415

Ile Asp Gly Asn Ile Gln Gln His Thr Gln Glu Leu Phe Ile Ser Asn
            420                 425                 430

Ile Thr Glu Lys Asn Ser Gly Leu Tyr Thr Cys Gln Ala Asn Asn Ser
        435                 440                 445

Ala Ser Gly His Ser Arg Thr Thr Val Lys Thr Ile Thr Val Ser Ala
    450                 455                 460

Glu Leu Pro Lys Pro Ser Ile Ser Ser Asn Asn Ser Lys Pro Val Glu
465                 470                 475                 480

Asp Lys Asp Ala Val Ala Phe Thr Cys Glu Pro Glu Ala Gln Asn Thr
                485                 490                 495

Thr Tyr Leu Trp Trp Val Asn Gly Gln Ser Leu Pro Val Ser Pro Arg
            500                 505                 510

Leu Gln Leu Ser Asn Gly Asn Arg Thr Leu Thr Leu Phe Asn Val Thr
        515                 520                 525

Arg Asn Asp Ala Arg Ala Tyr Val Cys Gly Ile Gln Asn Ser Val Ser
    530                 535                 540

Ala Asn Arg Ser Asp Pro Val Thr Leu Asp Val Leu Tyr Gly Pro Asp
545                 550                 555                 560

Thr Pro Ile Ile Ser Pro Pro Asp Ser Ser Tyr Leu Ser Gly Ala Asn
                565                 570                 575

Leu Asn Leu Ser Cys His Ser Ala Ser Asn Pro Ser Pro Gln Tyr Ser
            580                 585                 590

Trp Arg Ile Asn Gly Ile Pro Gln Gln His Thr Gln Val Leu Phe Ile
        595                 600                 605

Ala Lys Ile Thr Pro Asn Asn Asn Gly Thr Tyr Ala Cys Phe Val Ser
    610                 615                 620

Asn Leu Ala Thr Gly Arg Asn Asn Ser Ile Val Lys Ser Ile Thr Val
625                 630                 635                 640

Ser Ala Ser Gly Thr Ser Pro Gly Leu Ser Ala His His His His His
                645                 650                 655

His
```

-continued

<210> SEQ ID NO 2
<211> LENGTH: 883
<212> TYPE: PRT
<213> ORGANISM: Artificial Sequence
<220> FEATURE:
<223> OTHER INFORMATION: Synthetic Sequence_Protein sequence of human CEA-Fc (hCEA-Fc)

<400> SEQUENCE: 2

```
Lys Leu Thr Ile Glu Ser Thr Pro Phe Asn Val Ala Glu Gly Lys Glu
1               5                   10                  15

Val Leu Leu Leu Val His Asn Leu Pro Gln His Leu Phe Gly Tyr Ser
            20                  25                  30

Trp Tyr Lys Gly Glu Arg Val Asp Gly Asn Arg Gln Ile Ile Gly Tyr
        35                  40                  45

Val Ile Gly Thr Gln Gln Ala Thr Pro Gly Pro Ala Tyr Ser Gly Arg
    50                  55                  60

Glu Ile Ile Tyr Pro Asn Ala Ser Leu Leu Ile Gln Asn Ile Ile Gln
65                  70                  75                  80

Asn Asp Thr Gly Phe Tyr Thr Leu His Val Ile Lys Ser Asp Leu Val
                85                  90                  95

Asn Glu Glu Ala Thr Gly Gln Phe Arg Val Tyr Pro Glu Leu Pro Lys
            100                 105                 110

Pro Ser Ile Ser Ser Asn Asn Ser Lys Pro Val Glu Asp Lys Asp Ala
        115                 120                 125

Val Ala Phe Thr Cys Glu Pro Glu Thr Gln Asp Ala Thr Tyr Leu Trp
    130                 135                 140

Trp Val Asn Asn Gln Ser Leu Pro Val Ser Pro Arg Leu Gln Leu Ser
145                 150                 155                 160

Asn Gly Asn Arg Thr Leu Thr Leu Phe Asn Val Thr Arg Asn Asp Thr
                165                 170                 175

Ala Ser Tyr Lys Cys Glu Thr Gln Asn Pro Val Ser Ala Arg Arg Ser
            180                 185                 190

Asp Ser Val Ile Leu Asn Val Leu Tyr Gly Pro Asp Ala Pro Thr Ile
        195                 200                 205

Ser Pro Leu Asn Thr Ser Tyr Arg Ser Gly Glu Asn Leu Asn Leu Ser
    210                 215                 220

Cys His Ala Ala Ser Asn Pro Pro Ala Gln Tyr Ser Trp Phe Val Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Thr Cys Gln Ala His Asn Ser Asp Thr
            260                 265                 270

Gly Leu Asn Arg Thr Thr Val Thr Thr Ile Thr Val Tyr Ala Glu Pro
        275                 280                 285

Pro Lys Pro Phe Ile Thr Ser Asn Asn Ser Asn Pro Val Glu Asp Glu
    290                 295                 300

Asp Ala Val Ala Leu Thr Cys Glu Pro Glu Ile Gln Asn Thr Thr Tyr
305                 310                 315                 320

Leu Trp Trp Val Asn Asn Gln Ser Leu Pro Val Ser Pro Arg Leu Gln
                325                 330                 335

Leu Ser Asn Asp Asn Arg Thr Leu Thr Leu Leu Ser Val Thr Arg Asn
            340                 345                 350

Asp Val Gly Pro Tyr Glu Cys Gly Ile Gln Asn Glu Leu Ser Val Asp
```

-continued

```
        355                 360                 365

His Ser Asp Pro Val Ile Leu Asn Val Leu Tyr Gly Pro Asp Asp Pro
    370                 375                 380

Thr Ile Ser Pro Ser Tyr Thr Tyr Tyr Arg Pro Gly Val Asn Leu Ser
385                 390                 395                 400

Leu Ser Cys His Ala Ala Ser Asn Pro Pro Ala Gln Tyr Ser Trp Leu
                405                 410                 415

Ile Asp Gly Asn Ile Gln Gln His Thr Gln Glu Leu Phe Ile Ser Asn
            420                 425                 430

Ile Thr Glu Lys Asn Ser Gly Leu Tyr Thr Cys Gln Ala Asn Asn Ser
        435                 440                 445

Ala Ser Gly His Ser Arg Thr Thr Val Lys Thr Ile Thr Val Ser Ala
    450                 455                 460

Glu Leu Pro Lys Pro Ser Ile Ser Ser Asn Asn Ser Lys Pro Val Glu
465                 470                 475                 480

Asp Lys Asp Ala Val Ala Phe Thr Cys Glu Pro Glu Ala Gln Asn Thr
                485                 490                 495

Thr Tyr Leu Trp Trp Val Asn Gly Gln Ser Leu Pro Val Ser Pro Arg
            500                 505                 510

Leu Gln Leu Ser Asn Gly Asn Arg Thr Leu Thr Leu Phe Asn Val Thr
        515                 520                 525

Arg Asn Asp Ala Arg Ala Tyr Val Cys Gly Ile Gln Asn Ser Val Ser
    530                 535                 540

Ala Asn Arg Ser Asp Pro Val Thr Leu Asp Val Leu Tyr Gly Pro Asp
545                 550                 555                 560

Thr Pro Ile Ile Ser Pro Pro Asp Ser Ser Tyr Leu Ser Gly Ala Asn
                565                 570                 575

Leu Asn Leu Ser Cys His Ser Ala Ser Asn Pro Ser Pro Gln Tyr Ser
            580                 585                 590

Trp Arg Ile Asn Gly Ile Pro Gln Gln His Thr Gln Val Leu Phe Ile
        595                 600                 605

Ala Lys Ile Thr Pro Asn Asn Asn Gly Thr Tyr Ala Cys Phe Val Ser
    610                 615                 620

Asn Leu Ala Thr Gly Arg Asn Asn Ser Ile Val Lys Ser Ile Thr Val
625                 630                 635                 640

Ser Ala Ser Gly Thr Ser Pro Gly Leu Ser Ala Glu Pro Lys Ser Ser
                645                 650                 655

Asp Lys Thr His Thr Cys Pro Pro Cys Pro Ala Pro Glu Leu Leu Gly
            660                 665                 670

Gly Pro Ser Val Phe Leu Phe Pro Pro Lys Pro Lys Asp Thr Leu Met
        675                 680                 685

Ile Ser Arg Thr Pro Glu Val Thr Cys Val Val Val Asp Val Ser His
    690                 695                 700

Glu Asp Pro Glu Val Lys Phe Asn Trp Tyr Val Asp Gly Val Glu Val
705                 710                 715                 720

His Asn Ala Lys Thr Lys Pro Arg Glu Glu Gln Tyr Asn Ser Thr Tyr
                725                 730                 735

Arg Val Val Ser Val Leu Thr Val Leu His Gln Asp Trp Leu Asn Gly
            740                 745                 750

Lys Glu Tyr Lys Cys Lys Val Ser Asn Lys Ala Leu Pro Ala Pro Ile
        755                 760                 765

Glu Lys Thr Ile Ser Lys Ala Lys Gly Gln Pro Arg Glu Pro Gln Val
    770                 775                 780
```

```
Tyr Thr Leu Pro Pro Ser Arg Asp Glu Leu Thr Lys Asn Gln Val Ser
785                 790                 795                 800

Leu Thr Cys Leu Val Lys Gly Phe Tyr Pro Ser Asp Ile Ala Val Glu
                805                 810                 815

Trp Glu Ser Asn Gly Gln Pro Glu Asn Asn Tyr Lys Thr Thr Pro Pro
            820                 825                 830

Val Leu Asp Ser Asp Gly Ser Phe Phe Leu Tyr Ser Lys Leu Thr Val
        835                 840                 845

Asp Lys Ser Arg Trp Gln Gln Gly Asn Val Phe Ser Cys Ser Val Met
    850                 855                 860

His Glu Ala Leu His Asn His Tyr Thr Gln Lys Ser Leu Ser Leu Ser
865                 870                 875                 880

Pro Gly Lys


<210> SEQ ID NO 3
<211> LENGTH: 660
<212> TYPE: PRT
<213> ORGANISM: Artificial Sequence
<220> FEATURE:
<223> OTHER INFORMATION: Synthetic Sequence_Protein sequence of
      cynomolgus monkey CEA-His (cynoCEA-His)

<400> SEQUENCE: 3

Gln Leu Thr Ile Glu Ser Arg Pro Phe Asn Val Ala Glu Gly Lys Glu
1               5                   10                  15

Val Leu Leu Leu Ala His Asn Val Ser Gln Asn Leu Phe Gly Tyr Ile
            20                  25                  30

Trp Tyr Lys Gly Glu Arg Val Asp Ala Ser Arg Arg Ile Gly Ser Cys
        35                  40                  45

Val Ile Arg Thr Gln Gln Ile Thr Pro Gly Pro Ala His Ser Gly Arg
    50                  55                  60

Glu Thr Ile Asp Phe Asn Ala Ser Leu Leu Ile Gln Asn Val Thr Gln
65                  70                  75                  80

Ser Asp Thr Gly Ser Tyr Thr Ile Gln Val Ile Lys Glu Asp Leu Val
                85                  90                  95

Asn Glu Glu Ala Thr Gly Gln Phe Arg Val Tyr Pro Glu Leu Pro Lys
            100                 105                 110

Pro Tyr Ile Thr Ser Asn Asn Ser Asn Pro Ile Glu Asp Lys Asp Ala
        115                 120                 125

Val Ala Leu Thr Cys Glu Pro Glu Thr Gln Asp Thr Thr Tyr Leu Trp
    130                 135                 140

Trp Val Asn Asn Gln Ser Leu Pro Val Ser Pro Arg Leu Glu Leu Ser
145                 150                 155                 160

Ser Asp Asn Arg Thr Leu Thr Val Phe Asn Ile Pro Arg Asn Asp Thr
                165                 170                 175

Thr Ser Tyr Lys Cys Glu Thr Gln Asn Pro Val Ser Val Arg Arg Ser
            180                 185                 190

Asp Pro Val Thr Leu Asn Val Leu Tyr Gly Pro Asp Ala Pro Thr Ile
        195                 200                 205

Ser Pro Leu Asn Thr Pro Tyr Arg Ala Gly Glu Tyr Leu Asn Leu Thr
    210                 215                 220

Cys His Ala Ala Ser Asn Pro Thr Ala Gln Tyr Phe Trp Phe Val Asn
225                 230                 235                 240

Gly Thr Phe Gln Gln Ser Thr Gln Glu Leu Phe Ile Pro Asn Ile Thr
                245                 250                 255
```

-continued

```
Val Asn Asn Ser Gly Ser Tyr Met Cys Gln Ala His Asn Ser Ala Thr
            260                 265                 270

Gly Leu Asn Arg Thr Thr Val Thr Ala Ile Thr Val Tyr Ala Glu Leu
        275                 280                 285

Pro Lys Pro Tyr Ile Thr Ser Asn Asn Ser Asn Pro Ile Glu Asp Lys
    290                 295                 300

Asp Ala Val Thr Leu Thr Cys Glu Pro Glu Thr Gln Asp Thr Thr Tyr
305                 310                 315                 320

Leu Trp Trp Val Asn Asn Gln Arg Leu Ser Val Ser Ser Arg Leu Glu
                325                 330                 335

Leu Ser Asn Asp Asn Arg Thr Leu Thr Val Phe Asn Ile Pro Arg Asn
            340                 345                 350

Asp Thr Thr Phe Tyr Glu Cys Glu Thr Gln Asn Pro Val Ser Val Arg
        355                 360                 365

Arg Ser Asp Pro Val Thr Leu Asn Val Leu Tyr Gly Pro Asp Ala Pro
    370                 375                 380

Thr Ile Ser Pro Leu Asn Thr Pro Tyr Arg Ala Gly Glu Asn Leu Asn
385                 390                 395                 400

Leu Ser Cys His Ala Ala Ser Asn Pro Ala Ala Gln Tyr Phe Trp Phe
                405                 410                 415

Val Asn Gly Thr Phe Gln Gln Ser Thr Gln Glu Leu Phe Ile Pro Asn
            420                 425                 430

Ile Thr Val Asn Asn Ser Gly Ser Tyr Met Cys Gln Ala His Asn Ser
        435                 440                 445

Ala Thr Gly Leu Asn Arg Thr Thr Val Thr Ala Ile Thr Val Tyr Val
    450                 455                 460

Glu Leu Pro Lys Pro Tyr Ile Ser Ser Asn Asn Ser Asn Pro Ile Glu
465                 470                 475                 480

Asp Lys Asp Ala Val Thr Leu Thr Cys Glu Pro Val Ala Glu Asn Thr
                485                 490                 495

Thr Tyr Leu Trp Trp Val Asn Asn Gln Ser Leu Ser Val Ser Pro Arg
            500                 505                 510

Leu Gln Leu Ser Asn Gly Asn Arg Ile Leu Thr Leu Leu Ser Val Thr
        515                 520                 525

Arg Asn Asp Thr Gly Pro Tyr Glu Cys Gly Ile Gln Asn Ser Glu Ser
    530                 535                 540

Ala Lys Arg Ser Asp Pro Val Thr Leu Asn Val Thr Tyr Gly Pro Asp
545                 550                 555                 560

Thr Pro Ile Ile Ser Pro Pro Asp Leu Ser Tyr Arg Ser Gly Ala Asn
                565                 570                 575

Leu Asn Leu Ser Cys His Ser Asp Ser Asn Pro Ser Pro Gln Tyr Ser
            580                 585                 590

Trp Leu Ile Asn Gly Thr Leu Arg Gln His Thr Gln Val Leu Phe Ile
        595                 600                 605

Ser Lys Ile Thr Ser Asn Asn Asn Gly Ala Tyr Ala Cys Phe Val Ser
    610                 615                 620

Asn Leu Ala Thr Gly Arg Asn Asn Ser Ile Val Lys Asn Ile Ser Val
625                 630                 635                 640

Ser Ser Gly Asp Ser Ala Pro Gly Ser Ser Gly Leu Ser Ala His His
                645                 650                 655

His His His His
            660
```

-continued

<210> SEQ ID NO 4
<211> LENGTH: 702
<212> TYPE: PRT
<213> ORGANISM: Artificial Sequence
<220> FEATURE:
<223> OTHER INFORMATION: Synthetic Sequence_Protein sequence of human
CEA expressed on CHO cell surface (hCEA-CHO)

<400> SEQUENCE: 4

```
Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365
```

```
Leu Gln Leu Ser Asn Asp Asn Arg Thr Leu Thr Leu Leu Ser Val Thr
    370                 375                 380

Arg Asn Asp Val Gly Pro Tyr Glu Cys Gly Ile Gln Asn Glu Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
            420                 425                 430

Leu Ser Leu Ser Cys His Ala Ala Ser Asn Pro Pro Ala Gln Tyr Ser
        435                 440                 445

Trp Leu Ile Asp Gly Asn Ile Gln Gln His Thr Gln Glu Leu Phe Ile
    450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
        515                 520                 525

Asn Thr Thr Tyr Leu Trp Trp Val Asn Gly Gln Ser Leu Pro Val Ser
    530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
        595                 600                 605

Ala Asn Leu Asn Leu Ser Cys His Ser Ala Ser Asn Pro Ser Pro Gln
    610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
            660                 665                 670

Thr Val Ser Ala Ser Gly Thr Ser Pro Gly Leu Ser Ala Gly Ala Thr
        675                 680                 685

Val Gly Ile Met Ile Gly Val Leu Val Gly Val Ala Leu Ile
    690                 695                 700
```

<210> SEQ ID NO 5
<211> LENGTH: 690
<212> TYPE: PRT
<213> ORGANISM: Artificial Sequence
<220> FEATURE:
<223> OTHER INFORMATION: Synthetic Sequence_Protein sequence of cynomolgus monkey CEA expressed on CHO cell surface (cynoCEA-CHO)

<400> SEQUENCE: 5

```
Met Glu Phe Gly Leu Ser Trp Leu Phe Leu Val Ala Ile Leu Lys Gly
1               5                   10                  15

Val Gln Cys Gln Leu Thr Ile Glu Ser Arg Pro Phe Asn Val Ala Glu
```

-continued

```
            20                  25                  30

Gly Lys Glu Val Leu Leu Leu Ala His Asn Val Ser Gln Asn Leu Phe
        35                  40                  45

Gly Tyr Ile Trp Tyr Lys Gly Glu Arg Val Asp Ala Ser Arg Arg Ile
    50                  55                  60

Gly Ser Cys Val Ile Arg Thr Gln Gln Ile Thr Pro Gly Pro Ala His
65                  70                  75                  80

Ser Gly Arg Glu Thr Ile Asp Phe Asn Ala Ser Leu Leu Ile Gln Asn
                85                  90                  95

Val Thr Gln Ser Asp Thr Gly Ser Tyr Thr Ile Gln Val Ile Lys Glu
            100                 105                 110

Asp Leu Val Asn Glu Glu Ala Thr Gly Gln Phe Arg Val Tyr Pro Glu
        115                 120                 125

Leu Pro Lys Pro Tyr Ile Thr Ser Asn Asn Ser Asn Pro Ile Glu Asp
    130                 135                 140

Lys Asp Ala Val Ala Leu Thr Cys Glu Pro Glu Thr Gln Asp Thr Thr
145                 150                 155                 160

Tyr Leu Trp Trp Val Asn Asn Gln Ser Leu Pro Val Ser Pro Arg Leu
                165                 170                 175

Glu Leu Ser Ser Asp Asn Arg Thr Leu Thr Val Phe Asn Ile Pro Arg
            180                 185                 190

Asn Asp Thr Thr Ser Tyr Lys Cys Glu Thr Gln Asn Pro Val Ser Val
        195                 200                 205

Arg Arg Ser Asp Pro Val Thr Leu Asn Val Leu Tyr Gly Pro Asp Ala
    210                 215                 220

Pro Thr Ile Ser Pro Leu Asn Thr Pro Tyr Arg Ala Gly Glu Tyr Leu
225                 230                 235                 240

Asn Leu Thr Cys His Ala Ala Ser Asn Pro Thr Ala Gln Tyr Phe Trp
                245                 250                 255

Phe Val Asn Gly Thr Phe Gln Gln Ser Thr Gln Glu Leu Phe Ile Pro
            260                 265                 270

Asn Ile Thr Val Asn Asn Ser Gly Ser Tyr Met Cys Gln Ala His Asn
        275                 280                 285

Ser Ala Thr Gly Leu Asn Arg Thr Thr Val Thr Ala Ile Thr Val Tyr
    290                 295                 300

Ala Glu Leu Pro Lys Pro Tyr Ile Thr Ser Asn Asn Ser Asn Pro Ile
305                 310                 315                 320

Glu Asp Lys Asp Ala Val Thr Leu Thr Cys Glu Pro Glu Thr Gln Asp
                325                 330                 335

Thr Thr Tyr Leu Trp Trp Val Asn Asn Gln Arg Leu Ser Val Ser Ser
            340                 345                 350

Arg Leu Glu Leu Ser Asn Asp Asn Arg Thr Leu Thr Val Phe Asn Ile
        355                 360                 365

Pro Arg Asn Asp Thr Thr Phe Tyr Glu Cys Glu Thr Gln Asn Pro Val
    370                 375                 380

Ser Val Arg Arg Ser Asp Pro Val Thr Leu Asn Val Leu Tyr Gly Pro
385                 390                 395                 400

Asp Ala Pro Thr Ile Ser Pro Leu Asn Thr Pro Tyr Arg Ala Gly Glu
                405                 410                 415

Asn Leu Asn Leu Ser Cys His Ala Ala Ser Asn Pro Ala Ala Gln Tyr
            420                 425                 430

Phe Trp Phe Val Asn Gly Thr Phe Gln Gln Ser Thr Gln Glu Leu Phe
        435                 440                 445
```

```
Ile Pro Asn Ile Thr Val Asn Asn Ser Gly Ser Tyr Met Cys Gln Ala
    450                 455                 460

His Asn Ser Ala Thr Gly Leu Asn Arg Thr Thr Val Thr Ala Ile Thr
465                 470                 475                 480

Val Tyr Val Glu Leu Pro Lys Pro Tyr Ile Ser Ser Asn Asn Ser Asn
                485                 490                 495

Pro Ile Glu Asp Lys Asp Ala Val Thr Leu Thr Cys Glu Pro Val Ala
            500                 505                 510

Glu Asn Thr Thr Tyr Leu Trp Trp Val Asn Asn Gln Ser Leu Ser Val
        515                 520                 525

Ser Pro Arg Leu Gln Leu Ser Asn Gly Asn Arg Ile Leu Thr Leu Leu
    530                 535                 540

Ser Val Thr Arg Asn Asp Thr Gly Pro Tyr Glu Cys Gly Ile Gln Asn
545                 550                 555                 560

Ser Glu Ser Ala Lys Arg Ser Asp Pro Val Thr Leu Asn Val Thr Tyr
                565                 570                 575

Gly Pro Asp Thr Pro Ile Ile Ser Pro Pro Asp Leu Ser Tyr Arg Ser
            580                 585                 590

Gly Ala Asn Leu Asn Leu Ser Cys His Ser Asp Ser Asn Pro Ser Pro
        595                 600                 605

Gln Tyr Ser Trp Leu Ile Asn Gly Thr Leu Arg Gln His Thr Gln Val
    610                 615                 620

Leu Phe Ile Ser Lys Ile Thr Ser Asn Asn Asn Gly Ala Tyr Ala Cys
625                 630                 635                 640

Phe Val Ser Asn Leu Ala Thr Gly Arg Asn Asn Ser Ile Val Lys Asn
                645                 650                 655

Ile Ser Val Ser Ser Gly Asp Ser Ala Pro Gly Ser Ser Gly Leu Ser
            660                 665                 670

Ala Arg Ala Thr Val Gly Ile Ile Ile Gly Met Leu Val Gly Val Ala
        675                 680                 685

Leu Met
    690
```

<210> SEQ ID NO 6
<211> LENGTH: 526
<212> TYPE: PRT
<213> ORGANISM: Artificial Sequence
<220> FEATURE:
<223> OTHER INFORMATION: Synthetic Sequence_Protein sequence of human CEACAM1 expressed on CHO cell surface (CEACAM1-CHO)

<400> SEQUENCE: 6

```
Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
            20                  25                  30

Thr Ala Gln Leu Thr Thr Glu Ser Met Pro Phe Asn Val Ala Glu Gly
        35                  40                  45

Lys Glu Val Leu Leu Leu Val His Asn Leu Pro Gln Gln Leu Phe Gly
    50                  55                  60

Tyr Ser Trp Tyr Lys Gly Glu Arg Val Asp Gly Asn Arg Gln Ile Val
65                  70                  75                  80

Gly Tyr Ala Ile Gly Thr Gln Gln Ala Thr Pro Gly Pro Ala Asn Ser
                85                  90                  95

Gly Arg Glu Thr Ile Tyr Pro Asn Ala Ser Leu Leu Ile Gln Asn Val
```

-continued

```
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
            180                 185                 190

Leu Ser Asn Gly Asn Arg Thr Leu Thr Leu Leu Ser Val Thr Arg Asn
        195                 200                 205

Asp Thr Gly Pro Tyr Glu Cys Glu Ile Gln Asn Pro Val Ser Ala Asn
    210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Thr Cys His Ala Asn Asn Ser
    290                 295                 300

Val Thr Gly Cys Asn Arg Thr Thr Val Lys Thr Ile Ile Val Thr Glu
305                 310                 315                 320

Leu Ser Pro Val Val Ala Lys Pro Gln Ile Lys Ala Ser Lys Thr Thr
                325                 330                 335

Val Thr Gly Asp Lys Asp Ser Val Asn Leu Thr Cys Ser Thr Asn Asp
            340                 345                 350

Thr Gly Ile Ser Ile Arg Trp Phe Phe Lys Asn Gln Ser Leu Pro Ser
        355                 360                 365

Ser Glu Arg Met Lys Leu Ser Gln Gly Asn Thr Thr Leu Ser Ile Asn
    370                 375                 380

Pro Val Lys Arg Glu Asp Ala Gly Thr Tyr Trp Cys Glu Val Phe Asn
385                 390                 395                 400

Pro Ile Ser Lys Asn Gln Ser Asp Pro Ile Met Leu Asn Val Asn Tyr
                405                 410                 415

Asn Ala Leu Pro Gln Glu Asn Gly Leu Ser Pro Gly Ala Ile Ala Gly
            420                 425                 430

Ile Val Ile Gly Val Val Ala Leu Val Ala Leu Ile Ala Val Ala Leu
        435                 440                 445

Ala Cys Phe Leu His Phe Gly Lys Thr Gly Arg Ala Ser Asp Gln Arg
    450                 455                 460

Asp Leu Thr Glu His Lys Pro Ser Val Ser Asn His Thr Gln Asp His
465                 470                 475                 480

Ser Asn Asp Pro Pro Asn Lys Met Asn Glu Val Thr Tyr Ser Thr Leu
                485                 490                 495

Asn Phe Glu Ala Gln Gln Pro Thr Gln Pro Thr Ser Ala Ser Pro Ser
            500                 505                 510

Leu Thr Ala Thr Glu Ile Ile Tyr Ser Glu Val Lys Lys Gln
        515                 520                 525
```

<210> SEQ ID NO 7
<211> LENGTH: 120
<212> TYPE: PRT
<213> ORGANISM: Mus musculus_Heavy chain variable region sequence of mAb47

<400> SEQUENCE: 7

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

Gly Met Ser Trp Val Lys Gln Ala Pro Gly Lys Gly Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Arg Gly Asn Tyr Gly Arg Trp Asp Phe Asp Val Trp Gly Thr
            100                 105                 110

Gly Thr Thr Val Thr Val Ser Ser
        115                 120

<210> SEQ ID NO 8
<211> LENGTH: 108
<212> TYPE: PRT
<213> ORGANISM: Mus musculus_Light chain variable region sequence of mAb47

<400> SEQUENCE: 8

Glu Ile Val Leu Thr Gln Ser Pro Ala Leu Met Ala Ala Ser Pro Gly
1               5                   10                  15

Glu Lys Val Thr Ile Thr Cys Ser Val Ser Ser Thr Ile Ser Ser Ser
            20                  25                  30

Asn Leu His Trp Tyr Gln Gln Lys Ser Glu Thr Ser Pro Lys Pro Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ile Tyr Pro
                85                  90                  95

Leu Thr Phe Gly Ala Gly Thr Lys Leu Glu Leu Lys
            100                 105

<210> SEQ ID NO 9
<211> LENGTH: 119
<212> TYPE: PRT
<213> ORGANISM: Mus musculus_Heavy chain variable region sequence of mAb63

<400> SEQUENCE: 9

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Phe
            20                  25                  30

-continued

```
Tyr Met Asn Trp Val Arg Gln Ser His Gly Lys Ser Leu Glu Trp Ile
        35                  40                  45

Gly Asp Ile Phe Pro Lys Asn Gly Asn Thr Asp Tyr Asn Arg Lys Phe
    50                  55                  60

Lys Asp Lys Ala Thr Leu Thr Val Asp Lys Ser Ser Asn Thr Val Tyr
65                  70                  75                  80

Met Glu Phe Arg Ser Leu Thr Leu Glu Asp Ser Ala Ile Tyr Phe Cys
                85                  90                  95

Ala Arg Ser Gly Tyr Gly Asn Tyr Val Phe Asp Tyr Trp Gly Gln Gly
            100                 105                 110

Thr Ile Phe Thr Val Ser Ser
        115


<210> SEQ ID NO 10
<211> LENGTH: 107
<212> TYPE: PRT
<213> ORGANISM: Mus musculus_Light chain variable region sequence of
      mAb63

<400> SEQUENCE: 10

Asp Val Gln Met Thr Gln Thr Pro Ser Ala Leu Ser Ala Ser Leu Gly
1               5                   10                  15

Asp Arg Val Thr Ile Ser Cys Arg Thr Ser Gln Asp Ile Asn Ile Tyr
            20                  25                  30

Leu Asn Trp Tyr Gln Gln Lys Pro Asp Gly Thr Val Lys Leu Leu Ile
        35                  40                  45

Tyr Tyr Arg Ser Gly Leu Leu Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Phe Cys Gln Gln Gly Asn Thr Leu Pro Pro
                85                  90                  95

Thr Phe Gly Gly Gly Thr Lys Leu Glu Ile Lys
            100                 105


<210> SEQ ID NO 11
<211> LENGTH: 117
<212> TYPE: PRT
<213> ORGANISM: Mus musculus_Heavy chain variable region sequence of
      mAb67

<400> SEQUENCE: 11

Glu Val Gln Leu Gln Gln Ser Gly Pro Glu Leu Val Lys Pro Gly Ala
1               5                   10                  15

Ser Val Lys Ile Tyr Cys Lys Ala Ser Gly Tyr Thr Phe Thr Asp Tyr
            20                  25                  30

His Met Asn Trp Val Lys Gln Ser His Gly Lys Ser Leu Glu Trp Ile
        35                  40                  45

Gly Asp Ile Asn Pro Asp Ile Gly Gly Thr Ser Tyr Asn Gln Asn Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ser Arg Trp Asp Phe Asp Ser Phe Ala Asn Trp Gly Gln Gly Thr Leu
            100                 105                 110

Val Thr Val Ser Ala
```

115

<210> SEQ ID NO 12
<211> LENGTH: 111
<212> TYPE: PRT
<213> ORGANISM: Mus musculus_Light chain variable region sequence of mAb67

<400> SEQUENCE: 12

Asp Ile Val Met Thr Gln Ser Pro Ala Ser Leu Ala Met Ser Leu Gly
1 5 10 15

Lys Arg Ala Thr Ile Ser Cys Arg Ala Ser Glu Ser Val Ser Ile Ile
20 25 30

Gly Thr Asn Leu Ile His Trp Tyr Gln Gln Lys Pro Gly Gln Pro Pro
35 40 45

Lys Leu Leu Ile Tyr His Ala Ser Asn Leu Glu Thr Gly Val Pro Ala
50 55 60

Arg Phe Ser Gly Ser Gly Ser Gly Ala Asp Phe Thr Leu Thr Ile Asp
65 70 75 80

Pro Val Glu Gly Asp Asp Val Ala Leu Tyr Tyr Cys Leu Gln Ser Arg
85 90 95

Lys Ile Pro Tyr Thr Phe Gly Gly Gly Thr Lys Met Glu Ile Lys
100 105 110

<210> SEQ ID NO 13
<211> LENGTH: 122
<212> TYPE: PRT
<213> ORGANISM: Mus musculus_Heavy chain variable region sequence of mAb103

<400> SEQUENCE: 13

Gln Ile Gln Leu Val Gln Ser Gly Pro Glu Leu Lys Lys Pro Gly Glu
1 5 10 15

Thr Val Lys Ile Ser Cys Lys Ala Ser Gly Tyr Thr Phe Thr Thr Tyr
20 25 30

Gly Val Ile Trp Val Lys Gln Ala Pro Gly Lys Gly Leu Lys Trp Met
35 40 45

Gly Trp Ile Asn Thr Tyr Ser Gly Val Pro Thr Tyr Ala Asp Asp Phe
50 55 60

Lys Gly Arg Phe Ala Phe Ser Leu Glu Thr Ser Ala Ser Thr Ala Phe
65 70 75 80

Leu Gln Ile Asn Asn Leu Lys Asn Glu Asp Thr Ala Thr Tyr Phe Cys
85 90 95

Ala Arg Lys Lys Thr Leu Thr Thr Val Thr Pro Trp Phe Ala Tyr Trp
100 105 110

Gly Gln Gly Thr Leu Val Thr Val Ser Ala
115 120

<210> SEQ ID NO 14
<211> LENGTH: 115
<212> TYPE: PRT
<213> ORGANISM: Mus musculus_Light chain variable region sequence of mAb103

<400> SEQUENCE: 14

Asp Leu Val Val Thr Gln Ser Ser Ser Ala Ser Phe Ser Leu Gly Ala
1 5 10 15

Ser Ala Lys Leu Thr Cys Thr Leu Ser Ser Gln His Ser Thr Tyr Thr
20 25 30

```
Ile Glu Trp Tyr Gln Gln Gln Pro Leu Lys Pro Pro Lys Tyr Val Met
        35                  40                  45

Glu Leu Lys Lys Asp Gly Ser His Ser Thr Gly Asp Gly Ile Pro Asp
    50                  55                  60

Arg Phe Ser Gly Ser Ser Ser Gly Ala Asp Arg Tyr Leu Thr Ile Ser
65                  70                  75                  80

Asn Ile Gln Pro Glu Asp Glu Ala Ile Tyr Ile Cys Gly Val Gly Asn
                85                  90                  95

Thr Ile Lys Glu Gln Phe Val Tyr Val Phe Gly Gly Gly Thr Lys Val
            100                 105                 110

Thr Val Leu
        115


<210> SEQ ID NO 15
<211> LENGTH: 5
<212> TYPE: PRT
<213> ORGANISM: Mus musculus_Heavy chain HCDR1 sequence of mAb47

<400> SEQUENCE: 15

Thr Tyr Gly Met Ser
1               5


<210> SEQ ID NO 16
<211> LENGTH: 17
<212> TYPE: PRT
<213> ORGANISM: Mus musculus_Heavy chain HCDR2 sequence of mAb47/mAb103

<400> SEQUENCE: 16

Trp Ile Asn Thr Tyr Ser Gly Val Pro Thr Tyr Ala Asp Asp Phe Lys
1               5                   10                  15

Gly


<210> SEQ ID NO 17
<211> LENGTH: 11
<212> TYPE: PRT
<213> ORGANISM: Mus musculus_Heavy chain HCDR3 sequence of mAb47

<400> SEQUENCE: 17

Arg Gly Asn Tyr Gly Arg Trp Asp Phe Asp Val
1               5                   10


<210> SEQ ID NO 18
<211> LENGTH: 12
<212> TYPE: PRT
<213> ORGANISM: Mus musculus_Light chain LCDR1 sequence of mAb47

<400> SEQUENCE: 18

Ser Val Ser Ser Thr Ile Ser Ser Ser Asn Leu His
1               5                   10


<210> SEQ ID NO 19
<211> LENGTH: 7
<212> TYPE: PRT
<213> ORGANISM: Mus musculus_Light chain LCDR2 sequence of mAb47

<400> SEQUENCE: 19

Gly Thr Ser Asn Leu Ala Ser
1               5


<210> SEQ ID NO 20
<211> LENGTH: 9
```

<212> TYPE: PRT
<213> ORGANISM: Mus musculus_Light chain LCDR3 sequence of mAb47

<400> SEQUENCE: 20

Gln Gln Trp Ser Ile Tyr Pro Leu Thr
1               5

<210> SEQ ID NO 21
<211> LENGTH: 5
<212> TYPE: PRT
<213> ORGANISM: Mus musculus_Heavy chain HCDR1 sequence of mAb63

<400> SEQUENCE: 21

Asp Phe Tyr Met Asn
1               5

<210> SEQ ID NO 22
<211> LENGTH: 17
<212> TYPE: PRT
<213> ORGANISM: Mus musculus_Heavy chain HCDR2 sequence of mAb63

<400> SEQUENCE: 22

Asp Ile Phe Pro Lys Asn Gly Asn Thr Asp Tyr Asn Arg Lys Phe Lys
1               5                   10                  15

Asp

<210> SEQ ID NO 23
<211> LENGTH: 10
<212> TYPE: PRT
<213> ORGANISM: Mus musculus_Heavy chain HCDR3 sequence of mAb63

<400> SEQUENCE: 23

Ser Gly Tyr Gly Asn Tyr Val Phe Asp Tyr
1               5                   10

<210> SEQ ID NO 24
<211> LENGTH: 11
<212> TYPE: PRT
<213> ORGANISM: Mus musculus_Light chain LCDR1 sequence of mAb63

<400> SEQUENCE: 24

Arg Thr Ser Gln Asp Ile Asn Ile Tyr Leu Asn
1               5                   10

<210> SEQ ID NO 25
<211> LENGTH: 7
<212> TYPE: PRT
<213> ORGANISM: Mus musculus_Light chain LCDR2 sequence of mAb63

<400> SEQUENCE: 25

Tyr Arg Ser Gly Leu Leu Ser
1               5

<210> SEQ ID NO 26
<211> LENGTH: 9
<212> TYPE: PRT
<213> ORGANISM: Mus musculus_Light chain LCDR3 sequence of mAb63

<400> SEQUENCE: 26

Gln Gln Gly Asn Thr Leu Pro Pro Thr
1               5

<210> SEQ ID NO 27
<211> LENGTH: 5

-continued

<212> TYPE: PRT
<213> ORGANISM: Mus musculus_Heavy chain HCDR1 sequence of mAb67

<400> SEQUENCE: 27

Asp Tyr His Met Asn
1 5

<210> SEQ ID NO 28
<211> LENGTH: 17
<212> TYPE: PRT
<213> ORGANISM: Mus musculus_Heavy chain HCDR2 sequence of mAb67

<400> SEQUENCE: 28

Asp Ile Asn Pro Asp Ile Gly Gly Thr Ser Tyr Asn Gln Asn Phe Lys
1 5 10 15

Gly

<210> SEQ ID NO 29
<211> LENGTH: 8
<212> TYPE: PRT
<213> ORGANISM: Mus musculus_Heavy chain HCDR3 sequence of mAb67

<400> SEQUENCE: 29

Trp Asp Phe Asp Ser Phe Ala Asn
1 5

<210> SEQ ID NO 30
<211> LENGTH: 15
<212> TYPE: PRT
<213> ORGANISM: Mus musculus_Light chain LCDR1 sequence of mAb67

<400> SEQUENCE: 30

Arg Ala Ser Glu Ser Val Ser Ile Ile Gly Thr Asn Leu Ile His
1 5 10 15

<210> SEQ ID NO 31
<211> LENGTH: 7
<212> TYPE: PRT
<213> ORGANISM: Mus musculus_Light chain LCDR2 sequence of mAb67

<400> SEQUENCE: 31

His Ala Ser Asn Leu Glu Thr
1 5

<210> SEQ ID NO 32
<211> LENGTH: 9
<212> TYPE: PRT
<213> ORGANISM: Mus musculus_Light chain LCDR3 sequence of mAb67

<400> SEQUENCE: 32

Leu Gln Ser Arg Lys Ile Pro Tyr Thr
1 5

<210> SEQ ID NO 33
<211> LENGTH: 5
<212> TYPE: PRT
<213> ORGANISM: Mus musculus_Heavy chain HCDR1 sequence of mAb103

<400> SEQUENCE: 33

Thr Tyr Gly Val Ile
1 5

<210> SEQ ID NO 34
<211> LENGTH: 13

<212> TYPE: PRT
<213> ORGANISM: Mus musculus_Heavy chain HCDR3 sequence of mAb103

<400> SEQUENCE: 34

```
Lys Lys Thr Leu Thr Thr Val Thr Pro Trp Phe Ala Tyr
1               5                   10
```

<210> SEQ ID NO 35
<211> LENGTH: 12
<212> TYPE: PRT
<213> ORGANISM: Mus musculus_Light chain LCDR1 sequence of mAb103

<400> SEQUENCE: 35

```
Thr Leu Ser Ser Gln His Ser Thr Tyr Thr Ile Glu
1               5                   10
```

<210> SEQ ID NO 36
<211> LENGTH: 11
<212> TYPE: PRT
<213> ORGANISM: Mus musculus_Light chain LCDR2 sequence of mAb103

<400> SEQUENCE: 36

```
Leu Lys Lys Asp Gly Ser His Ser Thr Gly Asp
1               5                   10
```

<210> SEQ ID NO 37
<211> LENGTH: 13
<212> TYPE: PRT
<213> ORGANISM: Mus musculus_Light chain LCDR3 sequence of mAb103

<400> SEQUENCE: 37

```
Gly Val Gly Asn Thr Ile Lys Glu Gln Phe Val Tyr Val
1               5                   10
```

<210> SEQ ID NO 38
<211> LENGTH: 17
<212> TYPE: PRT
<213> ORGANISM: Artificial Sequence
<220> FEATURE:
<223> OTHER INFORMATION: Synthetic Sequence_Heavy chain HCDR2 mutant (D61S) sequence of mAb47/mAb103

<400> SEQUENCE: 38

```
Trp Ile Asn Thr Tyr Ser Gly Val Pro Thr Tyr Ala Ser Asp Phe Lys
1               5                   10                  15

Gly
```

<210> SEQ ID NO 39
<211> LENGTH: 120
<212> TYPE: PRT
<213> ORGANISM: Artificial Sequence
<220> FEATURE:
<223> OTHER INFORMATION: Synthetic Sequence_Humanized antibody heavy chain variable region h47VH1 sequence of mAb47

<400> SEQUENCE: 39

```
Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Tyr
            20                  25                  30

Gly Met Ser Trp Val Arg Gln Ala Pro Gly Gln Gly Leu Glu Trp Met
        35                  40                  45

Gly Trp Ile Asn Thr Tyr Ser Gly Val Pro Thr Tyr Ala Asp Asp Phe
    50                  55                  60
```

```
Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Arg Gly Asn Tyr Gly Arg Trp Asp Phe Asp Val Trp Gly Gln
            100                 105                 110

Gly Thr Thr Val Thr Val Ser Ser
        115                 120
```

<210> SEQ ID NO 40
<211> LENGTH: 120
<212> TYPE: PRT
<213> ORGANISM: Artificial Sequence
<220> FEATURE:
<223> OTHER INFORMATION: Synthetic Sequence_Humanized antibody heavy chain variable region h47VH2 sequence of mAb47

<400> SEQUENCE: 40

```
Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Tyr
            20                  25                  30

Gly Met Ser Trp Val Arg Gln Ala Pro Gly Gln Gly Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Arg Gly Asn Tyr Gly Arg Trp Asp Phe Asp Val Trp Gly Gln
            100                 105                 110

Gly Thr Thr Val Thr Val Ser Ser
        115                 120
```

<210> SEQ ID NO 41
<211> LENGTH: 120
<212> TYPE: PRT
<213> ORGANISM: Artificial Sequence
<220> FEATURE:
<223> OTHER INFORMATION: Synthetic Sequence_Humanized antibody heavy chain variable region h47VH3 sequence of mAb47

<400> SEQUENCE: 41

```
Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Tyr
            20                  25                  30

Gly Met Ser Trp Val Lys Gln Ala Pro Gly Gln Gly Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Arg Gly Asn Tyr Gly Arg Trp Asp Phe Asp Val Trp Gly Gln
            100                 105                 110
```

Gly Thr Thr Val Thr Val Ser Ser
115 120

<210> SEQ ID NO 42
<211> LENGTH: 120
<212> TYPE: PRT
<213> ORGANISM: Artificial Sequence
<220> FEATURE:
<223> OTHER INFORMATION: Synthetic Sequence_Humanized antibody heavy chain variable region h47VH4 sequence of mAb47

<400> SEQUENCE: 42

Glu Val Gln Leu Val Gln Ser Gly Ser Glu Leu Lys Lys Pro Gly Ala
1 5 10 15

Ser Val Lys Val Ser Cys Lys Ala Ser Gly Tyr Thr Phe Thr Thr Tyr
20 25 30

Gly Met Ser Trp Val Lys Gln Ala Pro Gly Gln Gly Leu Lys Trp Met
35 40 45

Gly Trp Ile Asn Thr Tyr Ser Gly Val Pro Thr Tyr Ala Ser Asp Phe
50 55 60

Lys Gly Arg Phe Val Phe Ser Leu Asp Thr Ser Val Ser Thr Ala Tyr
65 70 75 80

Leu Gln Ile Ser Ser Leu Lys Ala Glu Asp Thr Ala Val Tyr Tyr Cys
85 90 95

Ala Arg Arg Gly Asn Tyr Gly Arg Trp Asp Phe Asp Val Trp Gly Gln
100 105 110

Gly Thr Thr Val Thr Val Ser Ser
115 120

<210> SEQ ID NO 43
<211> LENGTH: 108
<212> TYPE: PRT
<213> ORGANISM: Artificial Sequence
<220> FEATURE:
<223> OTHER INFORMATION: Synthetic Sequence_Humanized antibody light chain variable region h47VL1 sequence of mAb47

<400> SEQUENCE: 43

Glu Ile Val Leu Thr Gln Ser Pro Asp Phe Gln Ser Val Thr Pro Lys
1 5 10 15

Glu Lys Val Thr Ile Thr Cys Ser Val Ser Ser Thr Ile Ser Ser Ser
20 25 30

Asn Leu His Trp Tyr Gln Gln Lys Pro Asp Gln Ser Pro Lys Leu Leu
35 40 45

Ile Lys Gly Thr Ser Asn Leu Ala Ser Gly Val Pro Ser Arg Phe Ser
50 55 60

Gly Ser Gly Ser Gly Thr Asp Phe Thr Leu Thr Ile Asn Ser Leu Glu
65 70 75 80

Ala Glu Asp Ala Ala Thr Tyr Tyr Cys Gln Gln Trp Ser Ile Tyr Pro
85 90 95

Leu Thr Phe Gly Gln Gly Thr Lys Leu Glu Ile Lys
100 105

<210> SEQ ID NO 44
<211> LENGTH: 108
<212> TYPE: PRT
<213> ORGANISM: Artificial Sequence
<220> FEATURE:
<223> OTHER INFORMATION: Synthetic Sequence_Humanized antibody light chain variable region h47VL2 sequence of mAb47

<400> SEQUENCE: 44

Glu Ile Val Leu Thr Gln Ser Pro Asp Phe Gln Ser Val Thr Pro Lys
1 5 10 15

Glu Lys Val Thr Ile Thr Cys Ser Val Ser Ser Thr Ile Ser Ser Ser
20 25 30

Asn Leu His Trp Tyr Gln Gln Lys Pro Asp Gln Ser Pro Lys Pro Leu
35 40 45

Ile Tyr Gly Thr Ser Asn Leu Ala Ser Gly Val Pro Ser Arg Phe Ser
50 55 60

Gly Ser Gly Ser Gly Thr Asp Tyr Thr Leu Thr Ile Asn Ser Leu Glu
65 70 75 80

Ala Glu Asp Ala Ala Thr Tyr Tyr Cys Gln Gln Trp Ser Ile Tyr Pro
85 90 95

Leu Thr Phe Gly Gln Gly Thr Lys Leu Glu Ile Lys
100 105

<210> SEQ ID NO 45
<211> LENGTH: 108
<212> TYPE: PRT
<213> ORGANISM: Artificial Sequence
<220> FEATURE:
<223> OTHER INFORMATION: Synthetic Sequence_Humanized antibody light chain variable region h47VL3 sequence of mAb47

<400> SEQUENCE: 45

Glu Ile Val Leu Thr Gln Ser Pro Asp Phe Gln Ser Val Thr Pro Lys
1 5 10 15

Glu Lys Val Thr Ile Thr Cys Ser Val Ser Ser Thr Ile Ser Ser Ser
20 25 30

Asn Leu His Trp Tyr Gln Gln Lys Pro Asp Gln Ser Pro Lys Pro Trp
35 40 45

Ile Tyr Gly Thr Ser Asn Leu Ala Ser Gly Val Pro Ser Arg Phe Ser
50 55 60

Gly Ser Gly Ser Gly Thr Asp Tyr Thr Leu Thr Ile Asn Ser Leu Glu
65 70 75 80

Ala Glu Asp Ala Ala Thr Tyr Tyr Cys Gln Gln Trp Ser Ile Tyr Pro
85 90 95

Leu Thr Phe Gly Gln Gly Thr Lys Leu Glu Ile Lys
100 105

<210> SEQ ID NO 46
<211> LENGTH: 108
<212> TYPE: PRT
<213> ORGANISM: Artificial Sequence
<220> FEATURE:
<223> OTHER INFORMATION: Synthetic Sequence_Humanized antibody light chain variable region h47VL4 sequence of mAb47

<400> SEQUENCE: 46

Glu Ile Val Leu Thr Gln Ser Pro Asp Phe Gln Ser Val Thr Pro Lys
1 5 10 15

Glu Lys Val Thr Ile Thr Cys Ser Val Ser Ser Thr Ile Ser Ser Ser
20 25 30

Asn Leu His Trp Tyr Gln Gln Lys Pro Asp Gln Ser Pro Lys Pro Trp
35 40 45

Ile Tyr Gly Thr Ser Asn Leu Ala Ser Gly Val Pro Ser Arg Phe Ser
50 55 60

```
Gly Ser Gly Ser Gly Thr Ser Tyr Thr Leu Thr Ile Asn Ser Leu Glu
65                  70                  75                  80

Ala Glu Asp Ala Ala Thr Tyr Tyr Cys Gln Gln Trp Ser Ile Tyr Pro
                85                  90                  95

Leu Thr Phe Gly Gln Gly Thr Lys Leu Glu Ile Lys
            100                 105


<210> SEQ ID NO 47
<211> LENGTH: 17
<212> TYPE: PRT
<213> ORGANISM: Artificial Sequence
<220> FEATURE:
<223> OTHER INFORMATION: Synthetic Sequence_Heavy chain HCDR2 mutant
      (N54S) sequence of mAb63

<400> SEQUENCE: 47

Asp Ile Phe Pro Lys Ser Gly Asn Thr Asp Tyr Asn Arg Lys Phe Lys
1               5                   10                  15

Asp


<210> SEQ ID NO 48
<211> LENGTH: 119
<212> TYPE: PRT
<213> ORGANISM: Artificial Sequence
<220> FEATURE:
<223> OTHER INFORMATION: Synthetic Sequence_Humanized antibody heavy
      chain variable region h63VH1 sequence of mAb63

<400> SEQUENCE: 48

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Tyr Met Asn Trp Val Arg Gln Ala Pro Gly Gln Gly Leu Glu Trp Met
        35                  40                  45

Gly Asp Ile Phe Pro Lys Asn Gly Asn Thr Asp Tyr Asn Arg Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Gly Asn Tyr Val Phe Asp Tyr Trp Gly Gln Gly
            100                 105                 110

Thr Leu Val Thr Val Ser Ser
        115


<210> SEQ ID NO 49
<211> LENGTH: 119
<212> TYPE: PRT
<213> ORGANISM: Artificial Sequence
<220> FEATURE:
<223> OTHER INFORMATION: Synthetic Sequence_Humanized antibody heavy
      chain variable region h63VH2 sequence of mAb63

<400> SEQUENCE: 49

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Tyr Met Asn Trp Val Arg Gln Ala Pro Gly Gln Gly Leu Glu Trp Met
        35                  40                  45
```

```
Gly Asp Ile Phe Pro Lys Asn Gly Asn Thr Asp Tyr Asn Arg Lys Phe
    50                  55                  60

Lys Asp Arg Val Thr Leu Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Gly Asn Tyr Val Phe Asp Tyr Trp Gly Gln Gly
            100                 105                 110

Thr Leu Val Thr Val Ser Ser
        115


<210> SEQ ID NO 50
<211> LENGTH: 119
<212> TYPE: PRT
<213> ORGANISM: Artificial Sequence
<220> FEATURE:
<223> OTHER INFORMATION: Synthetic Sequence_Humanized antibody heavy
      chain variable region h63VH3 sequence of mAb63

<400> SEQUENCE: 50

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Tyr Met Asn Trp Val Arg Gln Ala Pro Gly Gln Gly Leu Glu Trp Ile
        35                  40                  45

Gly Asp Ile Phe Pro Lys Asn Gly Asn Thr Asp Tyr Asn Arg Lys Phe
    50                  55                  60

Lys Asp Arg Ala Thr Leu Thr Val Asp Lys Ser Thr Ser Thr Val Tyr
65                  70                  75                  80

Met Glu Phe Ser Ser Leu Arg Ser Glu Asp Thr Ala Val Tyr Tyr Cys
                85                  90                  95

Ala Arg Ser Gly Tyr Gly Asn Tyr Val Phe Asp Tyr Trp Gly Gln Gly
            100                 105                 110

Thr Leu Val Thr Val Ser Ser
        115


<210> SEQ ID NO 51
<211> LENGTH: 119
<212> TYPE: PRT
<213> ORGANISM: Artificial Sequence
<220> FEATURE:
<223> OTHER INFORMATION: Synthetic Sequence_Humanized antibody heavy
      chain variable region h63VH4 sequence of mAb63

<400> SEQUENCE: 51

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Tyr Met Asn Trp Val Arg Gln Ala Pro Gly Gln Gly Leu Glu Trp Ile
        35                  40                  45

Gly Asp Ile Phe Pro Lys Asn Gly Asn Thr Asp Tyr Asn Arg Lys Phe
    50                  55                  60

Lys Asp Lys Ala Thr Leu Thr Val Asp Lys Ser Thr Ser Thr Val Tyr
65                  70                  75                  80

Met Glu Phe Arg Ser Leu Arg Ser Glu Asp Thr Ala Val Tyr Tyr Cys
                85                  90                  95
```

```
Ala Arg Ser Gly Tyr Gly Asn Tyr Val Phe Asp Tyr Trp Gly Gln Gly
            100                 105                 110

Thr Leu Val Thr Val Ser Ser
        115


<210> SEQ ID NO 52
<211> LENGTH: 119
<212> TYPE: PRT
<213> ORGANISM: Artificial Sequence
<220> FEATURE:
<223> OTHER INFORMATION: Synthetic Sequence_Humanized antibody heavy
      chain variable region h63VH5 sequence of mAb63

<400> SEQUENCE: 52

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Tyr Met Asn Trp Val Arg Gln Ala Pro Gly Gln Gly Leu Glu Trp Met
        35                  40                  45

Gly Asp Ile Phe Pro Lys Ser Gly Asn Thr Asp Tyr Asn Arg Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Gly Asn Tyr Val Phe Asp Tyr Trp Gly Gln Gly
            100                 105                 110

Thr Leu Val Thr Val Ser Ser
        115


<210> SEQ ID NO 53
<211> LENGTH: 107
<212> TYPE: PRT
<213> ORGANISM: Artificial Sequence
<220> FEATURE:
<223> OTHER INFORMATION: Synthetic Sequence_Humanized antibody light
      chain variable region h63VL1 sequence of mAb63

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Asn Ile Tyr
            20                  25                  30

Leu Asn Trp Tyr Gln Gln Lys Pro Gly Lys Ala Pro Lys Leu Leu Ile
        35                  40                  45

Tyr Tyr Arg Ser Gly Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Pro
                85                  90                  95

Thr Phe Gly Gly Gly Thr Lys Val Glu Ile Lys
            100                 105


<210> SEQ ID NO 54
<211> LENGTH: 107
<212> TYPE: PRT
<213> ORGANISM: Artificial Sequence
```

<220> FEATURE:
<223> OTHER INFORMATION: Synthetic Sequence_Humanized antibody light chain variable region h63VL2 sequence of mAb63

<400> SEQUENCE: 54

```
Asp Val Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Asn Ile Tyr
            20                  25                  30

Leu Asn Trp Tyr Gln Gln Lys Pro Gly Lys Ala Pro Lys Leu Leu Ile
        35                  40                  45

Tyr Tyr Arg Ser Gly Leu Leu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Pro
                85                  90                  95

Thr Phe Gly Gly Gly Thr Lys Val Glu Ile Lys
            100                 105
```

<210> SEQ ID NO 55
<211> LENGTH: 107
<212> TYPE: PRT
<213> ORGANISM: Artificial Sequence
<220> FEATURE:
<223> OTHER INFORMATION: Synthetic Sequence_Humanized antibody light chain variable region h63VL3 sequence of mAb63

<400> SEQUENCE: 55

```
Asp Val Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Asn Ile Tyr
            20                  25                  30

Leu Asn Trp Tyr Gln Gln Lys Pro Gly Gly Ala Val Lys Leu Leu Ile
        35                  40                  45

Tyr Tyr Arg Ser Gly Leu Leu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Pro
                85                  90                  95

Thr Phe Gly Gly Gly Thr Lys Val Glu Ile Lys
            100                 105
```

<210> SEQ ID NO 56
<211> LENGTH: 117
<212> TYPE: PRT
<213> ORGANISM: Artificial Sequence
<220> FEATURE:
<223> OTHER INFORMATION: Synthetic Sequence_Humanized antibody heavy chain variable region h67VH1 sequence of mAb67

<400> SEQUENCE: 56

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

His Met Asn Trp Val Arg Gln Ala Pro Gly Gln Arg Leu Glu Trp Met
        35                  40                  45
```

-continued

```
Gly Asp Ile Asn Pro Asp Ile Gly Gly Thr Ser Tyr Asn Gln Asn Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Phe Asp Ser Phe Ala Asn Trp Gly Gln Gly Thr Leu
            100                 105                 110

Val Thr Val Ser Ser
        115


<210> SEQ ID NO 57
<211> LENGTH: 117
<212> TYPE: PRT
<213> ORGANISM: Artificial Sequence
<220> FEATURE:
<223> OTHER INFORMATION: Synthetic Sequence_Humanized antibody heavy
      chain variable region h67VH2 sequence of mAb67

<400> SEQUENCE: 57

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

His Met Asn Trp Val Arg Gln Met Pro Gly Lys Gly Leu Glu Trp Met
        35                  40                  45

Gly Asp Ile Asn Pro Asp Ile Gly Gly Thr Ser Tyr Asn Gln Asn Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Asp Phe Asp Ser Phe Ala Asn Trp Gly Gln Gly Thr Leu
            100                 105                 110

Val Thr Val Ser Ser
        115


<210> SEQ ID NO 58
<211> LENGTH: 117
<212> TYPE: PRT
<213> ORGANISM: Artificial Sequence
<220> FEATURE:
<223> OTHER INFORMATION: Synthetic Sequence_Humanized antibody heavy
      chain variable region h67VH3 sequence of mAb67

<400> SEQUENCE: 58

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

His Met Asn Trp Val Lys Gln Met Pro Gly Lys Gly Leu Glu Trp Met
        35                  40                  45

Gly Asp Ile Asn Pro Asp Ile Gly Gly Thr Ser Tyr Asn Gln Asn Phe
    50                  55                  60

Lys Gly Lys Val Thr Ile Ser Val Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95
```

-continued

```
Ala Arg Trp Asp Phe Asp Ser Phe Ala Asn Trp Gly Gln Gly Thr Leu
            100                 105                 110

Val Thr Val Ser Ser
        115


<210> SEQ ID NO 59
<211> LENGTH: 111
<212> TYPE: PRT
<213> ORGANISM: Artificial Sequence
<220> FEATURE:
<223> OTHER INFORMATION: Synthetic Sequence_Humanized antibody light
      chain variable region h67VL1 sequence of mAb67

<400> SEQUENCE: 59

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Ser Ile Ile
            20                  25                  30

Gly Thr Asn Leu Ile His Trp Tyr Gln Gln Lys Pro Gly Gln Pro Pro
        35                  40                  45

Lys Leu Leu Ile Tyr His Ala Ser Asn Leu Glu Thr Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Leu Gln Ser Arg
                85                  90                  95

Lys Ile Pro Tyr Thr Phe Gly Gly Gly Thr Lys Val Glu Ile Lys
            100                 105                 110


<210> SEQ ID NO 60
<211> LENGTH: 111
<212> TYPE: PRT
<213> ORGANISM: Artificial Sequence
<220> FEATURE:
<223> OTHER INFORMATION: Synthetic Sequence_Humanized antibody light
      chain variable region h67VL2 sequence of mAb67

<400> SEQUENCE: 60

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ser Ile Ile
            20                  25                  30

Gly Thr Asn Leu Ile His Trp Tyr Gln Gln Lys Pro Gly Gln Ala Pro
        35                  40                  45

Arg Leu Leu Ile Tyr His Ala Ser Asn Leu Glu Thr Gly Ile Pro Ala
    50                  55                  60

Arg Phe Ser Gly Ser Gly Ser Gly Thr Glu Phe Thr Leu Thr Ile Ser
65                  70                  75                  80

Ser Leu Gln Ser Glu Asp Phe Ala Val Tyr Tyr Cys Leu Gln Ser Arg
                85                  90                  95

Lys Ile Pro Tyr Thr Phe Gly Gly Gly Thr Lys Val Glu Ile Lys
            100                 105                 110


<210> SEQ ID NO 61
<211> LENGTH: 111
<212> TYPE: PRT
<213> ORGANISM: Artificial Sequence
<220> FEATURE:
<223> OTHER INFORMATION: Synthetic Sequence_Humanized antibody light
      chain variable region h67VL3 sequence of mAb67
```

```
<400> SEQUENCE: 61

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ser Ile Ile
            20                  25                  30

Gly Thr Asn Leu Ile His Trp Tyr Gln Gln Lys Pro Gly Gln Pro Pro
        35                  40                  45

Arg Leu Leu Ile Tyr His Ala Ser Asn Leu Glu Thr Gly Val Pro Ala
    50                  55                  60

Arg Phe Ser Gly Ser Gly Ser Gly Thr Glu Phe Thr Leu Thr Ile Ser
65                  70                  75                  80

Ser Leu Gln Ser Glu Asp Phe Ala Val Tyr Tyr Cys Leu Gln Ser Arg
                85                  90                  95

Lys Ile Pro Tyr Thr Phe Gly Gly Gly Thr Lys Val Glu Ile Lys
            100                 105                 110


<210> SEQ ID NO 62
<211> LENGTH: 111
<212> TYPE: PRT
<213> ORGANISM: Artificial Sequence
<220> FEATURE:
<223> OTHER INFORMATION: Synthetic Sequence_Humanized antibody light
      chain variable region h67VL4 sequence of mAb67

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Ser Ile Ile
            20                  25                  30

Gly Thr Asn Leu Ile His Trp Tyr Gln Gln Lys Pro Gly Lys Ala Pro
        35                  40                  45

Lys Leu Leu Ile Tyr His Ala Ser Asn Leu Glu Thr Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Leu Gln Ser Arg
                85                  90                  95

Lys Ile Pro Tyr Thr Phe Gly Gly Gly Thr Lys Val Glu Ile Lys
            100                 105                 110


<210> SEQ ID NO 63
<211> LENGTH: 111
<212> TYPE: PRT
<213> ORGANISM: Artificial Sequence
<220> FEATURE:
<223> OTHER INFORMATION: Synthetic Sequence_Humanized antibody light
      chain variable region h67VL5 sequence of mAb67

<400> SEQUENCE: 63

Asp Ile Val Met Thr Gln Ser Pro Ser Ser Leu Ser Ala Ser Val Gly
1               5                   10                  15

Asp Arg Val Thr Ile Thr Cys Arg Ala Ser Glu Ser Val Ser Ile Ile
            20                  25                  30

Gly Thr Asn Leu Ile His Trp Tyr Gln Gln Lys Pro Gly Lys Pro Pro
        35                  40                  45

Lys Leu Leu Ile Tyr His Ala Ser Asn Leu Glu Thr Gly Val Pro Ser
    50                  55                  60

Arg Phe Ser Gly Ser Gly Ser Gly Thr Asp Phe Thr Leu Thr Ile Ser
```

```
65                  70                  75                  80

Ser Leu Gln Pro Glu Asp Phe Ala Thr Tyr Tyr Cys Leu Gln Ser Arg
                85                  90                  95

Lys Ile Pro Tyr Thr Phe Gly Gly Gly Thr Lys Val Glu Ile Lys
            100                 105                 110
```

<210> SEQ ID NO 64
<211> LENGTH: 11
<212> TYPE: PRT
<213> ORGANISM: Artificial Sequence
<220> FEATURE:
<223> OTHER INFORMATION: Synthetic Sequence_Light chain LCDR2 mutant (D56E) sequence of mAb103

<400> SEQUENCE: 64

```
Leu Lys Lys Asp Gly Ser His Ser Thr Gly Glu
1               5                   10
```

<210> SEQ ID NO 65
<211> LENGTH: 122
<212> TYPE: PRT
<213> ORGANISM: Artificial Sequence
<220> FEATURE:
<223> OTHER INFORMATION: Synthetic Sequence_Humanized antibody heavy chain variable region h103VH1 sequence of mAb103

<400> SEQUENCE: 65

```
Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Tyr
            20                  25                  30

Gly Val Ile Trp Val Arg Gln Ala Pro Gly Gln Gly Leu Glu Trp Met
        35                  40                  45

Gly Trp Ile Asn Thr Tyr Ser Gly Val Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Lys Lys Thr Leu Thr Thr Val Thr Pro Trp Phe Ala Tyr Trp
            100                 105                 110

Gly Gln Gly Thr Leu Val Thr Val Ser Ser
        115                 120
```

<210> SEQ ID NO 66
<211> LENGTH: 122
<212> TYPE: PRT
<213> ORGANISM: Artificial Sequence
<220> FEATURE:
<223> OTHER INFORMATION: Synthetic Sequence_Humanized antibody heavy chain variable region h103VH2 sequence of mAb103

<400> SEQUENCE: 66

```
Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Tyr
            20                  25                  30

Gly Val Ile Trp Val Lys Gln Ala Pro Gly Gln Gly Leu Lys Trp Met
        35                  40                  45

Gly Trp Ile Asn Thr Tyr Ser Gly Val Pro Thr Tyr Ala Asp Asp Phe
    50                  55                  60
```

-continued

```
Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Lys Lys Thr Leu Thr Thr Val Thr Pro Trp Phe Ala Tyr Trp
            100                 105                 110

Gly Gln Gly Thr Leu Val Thr Val Ser Ser
        115                 120


<210> SEQ ID NO 67
<211> LENGTH: 122
<212> TYPE: PRT
<213> ORGANISM: Artificial Sequence
<220> FEATURE:
<223> OTHER INFORMATION: Synthetic Sequence_Humanized antibody heavy
      chain variable region h103VH3 sequence of mAb103

<400> SEQUENCE: 67

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Tyr
            20                  25                  30

Gly Val Ile Trp Val Lys Gln Ala Pro Gly Gln Gly Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Lys Lys Thr Leu Thr Thr Val Thr Pro Trp Phe Ala Tyr Trp
            100                 105                 110

Gly Gln Gly Thr Leu Val Thr Val Ser Ser
        115                 120


<210> SEQ ID NO 68
<211> LENGTH: 122
<212> TYPE: PRT
<213> ORGANISM: Artificial Sequence
<220> FEATURE:
<223> OTHER INFORMATION: Synthetic Sequence_Humanized antibody heavy
      chain variable region h103VH4 sequence of mAb103

<400> SEQUENCE: 68

Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Tyr
            20                  25                  30

Gly Val Ile Trp Val Arg Gln Ala Pro Gly Gln Gly Leu Glu Trp Met
        35                  40                  45

Gly Trp Ile Asn Thr Tyr Ser Gly Val Pro Thr Tyr Ala Ser Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Lys Lys Thr Leu Thr Thr Val Thr Pro Trp Phe Ala Tyr Trp
            100                 105                 110
```

```
Gly Gln Gly Thr Leu Val Thr Val Ser Ser
        115                 120


<210> SEQ ID NO 69
<211> LENGTH: 115
<212> TYPE: PRT
<213> ORGANISM: Artificial Sequence
<220> FEATURE:
<223> OTHER INFORMATION: Synthetic Sequence_Humanized antibody light
      chain variable region h103VL1 sequence of mAb103

<400> SEQUENCE: 69

Glu Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

Ile Glu Trp His Gln Gln Gln Pro Glu Lys Gly Pro Arg Tyr Leu Met
        35                  40                  45

Glu Leu Lys Lys Asp Gly Ser His Ser Thr Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asn
                85                  90                  95

Thr Ile Lys Glu Gln Phe Val Tyr Val Phe Gly Gly Gly Thr Lys Leu
            100                 105                 110

Thr Val Leu
        115


<210> SEQ ID NO 70
<211> LENGTH: 115
<212> TYPE: PRT
<213> ORGANISM: Artificial Sequence
<220> FEATURE:
<223> OTHER INFORMATION: Synthetic Sequence_Humanized antibody light
      chain variable region h103VL2 sequence of mAb103

<400> SEQUENCE: 70

Glu Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

Ile Glu Trp Tyr Gln Gln Gln Pro Glu Lys Gly Pro Arg Tyr Leu Met
        35                  40                  45

Glu Leu Lys Lys Asp Gly Ser His Ser Thr Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asn
                85                  90                  95

Thr Ile Lys Glu Gln Phe Val Tyr Val Phe Gly Gly Gly Thr Lys Leu
            100                 105                 110

Thr Val Leu
        115


<210> SEQ ID NO 71
<211> LENGTH: 115
<212> TYPE: PRT
<213> ORGANISM: Artificial Sequence
```

-continued

<220> FEATURE:
<223> OTHER INFORMATION: Synthetic Sequence_Humanized antibody light chain variable region h103VL3 sequence of mAb103

<400> SEQUENCE: 71

```
Glu Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

Ile Glu Trp Tyr Gln Gln Gln Pro Glu Lys Gly Pro Arg Tyr Val Met
        35                  40                  45

Glu Leu Lys Lys Asp Gly Ser His Ser Thr Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asn
                85                  90                  95

Thr Ile Lys Glu Gln Phe Val Tyr Val Phe Gly Gly Gly Thr Lys Leu
            100                 105                 110

Thr Val Leu
        115
```

<210> SEQ ID NO 72
<211> LENGTH: 115
<212> TYPE: PRT
<213> ORGANISM: Artificial Sequence
<220> FEATURE:
<223> OTHER INFORMATION: Synthetic Sequence_Humanized antibody light chain variable region h103VL4 sequence of mAb103

<400> SEQUENCE: 72

```
Glu Leu Val Val Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

Ile Glu Trp Tyr Gln Gln Gln Pro Glu Lys Gly Pro Arg Tyr Val Met
        35                  40                  45

Glu Leu Lys Lys Asp Gly Ser His Ser Thr Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asn
                85                  90                  95

Thr Ile Lys Glu Gln Phe Val Tyr Val Phe Gly Gly Gly Thr Lys Leu
            100                 105                 110

Thr Val Leu
        115
```

<210> SEQ ID NO 73
<211> LENGTH: 115
<212> TYPE: PRT
<213> ORGANISM: Artificial Sequence
<220> FEATURE:
<223> OTHER INFORMATION: Synthetic Sequence_Humanized antibody light chain variable region h103VL5 sequence of mAb103

<400> SEQUENCE: 73

```
Glu Leu Val Leu Thr Gln Ser Pro Ser Ala Ser Ala Ser Leu Gly Ala
1               5                   10                  15
```

-continued

```
Ser Val Lys Leu Thr Cys Thr Leu Ser Ser Gln His Ser Thr Tyr Thr
            20                  25                  30

Ile Glu Trp Tyr Gln Gln Gln Pro Glu Lys Pro Pro Arg Tyr Val Met
        35                  40                  45

Glu Leu Lys Lys Asp Gly Ser His Ser Thr Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Ile Cys Gly Val Gly Asn
                85                  90                  95

Thr Ile Lys Glu Gln Phe Val Tyr Val Phe Gly Gly Gly Thr Lys Leu
            100                 105                 110

Thr Val Leu
        115


<210> SEQ ID NO 74
<211> LENGTH: 115
<212> TYPE: PRT
<213> ORGANISM: Artificial Sequence
<220> FEATURE:
<223> OTHER INFORMATION: Synthetic Sequence_Humanized antibody light
      chain variable region h103VL6 sequence of mAb103

<400> SEQUENCE: 74

Glu Leu Val Val Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

Ile Glu Trp Tyr Gln Gln Gln Pro Glu Lys Pro Pro Arg Tyr Val Met
        35                  40                  45

Glu Leu Lys Lys Asp Gly Ser His Ser Thr Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Ile Cys Gly Val Gly Asn
                85                  90                  95

Thr Ile Lys Glu Gln Phe Val Tyr Val Phe Gly Gly Gly Thr Lys Leu
            100                 105                 110

Thr Val Leu
        115


<210> SEQ ID NO 75
<211> LENGTH: 115
<212> TYPE: PRT
<213> ORGANISM: Artificial Sequence
<220> FEATURE:
<223> OTHER INFORMATION: Synthetic Sequence_Humanized antibody light
      chain variable region h103VL7 sequence of mAb103

<400> SEQUENCE: 75

Glu Leu Val Val Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

Ile Glu Trp Tyr Gln Gln Gln Pro Glu Lys Pro Pro Arg Tyr Val Met
        35                  40                  45

Glu Leu Lys Lys Asp Gly Ser His Ser Thr Gly Asp Gly Ile Pro Asp
    50                  55                  60
```

-continued

```
Arg Phe Ser Gly Ser Ser Ser Gly Ala Asp Arg Tyr Leu Thr Ile Ser
65                  70                  75                  80

Ser Leu Gln Ser Glu Asp Glu Ala Asp Tyr Ile Cys Gly Val Gly Asn
                85                  90                  95

Thr Ile Lys Glu Gln Phe Val Tyr Val Phe Gly Gly Gly Thr Lys Leu
            100                 105                 110

Thr Val Leu
        115


<210> SEQ ID NO 76
<211> LENGTH: 115
<212> TYPE: PRT
<213> ORGANISM: Artificial Sequence
<220> FEATURE:
<223> OTHER INFORMATION: Synthetic Sequence_Humanized antibody light
      chain variable region h103VL8 sequence of mAb103

<400> SEQUENCE: 76

Glu Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

Ile Glu Trp Tyr Gln Gln Gln Pro Glu Lys Gly Pro Arg Tyr Val Met
        35                  40                  45

Glu Leu Lys Lys Asp Gly Ser His Ser Thr Gly Glu Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asn
                85                  90                  95

Thr Ile Lys Glu Gln Phe Val Tyr Val Phe Gly Gly Gly Thr Lys Leu
            100                 105                 110

Thr Val Leu
        115


<210> SEQ ID NO 77
<211> LENGTH: 330
<212> TYPE: PRT
<213> ORGANISM: Artificial Sequence
<220> FEATURE:
<223> OTHER INFORMATION: Synthetic Sequence_Heavy chain constant region
      of human IgG1

<400> SEQUENCE: 77

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

-continued

```
Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 78
<211> LENGTH: 107
<212> TYPE: PRT
<213> ORGANISM: Artificial Sequence
<220> FEATURE:
<223> OTHER INFORMATION: Synthetic Sequence_Human light chain constant
      region chain sequence

<400> SEQUENCE: 78

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 79
<211> LENGTH: 106
<212> TYPE: PRT
<213> ORGANISM: Artificial Sequence
```

```
<220> FEATURE:
<223> OTHER INFORMATION: Synthetic Sequence_Human light chain constant
      region chain sequence

<400> SEQUENCE: 79

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 80
<211> LENGTH: 449
<212> TYPE: PRT
<213> ORGANISM: Artificial Sequence
<220> FEATURE:
<223> OTHER INFORMATION: Synthetic Sequence_Heavy chain sequence of
      Hu63-13

<400> SEQUENCE: 80

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Tyr Met Asn Trp Val Arg Gln Ala Pro Gly Gln Gly Leu Glu Trp Met
        35                  40                  45

Gly Asp Ile Phe Pro Lys Ser Gly Asn Thr Asp Tyr Asn Arg Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Gly Asn Tyr Val Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 81
<211> LENGTH: 214
<212> TYPE: PRT
<213> ORGANISM: Artificial Sequence
<220> FEATURE:
<223> OTHER INFORMATION: Synthetic Sequence_Light chain sequence of Hu63-13

<400> SEQUENCE: 81

Asp Ile Gln Met Thr Gln Ser Pro Ser Ser Leu Ser Ala Ser Val Gly
1 5 10 15

Asp Arg Val Thr Ile Thr Cys Arg Thr Ser Gln Asp Ile Asn Ile Tyr
20 25 30

Leu Asn Trp Tyr Gln Gln Lys Pro Gly Lys Ala Pro Lys Leu Leu Ile
35 40 45

Tyr Tyr Arg Ser Gly Leu Leu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Gly Asn Thr Leu Pro Pro
85 90 95

Thr Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 82
<211> LENGTH: 450
<212> TYPE: PRT
<213> ORGANISM: Artificial Sequence
<220> FEATURE:
<223> OTHER INFORMATION: Synthetic Sequence_Heavy chain sequence of Hu47-14

<400> SEQUENCE: 82

```
Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Tyr
            20                  25                  30

Gly Met Ser Trp Val Lys Gln Ala Pro Gly Gln Gly Leu Lys Trp Met
        35                  40                  45

Gly Trp Ile Asn Thr Tyr Ser Gly Val Pro Thr Tyr Ala Ser Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Arg Gly Asn Tyr Gly Arg Trp Asp Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
```

```
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 83
<211> LENGTH: 215
<212> TYPE: PRT
<213> ORGANISM: Artificial Sequence
<220> FEATURE:
<223> OTHER INFORMATION: Synthetic Sequence_Light chain sequence of
      Hu47-14

<400> SEQUENCE: 83

Glu Ile Val Leu Thr Gln Ser Pro Asp Phe Gln Ser Val Thr Pro Lys
1               5                   10                  15

Glu Lys Val Thr Ile Thr Cys Ser Val Ser Ser Thr Ile Ser Ser Ser
            20                  25                  30

Asn Leu His Trp Tyr Gln Gln Lys Pro Asp Gln Ser Pro Lys Pro Leu
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Leu Thr Ile Asn Ser Leu Glu
65                  70                  75                  80

Ala Glu Asp Ala Ala Thr Tyr Tyr Cys Gln Gln Trp Ser Ile Tyr Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160
```

-continued

```
Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 84
<211> LENGTH: 447
<212> TYPE: PRT
<213> ORGANISM: Artificial Sequence
<220> FEATURE:
<223> OTHER INFORMATION: Synthetic Sequence_Heavy chain sequence of
      Hu67-14

<400> SEQUENCE: 84

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

His Met Asn Trp Val Lys Gln Met Pro Gly Lys Gly Leu Glu Trp Met
        35                  40                  45

Gly Asp Ile Asn Pro Asp Ile Gly Gly Thr Ser Tyr Asn Gln Asn Phe
    50                  55                  60

Lys Gly Lys Val Thr Ile Ser Val Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Asp Phe Asp Ser Phe Ala Asn Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300
```

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Asp Glu Leu Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Lys
435 440 445

<210> SEQ ID NO 85
<211> LENGTH: 218
<212> TYPE: PRT
<213> ORGANISM: Artificial Sequence
<220> FEATURE:
<223> OTHER INFORMATION: Synthetic Sequence_Light chain sequence of Hu67-14

<400> SEQUENCE: 85

Asp Ile Gln Met Thr Gln Ser Pro Ser Ser Leu Ser Ala Ser Val Gly
1 5 10 15

Asp Arg Val Thr Ile Thr Cys Arg Ala Ser Glu Ser Val Ser Ile Ile
20 25 30

Gly Thr Asn Leu Ile His Trp Tyr Gln Gln Lys Pro Gly Lys Ala Pro
35 40 45

Lys Leu Leu Ile Tyr His Ala Ser Asn Leu Glu Thr Gly Val Pro Ser
50 55 60

Arg Phe Ser Gly Ser Gly Ser Gly Thr Asp Phe Thr Leu Thr Ile Ser
65 70 75 80

Ser Leu Gln Pro Glu Asp Phe Ala Thr Tyr Tyr Cys Leu Gln Ser Arg
85 90 95

Lys Ile Pro Tyr Thr Phe Gly Gly Gly Thr Lys Val Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys

```
    210                 215


<210> SEQ ID NO 86
<211> LENGTH: 452
<212> TYPE: PRT
<213> ORGANISM: Artificial Sequence
<220> FEATURE:
<223> OTHER INFORMATION: Synthetic Sequence_Heavy chain sequence of
      Hu103-32

<400> SEQUENCE: 86

Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Tyr
            20                  25                  30

Gly Val Ile Trp Val Arg Gln Ala Pro Gly Gln Gly Leu Glu Trp Met
        35                  40                  45

Gly Trp Ile Asn Thr Tyr Ser Gly Val Pro Thr Tyr Ala Ser Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Lys Lys Thr Leu Thr Thr Val Thr Pro Trp Phe Ala Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350
```

```
Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 87
<211> LENGTH: 221
<212> TYPE: PRT
<213> ORGANISM: Artificial Sequence
<220> FEATURE:
<223> OTHER INFORMATION: Synthetic Sequence_Light chain sequence of
      Hu103-32

<400> SEQUENCE: 87

Glu Leu Val Leu Thr Gln Ser Pro Ser Ala Ser Ala Ser Leu Gly Ala
1               5                   10                  15

Ser Val Lys Leu Thr Cys Thr Leu Ser Ser Gln His Ser Thr Tyr Thr
            20                  25                  30

Ile Glu Trp Tyr Gln Gln Gln Pro Glu Lys Gly Pro Arg Tyr Val Met
        35                  40                  45

Glu Leu Lys Lys Asp Gly Ser His Ser Thr Gly Glu Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asn
                85                  90                  95

Thr Ile Lys Glu Gln Phe Val Tyr Val Phe Gly Gly Gly Thr Lys Leu
            100                 105                 110

Thr Val Leu Gly Gln Pro Lys Ala Asn Pro Thr Val Thr Leu Phe Pro
        115                 120                 125

Pro Ser Ser Glu Glu Leu Gln Ala Asn Lys Ala Thr Leu Val Cys Leu
    130                 135                 140

Ile Ser Asp Phe Tyr Pro Gly Ala Val Thr Val Ala Trp Lys Ala Asp
145                 150                 155                 160

Gly Ser Pro Val Lys Ala Gly Val Glu Thr Thr Lys Pro Ser Lys Gln
                165                 170                 175

Ser Asn Asn Lys Tyr Ala Ala Ser Ser Tyr Leu Ser Leu Thr Pro Glu
            180                 185                 190

Gln Trp Lys Ser His Arg Ser Tyr Ser Cys Gln Val Thr His Glu Gly
        195                 200                 205

Ser Thr Val Glu Lys Thr Val Ala Pro Thr Glu Cys Ser
    210                 215                 220


<210> SEQ ID NO 88
<211> LENGTH: 450
<212> TYPE: PRT
<213> ORGANISM: Artificial Sequence
```

-continued

<220> FEATURE:
<223> OTHER INFORMATION: Synthetic Sequence_Heavy chain sequence of
Sanofi antibody

<400> SEQUENCE: 88

```
Glu Val Gln Leu Gln Glu Ser Gly Pro Gly Leu Val Lys Pro Gly Gly
1               5                   10                  15

Ser Leu Ser Leu Ser Cys Ala Ala Ser Gly Phe Val Phe Ser Ser Tyr
            20                  25                  30

Asp Met Ser Trp Val Arg Gln Thr Pro Glu Arg Gly Leu Glu Trp Val
        35                  40                  45

Ala Tyr Ile Ser Ser Gly Gly Gly Ile Thr Tyr Ala Pro Ser Thr Val
    50                  55                  60

Lys Gly Arg Phe Thr Val Ser Arg Asp Asn Ala Lys Asn Thr Leu Tyr
65                  70                  75                  80

Leu Gln Met Asn Ser Leu Thr Ser Glu Asp Thr Ala Val Tyr Tyr Cys
                85                  90                  95

Ala Ala His Tyr Phe Gly Ser Ser Gly Pro Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
```

```
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 89
<211> LENGTH: 214
<212> TYPE: PRT
<213> ORGANISM: Artificial Sequence
<220> FEATURE:
<223> OTHER INFORMATION: Synthetic Sequence_Light chain sequence of
      Sanofi antibody

<400> SEQUENCE: 89

Asp Ile Gln Met Thr Gln Ser Pro Ala Ser Leu Ser Ala Ser Val Gly
1               5                   10                  15

Asp Arg Val Thr Ile Thr Cys Arg Ala Ser Glu Asn Ile Phe Ser Tyr
            20                  25                  30

Leu Ala Trp Tyr Gln Gln Lys Pro Gly Lys Ser Pro Lys Leu Leu Val
        35                  40                  45

Tyr Asn Thr Arg Thr Leu Ala Glu Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Gln His His Tyr Gly Thr Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 90
<211> LENGTH: 449
<212> TYPE: PRT
<213> ORGANISM: Artificial Sequence
<220> FEATURE:
<223> OTHER INFORMATION: Synthetic Sequence_Heavy chain sequence of Lmab
      antibody

<400> SEQUENCE: 90

Glu Val Gln Leu Val Glu Ser Gly Gly Gly Val Val Gln Pro Gly Arg
```

-continued 1 5 10 15

Ser Leu Arg Leu Ser Cys Ser Ala Ser Gly Phe Asp Phe Thr Thr Tyr
20 25 30

Trp Met Ser Trp Val Arg Gln Ala Pro Gly Lys Gly Leu Glu Trp Ile
35 40 45

Gly Glu Ile His Pro Asp Ser Ser Thr Ile Asn Tyr Ala Pro Ser Leu
50 55 60

Lys Asp Arg Phe Thr Ile Ser Arg Asp Asn Ala Lys Asn Thr Leu Phe
65 70 75 80

Leu Gln Met Asp Ser Leu Arg Pro Glu Asp Thr Gly Val Tyr Phe Cys
85 90 95

Ala Ser Leu Tyr Phe Gly Phe Pro Trp Phe Ala Tyr Trp Gly Gln Gly
100 105 110

Thr Pro Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Arg Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

```
Ala Leu His Asn His Tyr Thr Gln Lys Ser Leu Ser Leu Ser Pro Gly
        435                 440                 445

Lys


<210> SEQ ID NO 91
<211> LENGTH: 213
<212> TYPE: PRT
<213> ORGANISM: Artificial Sequence
<220> FEATURE:
<223> OTHER INFORMATION: Synthetic Sequence_Light chain sequence of Lmab
      antibody

<400> SEQUENCE: 91

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ser
            20                  25                  30

Val Ala Trp Tyr Gln Gln Lys Pro Gly Lys Ala Pro Lys Leu Leu Ile
        35                  40                  45

Tyr Trp Thr Ser Thr Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Ser Leu Tyr Arg Ser
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 92
<211> LENGTH: 4
<212> TYPE: PRT
<213> ORGANISM: Artificial Sequence
<220> FEATURE:
<223> OTHER INFORMATION: Synthetic Sequence_Tetrapeptide linker

<400> SEQUENCE: 92

Gly Gly Phe Gly
1
```